US008304036B2

(12) United States Patent
Jansen et al.

(10) Patent No.: US 8,304,036 B2
(45) Date of Patent: Nov. 6, 2012

(54) 2, 5-SELENOPHENE DERIVATIVES AND 2, 5-TELLUROPHENE DERIVATIVES

(75) Inventors: Axel Jansen, Darmstadt (DE); Detlef Pauluth, Ober-Ramstadt (DE); Melanie Klasen-Memmer, Heuchelheim (DE)

(73) Assignee: Merck Patent Gesellschaft Mit Beschrankter Haftung, Darmstadt (DE)

( * ) Notice: Subject to any disclaimer, the term of this patent is extended or adjusted under 35 U.S.C. 154(b) by 147 days.

(21) Appl. No.: 12/676,646

(22) PCT Filed: Aug. 7, 2008

(86) PCT No.: PCT/EP2008/006501
§ 371 (c)(1),
(2), (4) Date: Mar. 5, 2010

(87) PCT Pub. No.: WO2009/033532
PCT Pub. Date: Mar. 19, 2009

(65) Prior Publication Data
US 2010/0216986 A1 Aug. 26, 2010

(30) Foreign Application Priority Data
Sep. 6, 2007 (DE) .......................... 10 2007 042 413

(51) Int. Cl.
*C09K 19/34* (2006.01)
*C09K 19/32* (2006.01)
*C09K 19/30* (2006.01)
*C09K 19/12* (2006.01)
*C07D 345/00* (2006.01)

(52) U.S. Cl. ............... 428/1.1; 252/299.61; 252/299.62; 252/299.63; 252/299.66; 540/1

(58) Field of Classification Search ............ 428/1.1; 252/299.61, 299.62, 299.63, 299.66; 540/1
See application file for complete search history.

(56) References Cited

FOREIGN PATENT DOCUMENTS

| EP | 1726589 A2 | 11/2006 |
| EP | 1792613 A2 | 6/2007 |
| JP | 2006076928 A | 3/2006 |
| JP | 2006076928 W | 3/2006 |
| WO | 2005019156 A2 | 3/2005 |
| WO | 2006094645 A1 | 9/2006 |

OTHER PUBLICATIONS

Alves, D. et al. "Electrophilic Cyclization of (Z)-Selenoenynes: Synthesis and Reactivity of 3-Iodoselenophenes." (J. Org. Chemistry), 2007, 6726-6734, 72.
Arsenyan, P. et al. "A novel method for the synthesis of 2,5-diarylselenophenes." (Tetrahedron Letters), 2002, 4817-4819, 43.
Curtis, R. et al. "Selenophenes from Diacetylenes" (Chemical Communications), 1968, 365, 7.
Dabdoub, M. et al. "Iodocyclization of (Z)-1-(Butyltelluro)-1,4-diorganylbut-1-en-3-ynes. Synthesis and Reactions of 3-Iodotelluophenes." (J. Org. Chemicals), 1996, 9503-9511, 61.
Davies, A. and Schiesser, C. "An electron spin resonance study of the 2,5-diphenylchalcophene radical ions." (Journal of Organometallic Chemistry), 1990, 301-313, 389.
Do Rego Barros, O. et al. "Palladium-catalyzed cross-coupling of 2-haloselenophene with terminal alkynes in the absence of additive." (Tetrahedron Letters), 2006, 2179-2182, 47.
Fringuelli, F. et al. "Heteroaromatic Rings as Substituents. Part 5. Evaluation of δ and δ-constants of 2-Selenienyl and 2-Tellurienyl Groups." (Journal of the Chemical Society, Perkin Transactions 2: Physical Organic Chemistry 1972-1990), 1980, 971-975, 7.
Gleeson, H. and Singh, U. "The Effect of Polymer Stabilization on Phase Transitions in a Series of Antiferroelectric Heterocyclic Esters." (Mol. Crystal Liq. Crystal), 2005, 135[2001]-145[2011], 439.
Ismail, M. et al. "An efficient synthesis of 5,5'-diaryl-2,2'-bichalcophenes." (Tetrahedron Letters), 2006, 795-797, 47.
Katkevics, M. et al. "From Tellurophenes to Silloles. Synthesis, Structures, and Photophysical Properties of 3,4-Unsubsitituted 2,5-Diarylsiloles.", Organometallics,1998, 17(26) , pp. 5796-5800.
Kharchenko, V. et al. "Reaction of arylfurans with hydrogen sulfide and hydrogen selenide under acid catalysis conditions." (Khimiya Geterotsiklicheskikh Soedinenii), 1984, 1606-1608, 12.
Lalezari, I. Et al. "Selenium Heterocycles. XII (1). Heat Induced Transformation of 1,2,3-Selenadiazoles to Disubstituted Selenophenes (2)." (Journal of Heterocyclic Chemistry), 1973, 953-955, 10.
Lalezari, I. Et al. "Selenium Heterocycles. XIX (1). Synthesis of Selenophenes and Triarylbenzenes from 2,5-Diaryl-1,4-dithiin,1,1,4,4-Tetroxides." (Journal of Heterocyclic Chemistry, 1976, 57-60, 13.
Mills et al. "X-ray and optical studies of the tilted phases of materials exhibiting antiferroelectric, ferrielectric and ferroelectric mesophases." (J. Mater. Chem.), 1998, 2385-2390, 8:11.
Mills, J. et al. "The physical properties of a series of antiferroelectric heterocyclic esters." (Mol. Crystal Liq. Crystal), 1997, 145-152, 303.
Okuma, K. et al. "Reaction of Ketone Hydrazones with Deselenium Dihalides:Simple Synthesis of Δ3-1,3,4-Selenadiazolines and 2,5-Diarylselenophenes." (Bulletin of the Chemical Society of Japan), 2005, 1121-1126, 78.
Panatieri, R. et al. "Synthesis of 2-Alkynyl-Tellurophene Derivatives via Palladium-Catalyzed Cross-Coupling." (Synlett), 2006, 3161-3163, 18. Prediger, P. et al. "Palladium-Catalyzed Suzuki Cross-Coupling of 2-Haloselenophenes: Synthesis of 2-Arylselenophenes, 2,5-Diaryselenophenes, and 2-Arylselenophenyl Ketones." (Journal of Organic Chemistry), 2006, 3786-3792, 71:10.
Prim, D. et al. "Synthesis of new 2,5-diaryl selenophenes." (Phosphorous, Sulfur and Silicon), 1994, 137-143, 91.
Roberts, N. et al. "An experimental and theoretical investigation into the reflection spectra of SmC* and SmCA* phases." (J. Mater. Chem.) 2003, 353-359, 13.

(Continued)

*Primary Examiner* — Shean Wu
(74) *Attorney, Agent, or Firm* — Millen, White, Zelano & Branigan, P.C.

(57) ABSTRACT

The invention relates to 2,5-selenophene derivatives and 2,5-tellurophene derivatives, inter alia for use as components in liquid-crystal mixtures, and to liquid-crystal mixtures which comprise the compounds, and to liquid-crystal displays based on these mixtures. The invention furthermore relates to processes for the preparation of the compounds and to Se/Te-containing intermediates.

20 Claims, No Drawings

OTHER PUBLICATIONS

Schatz, J. "Fully Unsaturated Small Ring Heterocycles and Monocyclic Five-Membered Hetarenes with One Heteroatom." (Science of Synthesis), 2000, 423-430, 9.

Schulte, K. et al. "Thiopene and Selenophene aus α-Propinyl-carbonyl-Verbindungen" (Chemische Berichte), 1968, 1540-1552, 101.

Seed, A. et al. "Heterocyclic Esters exhibiting frustrated liquid crystal phases." (Mol. Crystal Liq. Crystal), 1997, 19-25, 299.

Singh, U. et al. "Optical bragg reflections from a series of ferroelectric heterocyclic esters." (Ferroelectrics), 2002, 153-167, 277.

Zeni, G. "Carbon-sulfur bond formation from 2-halochalcogenophenes via copper catalyzed thiol cross-coupling." (Tetrahedron Letters), 2005, 2657-2651, 46.

2,5-SELENOPHENE DERIVATIVES AND 2,5-TELLUROPHENE DERIVATIVES

The invention relates to 2,5-selenophene derivatives and 2,5-tellurophene derivatives, inter alia for use as components in liquid-crystal mixtures, and to liquid-crystal mixtures which comprise the compounds, and to liquid-crystal displays based on these mixtures. The invention furthermore relates to processes for the preparation of the compounds and to Se/Te-containing intermediates.

Polyselenophene compounds and copolymers comprising selenophene compounds are used principally as organic semiconductor materials or as electrically conductive polymers [for example WO 2006/094645 A1, WO 2005/111045 A1].

Liquid-crystalline compounds containing selenophene units and/or tellurophene units for use as components in liquid-crystal mixtures and liquid-crystal mixtures comprising such compounds are virtually unknown to date.

Only a group of ferroelectric materials of the general formula 1 is described in the publication WO 2005/019156 A2.

X-alkylene-$A^1$-alkylene-$A^2$-$(Z^1)_x$-B-$(Z^2)_y$-C-$(Z^3)_z$-$A^3$-alkyl       1 in which $Z^1$, $Z^2$ and $Z^3$ denote a group from

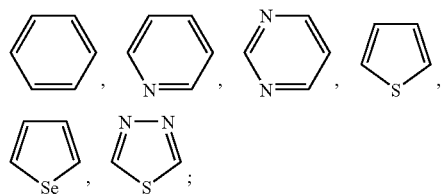

$A^1$, $A^2$ and $A^3$ denote —O—, —(CO)O—, —O(CO)— or —S—;

B, C denote a single bond, —(CO)O—, —O(CO)—, —CH$_2$O—, —CF=CF— or —C≡C—,

X denotes a group from the radicals

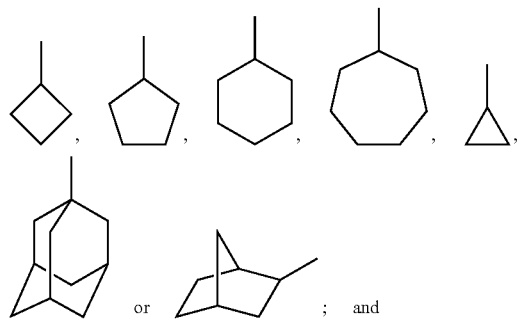

x, y, z denote 1 or 2.

The materials described have exclusively smectic phases (SmA, SmC*, etc.), and specific selenophene compounds are not disclosed.

A selenophene compound of the following formula 2 has been disclosed by A. J. Seed et al. (*Mol. Dyst, Liq. Cryst.* 1997, 299, 19-25):

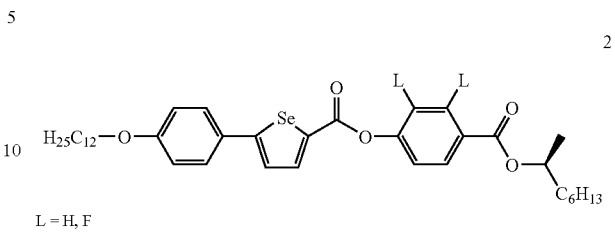

L = H, F

In a series of further publications by the authors, specific investigations of this compound have been published. It has exclusively smectic, principally antiferroelectric, phases. The chiral alkyl radical is bonded to the closest ring of the mesogenic group via an ester group —(CO)O—.

A selenophene bromide of the formula 3 is disclosed as synthetic intermediate in EP 1792613 A2:

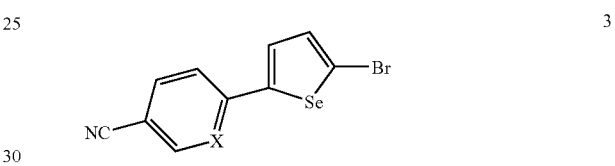

in which X denotes a CH or N group.

The use of liquid-crystalline tellurophene compounds I (Y=Te) in display elements has not yet been described.

For the purposes of the present application, the term chalcogenophene represents a collective term for the 5-membered aromatic heterocycles selenophene or tellurophene.

Liquid crystals have found widespread use since the first commercially usable liquid-crystalline compounds were found about 30 years ago. Known areas of application of conventional mixtures are, in particular, displays for watches and pocket calculators, and display panels as used in railway stations, airports and sports arenas. Further areas of application are displays of portable and desktop computers and navigation systems and video applications. For the last-mentioned applications in particular, high demands are made of the response times and contrast of the images.

The spatial arrangement of the molecules in a liquid crystal has the effect that many of its properties are direction-dependent. Of particular importance for use in liquid-crystal displays are the optical, dielectric and elastomechanical anisotropies. Depending on whether the molecules are oriented with their longitudinal axes perpendicular or parallel to the two plates of a capacitor, the latter has a different capacitance; in other words, the dielectric constants of the liquid-crystalline medium has different values for the two orientations. Substances whose dielectric constant is larger when the longitudinal axes of the molecules are oriented perpendicular to the capacitor plates than when they are oriented parallel are referred to as dielectrically positive. In other words, if the dielectric constant $\epsilon_\parallel$ parallel to the longitudinal axes of the molecules is larger than the dielectric constant $\epsilon_\perp$ perpendicular to the longitudinal axes of the molecules, the dielectric anisotropy $\Delta\epsilon = \epsilon_\parallel - \epsilon_\perp$ is greater than zero. Most liquid crystals used in conventional displays fall into this group.

Both the polarizability of the molecule and the permanent dipole moment play a role for the dielectric anisotropy. On application of a voltage to the display, the longitudinal axis of the molecules orients itself in such a way that the larger of the dielectric constants becomes effective. The strength of the interaction with the electric field depends on the difference between the two constants. In the case of small differences, higher switching voltages are necessary than in the case of large differences. The introduction of suitable polar groups, such as, for example, nitrile groups or fluorine, into the liquid-crystal molecules enables a broad range of working voltages to be achieved.

In the case of the liquid-crystalline molecules used in conventional liquid-crystal displays, the dipole moment oriented along the longitudinal axis of the molecules is larger than the dipole moment oriented perpendicular to the longitudinal axis of the molecules. In the most widespread TN ("twisted nematic") cells, a liquid-crystalline layer with a thickness of only from about 5 to 10 μm is arranged between two plane-parallel glass plates, onto each of which an electrically conductive, transparent layer of indium tin oxide (ITO) has been vapour-deposited as electrode. A likewise transparent alignment layer, usually consisting of a plastic (for example polyimides), is located between these films and the liquid-crystalline layer. This alignment layer serves to bring the longitudinal axes of the adjacent liquid-crystalline molecules into a preferential direction through surface forces in such a way that, in the voltage-free state, they lie uniformly with the same orientation, flat or with the same small tilt angle, on the inside of the display surface. Two polarisation films which only enable linear-polarised light to enter and escape are applied to the outside of the display in a certain arrangement.

By means of liquid crystals in which the larger dipole moment is oriented parallel to the longitudinal axis of the molecule, very high-performance displays have already been developed. In most cases here, mixtures of from 5 to 20 components are used in order to achieve a sufficiently broad temperature range of the mesophase and short response times and low threshold voltages. However, difficulties are still caused by the strong viewing-angle dependence in liquid-crystal displays as are used, for example, for laptops. The best imaging quality can be achieved if the surface of the display is perpendicular to the viewing direction of the observer. If the display is tilted relative to the observation direction, the imaging quality deteriorates drastically under certain circumstances. For greater comfort, attempts are being made to maximise the angle through which the display can be tilted from the viewing direction of an observer without significantly reducing the imaging quality. Attempts have recently been made to improve the viewing-angle dependence using liquid-crystalline compounds whose dipole moment perpendicular to the longitudinal axis of the molecule is larger than that parallel to the longitudinal axis of the molecule. The dielectric anisotropy $\Delta\epsilon$ is negative in this case. In the field-free state, these molecules are oriented with their longitudinal axis perpendicular to the glass surface of the display. Application of an electric field causes them to orient themselves more or less parallel to the glass surfaces. In this way, it has been possible to achieve an improvement in the viewing-angle dependence. Displays of this type are known as VA-TFT ("vertically aligned") displays.

Development in the area of liquid-crystalline materials is still far from complete. In order to improve the properties of liquid-crystalline display elements, attempts are constantly being made to develop novel compounds which enable optimisation of such displays.

It is therefore an object of the present invention to provide compounds having advantageous properties for use in liquid-crystalline media. This is achieved by the use of the compounds of the formula I according to the invention:

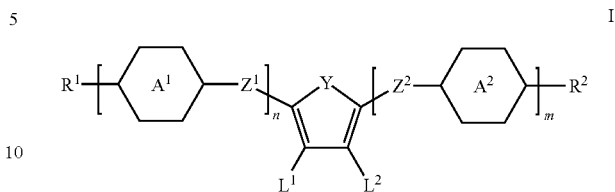

in which

Y denotes Se or Te, $L^1$ and $L^2$, independently of one another, denote H, halogen, CN, $CF_3$ or an alkyl group having 1 to 5 C atoms, $R^1$ and $R^2$ each, independently of one another, denote H, F, Cl, —CN, —NCS, —$SF_5$, —$CF_3$, —$CHF_2$, —$CH_2F$, —$OCF_3$, —$OCHF_2$, —$OCH_2F$ or an alkyl group having 1 to 15 C atoms, which may optionally be monosubstituted by CN or at least monosubstituted by halogen, where in each case, in addition, one or more $CH_2$ groups may each be replaced, independently of one another, by —O—, —S—, —CH=CH—, —CF=CF—, —CF=CH— or —CH=CF— in such a way that neither O nor S atoms are linked directly to one another, or a polymerisable group,

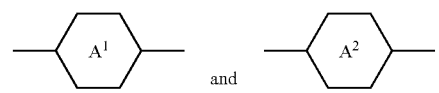

each, independently of one another, denote (a) a trans-1,4-cyclohexylene radical, in which, in addition, one or two non-adjacent $CH_2$ groups may be replaced by —O— and/or —S—, (b) a 1,4-cyclohexenylene radical, (c) a 1,4-phenylene radical, in which, in addition, one or two non-adjacent CH groups may be replaced by N, or (d) a radical selected from the group naphthalene-2,6-diyl, decahydronaphthalene-2,6-diyl, 1,2,3,4-tetrahydronaphthalene-2,6-diyl and indane-2,5-diyl, or (e) a radical selected from the group 1,3-cyclobutylene, 1,4-bicyclo-[2.2.2]octylene, 1,3-bicyclo[1.1.1]pentylene and spiro[3.3]heptane-2,6-diyl, (f) a radical selected from the group of the following formulae and their mirror images

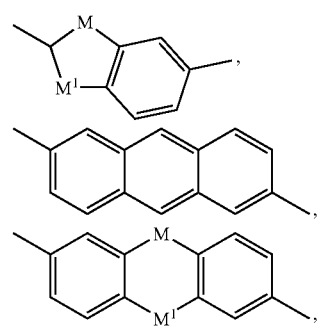

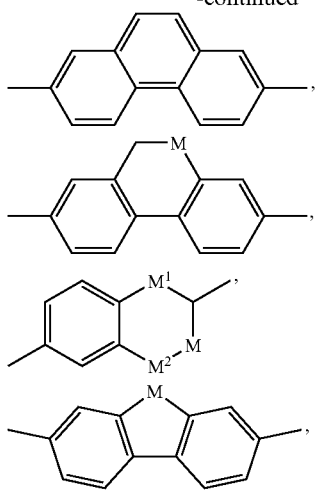

in which hydrogen atoms may be mono- or polysubstituted by F, Cl, CN, NCS, SF$_5$, CH$_2$F, CHF$_2$, CF$_3$, OCH$_2$F, OCHF$_2$ or OCF$_3$, one or more double bonds may be replaced by single bonds, M, M$^1$ or M$^2$ denotes —O—, —S—, —CH$_2$—, —CHY$^1$— or —CY$^1$Y$^2$— in such a way that adjacent groups do not simultaneously denote —O— or —S—, and Y$^1$ and Y$^2$ denote Cl, F, CN, OCF$_3$ or CF$_3$, where, in (a) and (b), one or more H atoms may be replaced by F and, in (b), (c) and (d), one, two or three —CH= groups may each be replaced, independently of one another, by a group selected from the group —CF=, —CCl=, —CBr=, —C(CN)=, —C(CH$_3$)=, —C(CH$_2$F)=, —C(CHF$_2$)=, —C(OCH$_3$)=, —C(OCHF$_2$)= and —C(OCF$_3$)= and one or more —CH$_2$— groups may be replaced by —CF$_2$—, Z$^1$ and Z$^2$ each, independently of one another, denote a single bond, —CH$_2$—CH$_2$—, —CF$_2$—CH$_2$—, —CH$_2$—CF$_2$—, —CF$_2$—CF$_2$—, —CHF—CHF—, —CH$_2$—CHF—, —CHF—CH$_2$—, —CH=CH—, —CF=CF—, —CF=CH—, —CH=CF—, —C≡C—, —(CO)O—, —O(CO)—, —CH$_2$O—, —OCH$_2$—, —CF$_2$O—, —OCF$_2$— or a combination of two of these groups, where no two O atoms are connected to one another, and n and m each, independently of one another, denote 0, 1, 2, 3 or 4, where (n+m) denotes 1, 2, 3 or 4, with the proviso that compounds to which the following applies, that the group R$^1$ or R$^2$ denotes hydrogen and at the same time the group A$^1$ or A$^2$ connected thereto denotes a 1,4-cyclohexenylene radical or 1,3-cyclobutylene radical, that R$^1$ and R$^2$ both denote H, both denote F or both denote Cl, that n=0 or 1, m=1, Z$^2$=a single bond, A$^1$=A$^2$=1,4-phenylene and R$^2$=CN, OH or H, that n=0, m=1, Z$^2$=a single bond, A$^2$=1,4-phenylene and R$^1$=H, or that they have a structure of the formulae

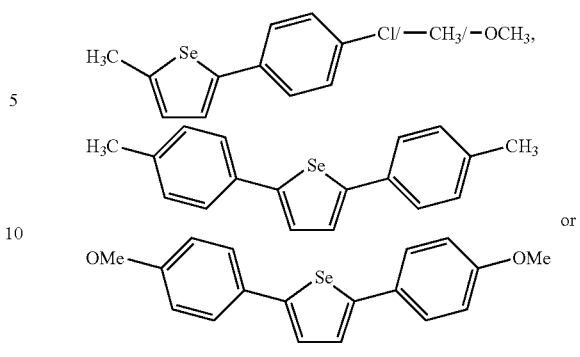

are excluded.

The compounds of the formula I do not include any compounds of the above-mentioned compounds of the formulae 1, 2 or 3, since they have at least one structural difference.

The invention furthermore relates to the use of the compounds of the formula I as component of a liquid-crystalline medium, in particular a nematic medium.

The compounds according to the invention may also be chiral, i.e. contain chiral groups. In this case, an enantiomeric excess of one enantiomer may also be present. The compounds preferably contain no chiral groups or the optionally optically active compounds are in the form of a racemate.

The groups L$^1$ and L$^2$ preferably denote, independently of one another, H, F, Cl, CN or CF$_3$ or a branched or unbranched alkyl group having 1 to 5 C atoms, particularly preferably H or F and very particularly preferably H. L$^1$ and L$^2$ are preferably both H.

The rings A$^1$ and A$^2$ preferably denote a group from groups (a) to (d) defined above, particularly preferably from groups (a) to (c) and very particularly preferably from groups (a) and (c). Furthermore, the rings A$^1$ and A$^2$ are very particularly preferably rings of the formulae

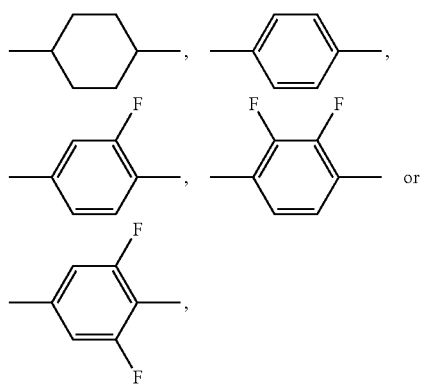

and furthermore rings of the formulae

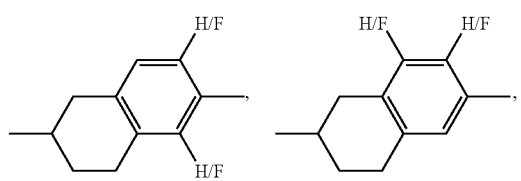

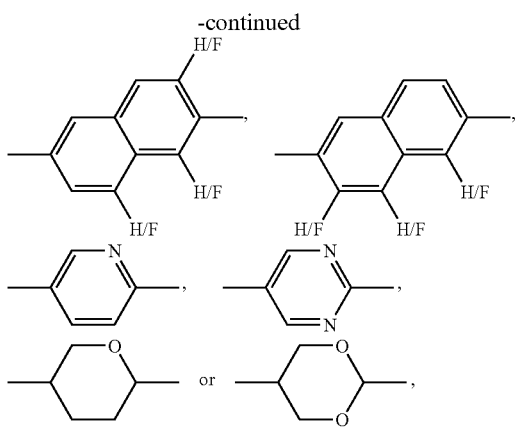

including their mirror images.

$R^1$ and $R^2$ preferably denote alkyl, alkoxy, alkenyl or alkenyloxy having up to 8, preferably having 2 to 6, carbon atoms, particularly preferably straight-chain alkyl, alkoxy or alkenyl. At the same time, one group from $R^1$ and $R^2$ may also additionally denote F, Cl, —CN, —NCS, —$SF_5$, —$CF_3$, —$CHF_2$, —$CH_2F$, —$OCF_3$, —$OCH_2F$ or —$OCHF_2$, preferably F, —$CF_3$, —$CHF_2$, —$CH_2F$, —$OCF_3$, —$OCH_2F$ or —$OCHF_2$. Of the polar groups, F, —CN and —$OCF_3$ are particularly preferred.

Compounds of the formula I containing branched wing groups $R^1$ or $R^2$ may occasionally be of importance owing to better solubility in conventional liquid-crystalline base materials, but in particular as chiral dopants if they are optically active.

In addition, one or both groups $R^1$ and $R^2$ can represent a chiral radical. $R^1/R^2$ can represent a polymerisable group inside or outside the general definition of the groups.

The groups $R^1/R^2$ therefore additionally denote a polymerisable group, in particular of the formula —(S)$_r$—P in which S denotes a so-called spacer, i.e., in particular, a 1-15-C alkylene, in which one or more —$CH_2$— may be replaced by —O—, —CO—, —O(CO)— or —(CO)O— in such a way that two oxygen atoms are not adjacent, r denotes 0 or 1, and P denotes a polymerisable group, preferably acryloyl, methacryloyl, oxetanyl, epoxide, vinyl, vinyloxy, propenyloxy or styroyl, in particular acryl or methacryl.

Compounds of the formula I which contain wing groups $R^1$ and/or $R^2$ which are suitable for polymerisation reactions are suitable for the preparation of liquid-crystalline polymers.

The groups $Z^1$ and $Z^2$ are preferably, independently of one another, groups selected from —$CH_2$—$CH_2$—, —$CF_2$—$CF_2$—, —CH=CH—, —CF=CF—, —C≡C—, —$CH_2O$—, —$OCH_2$—, —$CF_2O$—, —$OCF_2$— or a single bond. Very particularly preferably, one or both of the groups $Z^1$ and $Z^2$ are a single bond.

$A^1$ and $A^2$ can each, independently, also adopt different meanings in all formulae above and below if they occur more than once for m or n>1. The same applies to $Z^1$ and $Z^2$.

The compounds of the formula I, alone or in mixtures, form liquid-crystal-line mesophases in a temperature range which is favourably located for electro-optical use. The compounds according to the invention enable broad nematic phase ranges to be achieved. This is surprising against the prior art since the selenophene compounds known to date are exclusively of a smectic nature.

The compounds according to the invention have a relatively low rotational viscosity and a low clearing point, alone or in liquid-crystalline mixtures. In particular, they generally have a favourable ratio of the rotational viscosity to the clearing point. Furthermore, the compounds are readily soluble in the usual liquid-crystalline media for display devices.

Halogen in connection with the present invention denotes fluorine, chlorine, bromine or iodine, in particular fluorine or chlorine and very particularly fluorine.

In an embodiment of the invention, particular preference is also given to compounds of the formula I for which m+n=2 or 3 and/or for which m+n=1, where, for n=1 and m=0, the substituent $R^1$ preferably denotes alkyl, alkoxy, alkenyl or alkenyloxy having 2 to 6 carbon atoms and $R^2$ is as defined in accordance with one of the above definitions, in particular 1-8 C alkyl or fluorine (corresponding definitions apply for n=0 and m=1).

For the compounds of the formula I, in particular for n+m=1, it is therefore preferred for both radicals $R^1$ and $R^2$ not to denote H. For m+n=2, preferably m or n=0. For n=m=1, the groups $A^1$ and $A^2$ preferably have different meanings, i.e. particularly not simultaneously unsubstituted 1,4-phenylene or 1,4-cyclohexylene, in particular not 1,4-phenylene. The preferred compounds generally have a high tendency to form nematic liquid-crystalline phases and a high clearing point, as the pure substance or in a mixture with suitable co-components, if the pure substance does not form such a phase.

Particular preference is given to compounds of the formula I according to the invention selected from the sub-formulae IA and IB (where IA: Y=Se, $L^1$=$L^2$=H and IB: Y=Te, $L^1$=$L^2$=H):

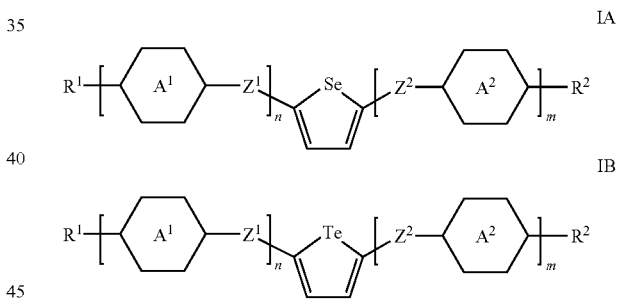

in which the parameters have the respective meanings given above under formula I.

Particular preference is given to compounds of the formula IA selected from the group of the compounds of the formulae IA-1 to IA-14, preferably of the formulae in which at least one of the groups $R^1$ and $R^2$ is linked directly to the selenophene unit, particularly preferably of the formulae IA-1, IA-2 and IA-4, furthermore IA-9 to IA-14, in which (n+m)=1, 2 or 3. Very particular preference is given to compounds of the formulae IA-1 and IA-2 in which (n+m)=1 or 2.

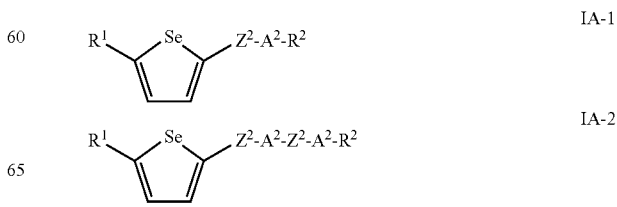

-continued

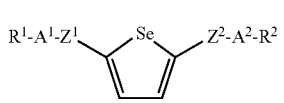
IA-3

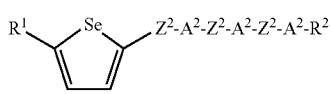
IA-4

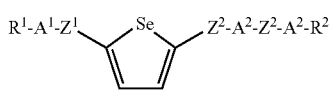
IA-5

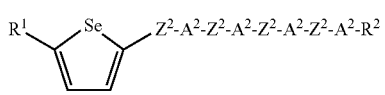
IA-6

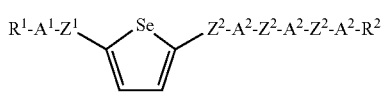
IA-7

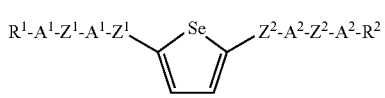
IA-8

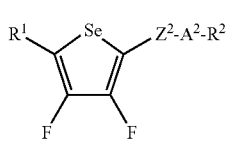
IA-9

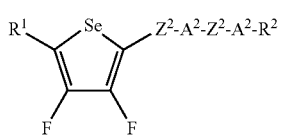
IA-10

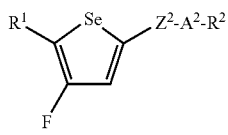
IA-11

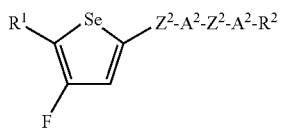
IA-12

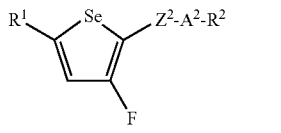
IA-13

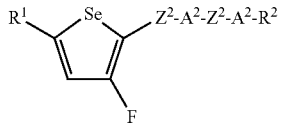
IA-14 in which the parameters have the respective meanings indicated above.

The compounds of the formula IA-3 preferably have a structure of the formula IA-3a:

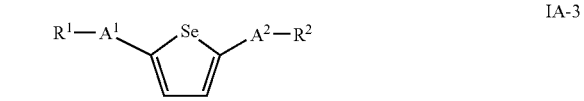
IA-3

A corresponding situation applies to the formula IB-3 below.

Very generally, combinations of the preferred embodiments of the invention indicated above and below are also to be regarded as particularly preferred, so long as they can formally be combined with one another.

Particular preference is given to compounds of the formula IB selected from the group of the compounds of the formulae IB-1 to IB-14, preferably of the formulae in which at least one of the groups $R^1$ and $R^2$ is linked directly to the tellurophene unit, particularly preferably of the formulae IB-1, IB-2 and IB-4, furthermore IB-9 to IB-14, in which (n+m)=1, 2 or 3. Very particular preference is given to compounds of the formulae IB-1 and IB-2 in which (n+m)=1 ort.

IB-1

IB-2

IB-3

IB-4

IB-5

IB-6

IB-7

IB-8

IB-9

IB-10

-continued

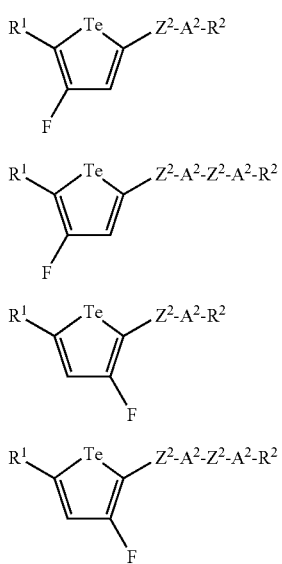

in which the parameters have the respective meanings indicated above.

Examples of structures of preferred compounds of the formula I are given below, arranged by sub-formula, in which p denotes 0, 1, 2, 3 or 4, and, in the case where p occurs more than once, these, independently of one another, preferably denote 0, 1 or 2, and

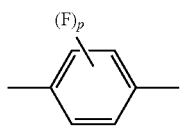

independently of one another, denotes a group from

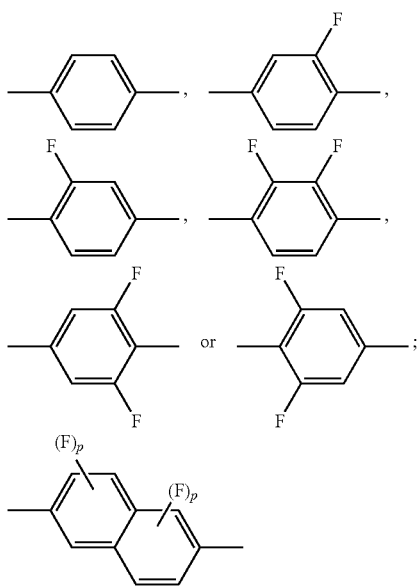

independently of one another, denotes a group from

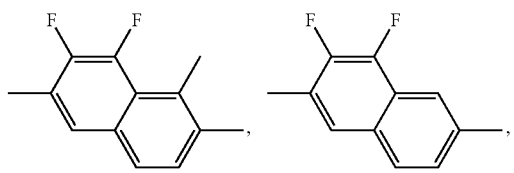
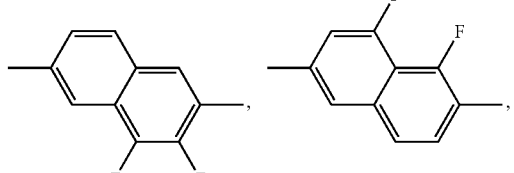
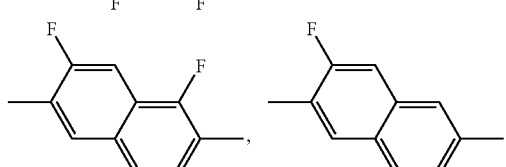
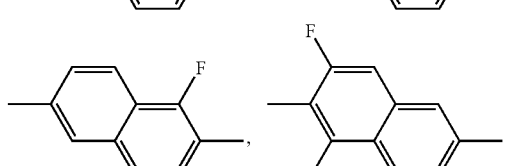
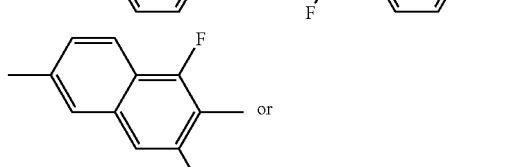
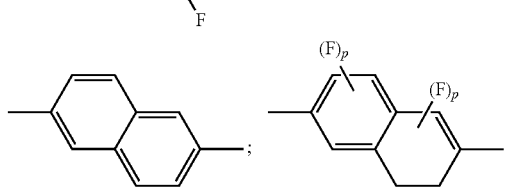

independently of one another, denotes a group from

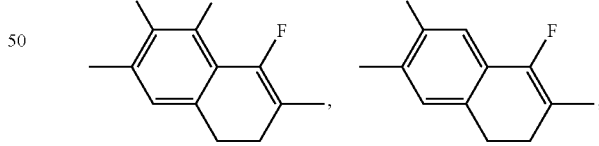
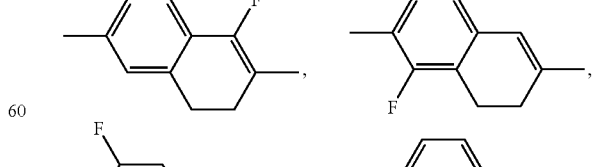

-continued
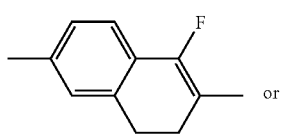
or
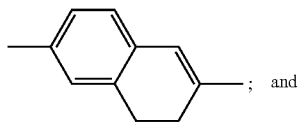
; and
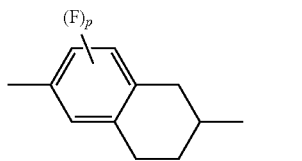
independently of one another, denotes a group from
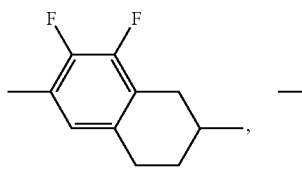 , 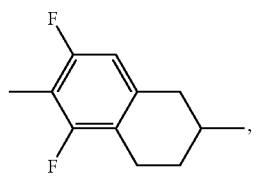 ,
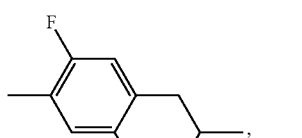 ,
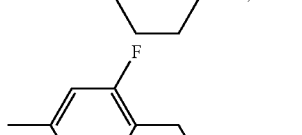 or
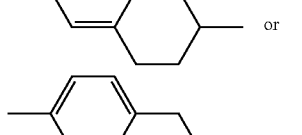 .
Preferred compounds of the formula IA-1 are:
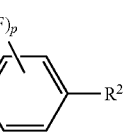
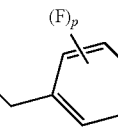
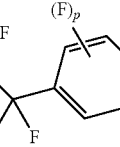
-continued
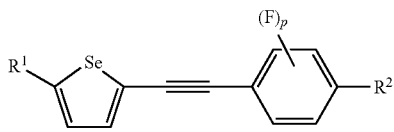
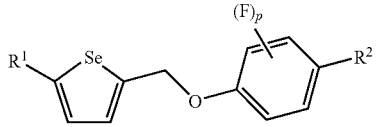
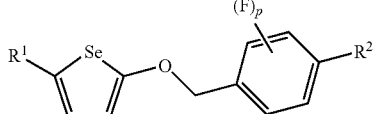
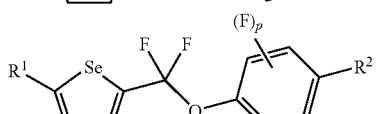
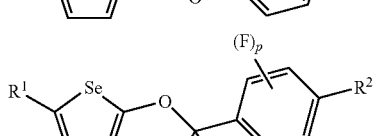
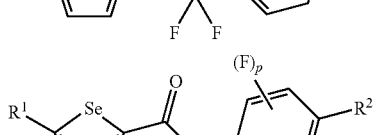
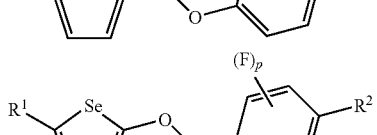
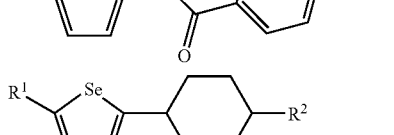
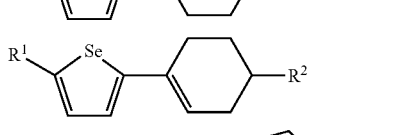
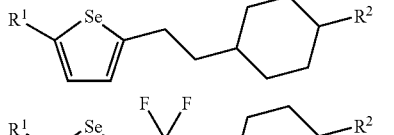
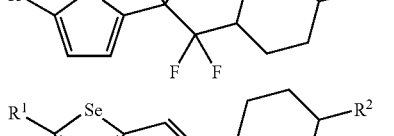
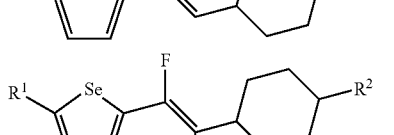
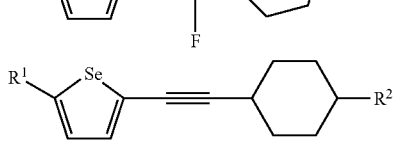

-continued

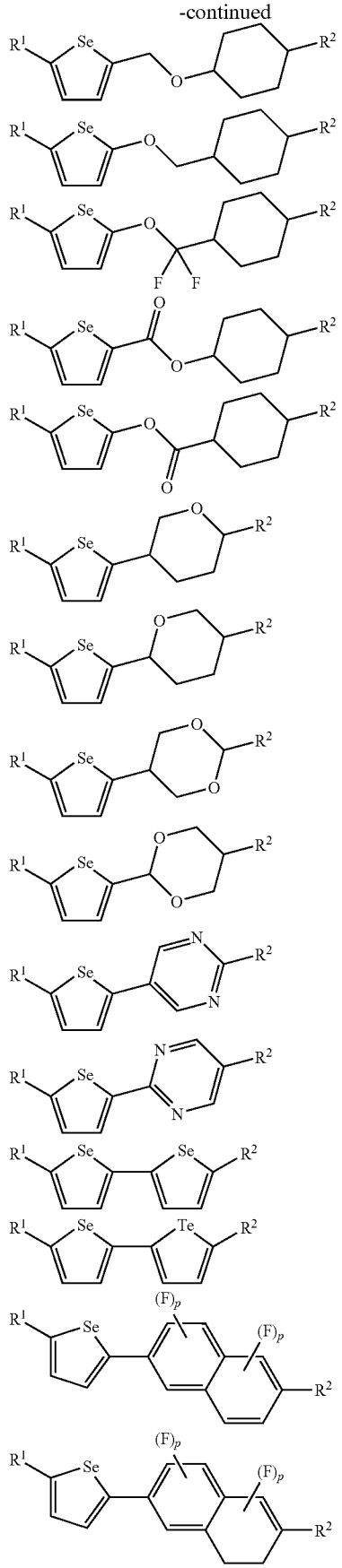

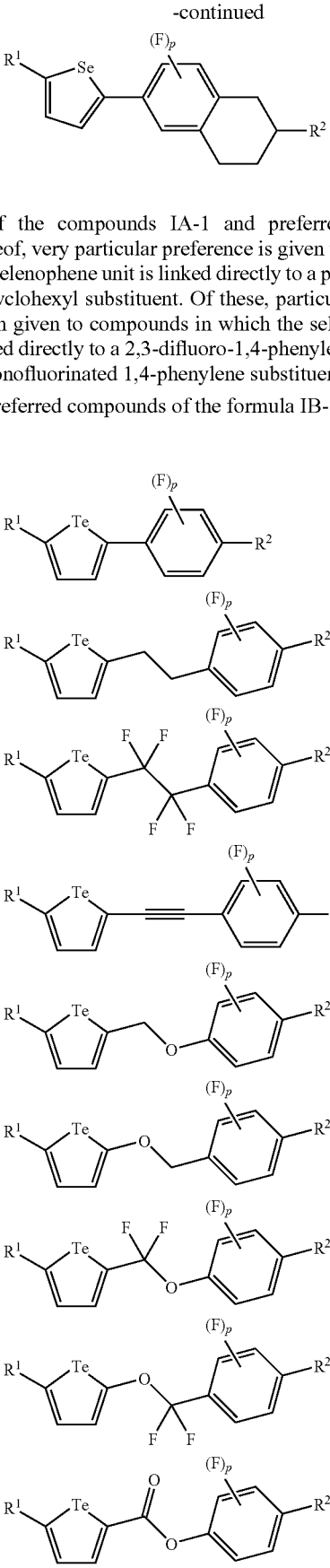

Of the compounds IA-1 and preferred embodiments thereof, very particular preference is given to those in which the selenophene unit is linked directly to a phenyl substituent or cyclohexyl substituent. Of these, particular preference is again given to compounds in which the selenophene unit is linked directly to a 2,3-difluoro-1,4-phenylene substituent or a monofluorinated 1,4-phenylene substituent.

Preferred compounds of the formula IB-1 are:

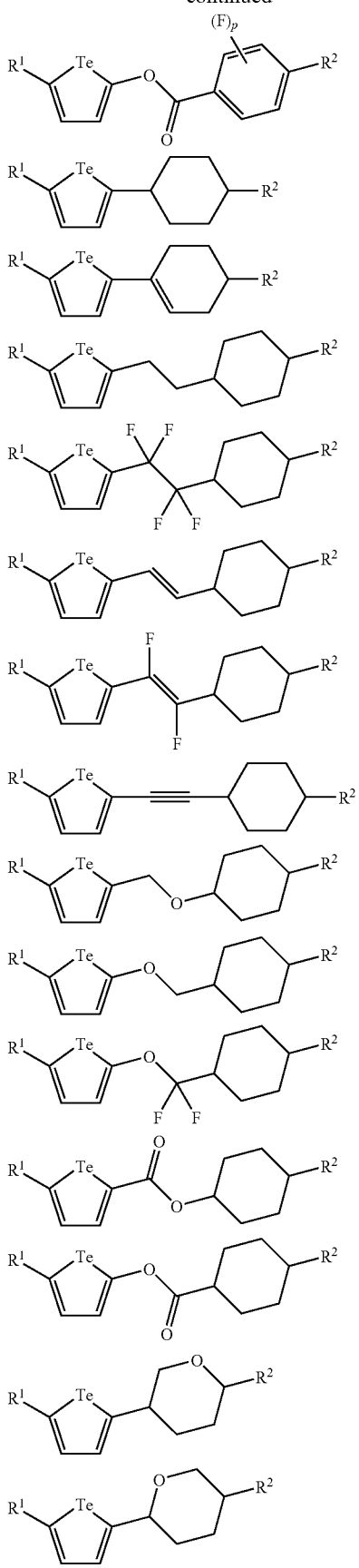
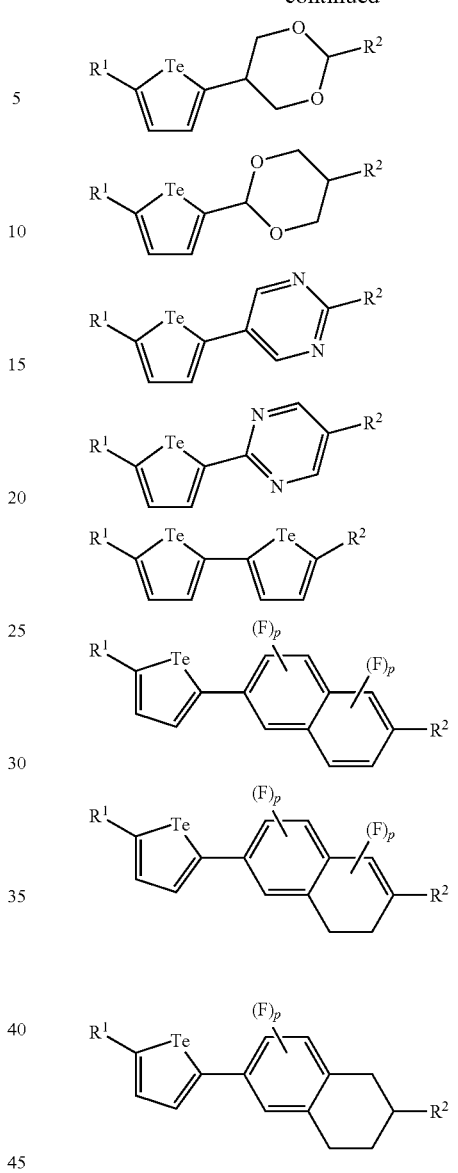
Of the compounds IB-1 and preferred embodiments thereof, very particular preference is given to those in which the tellurophene unit is linked directly to a phenylene substituent or cyclohexylene substituent.
Preferred compounds of the formula IA-2 are:
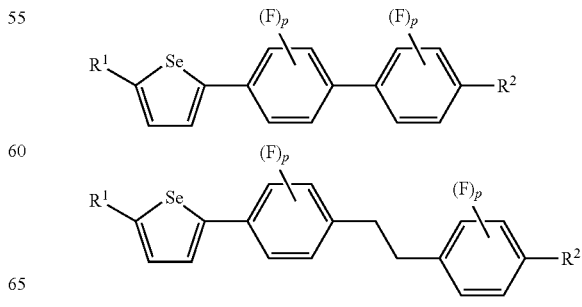

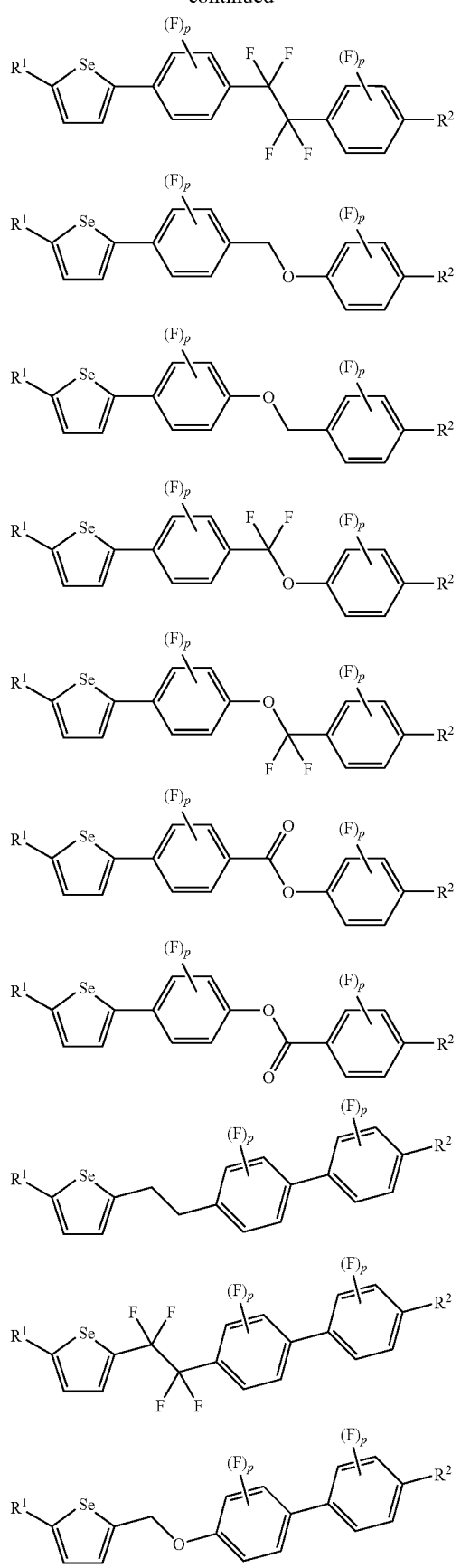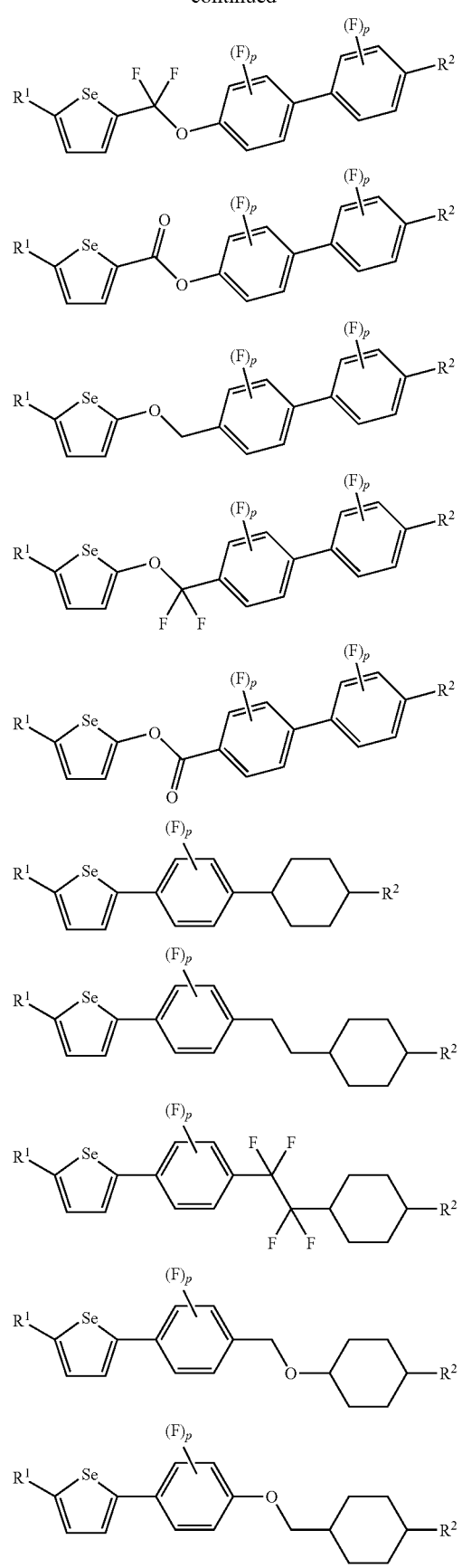

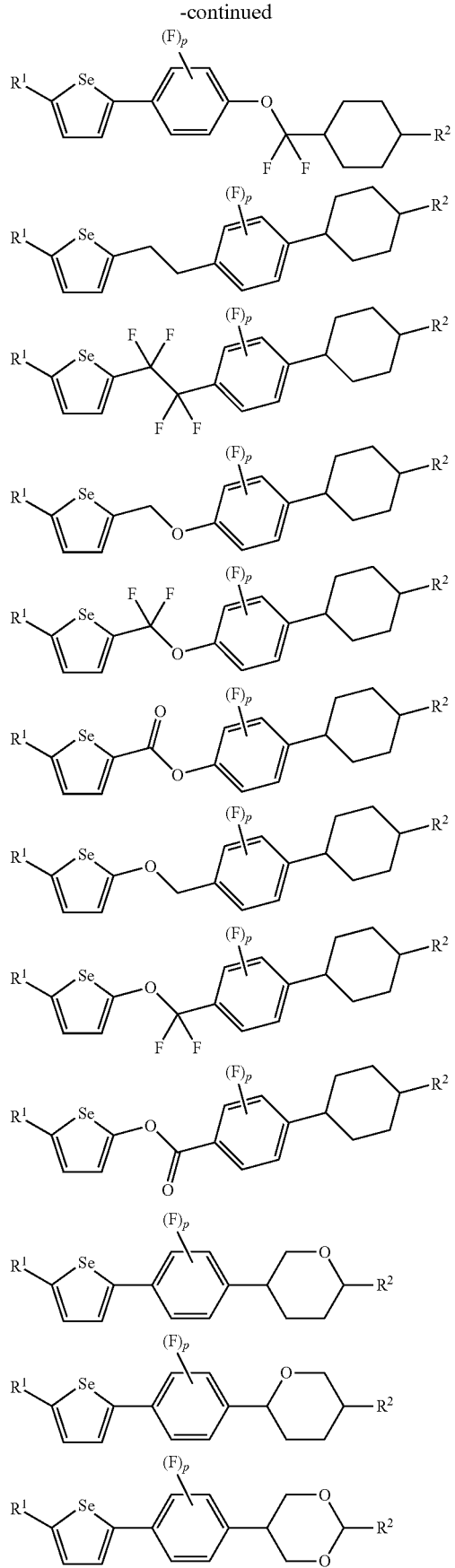
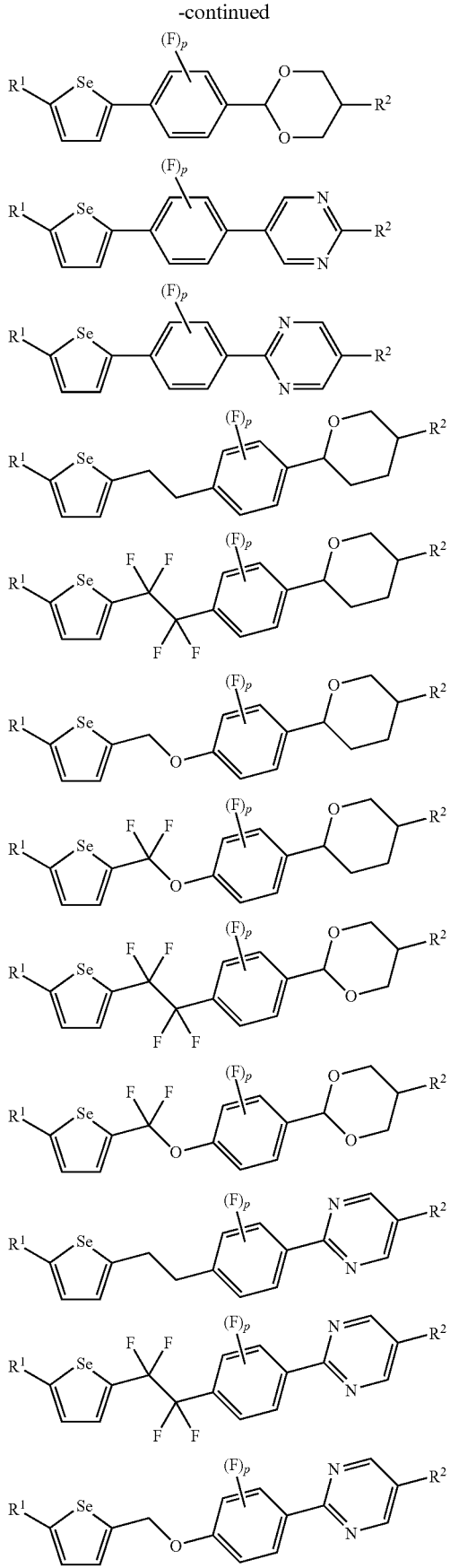

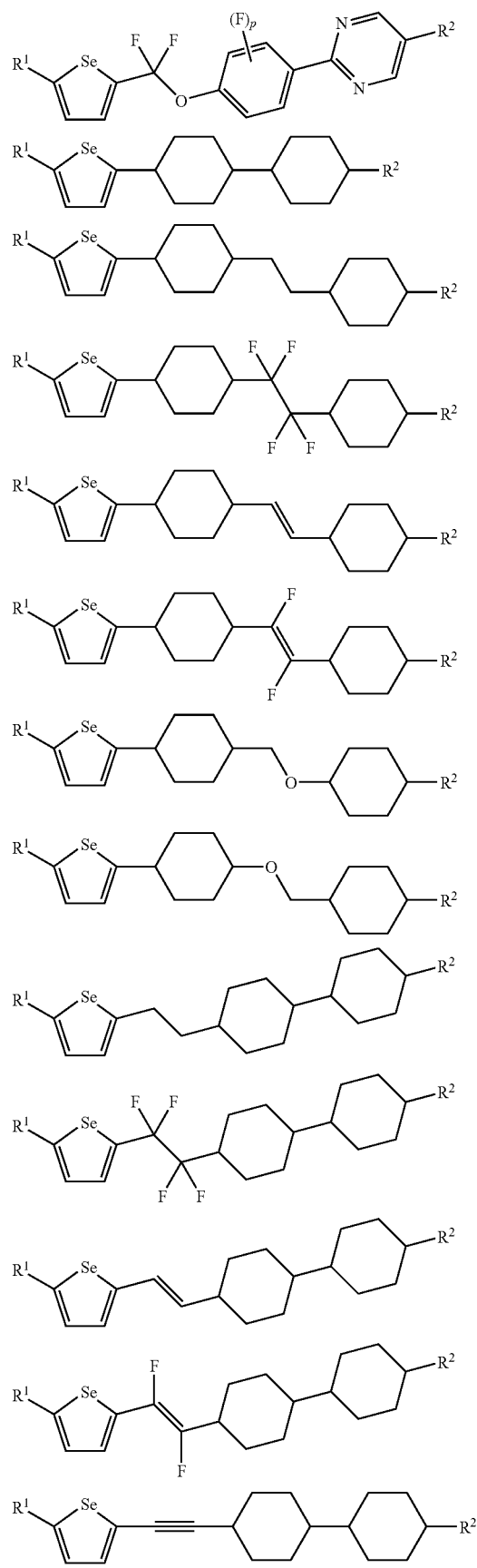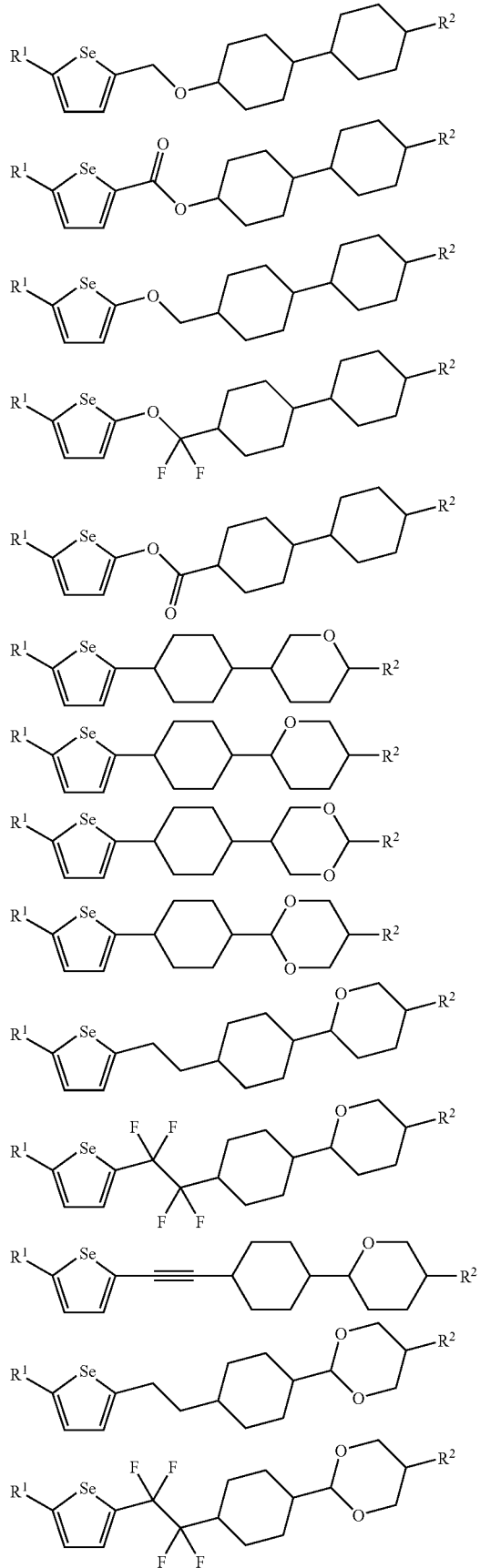

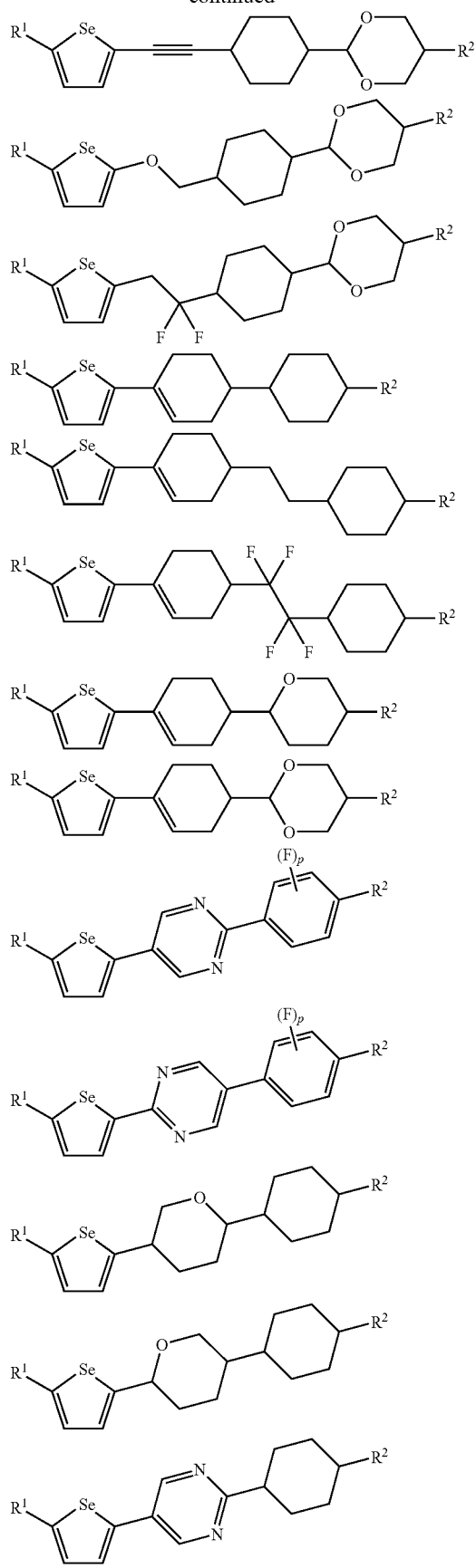
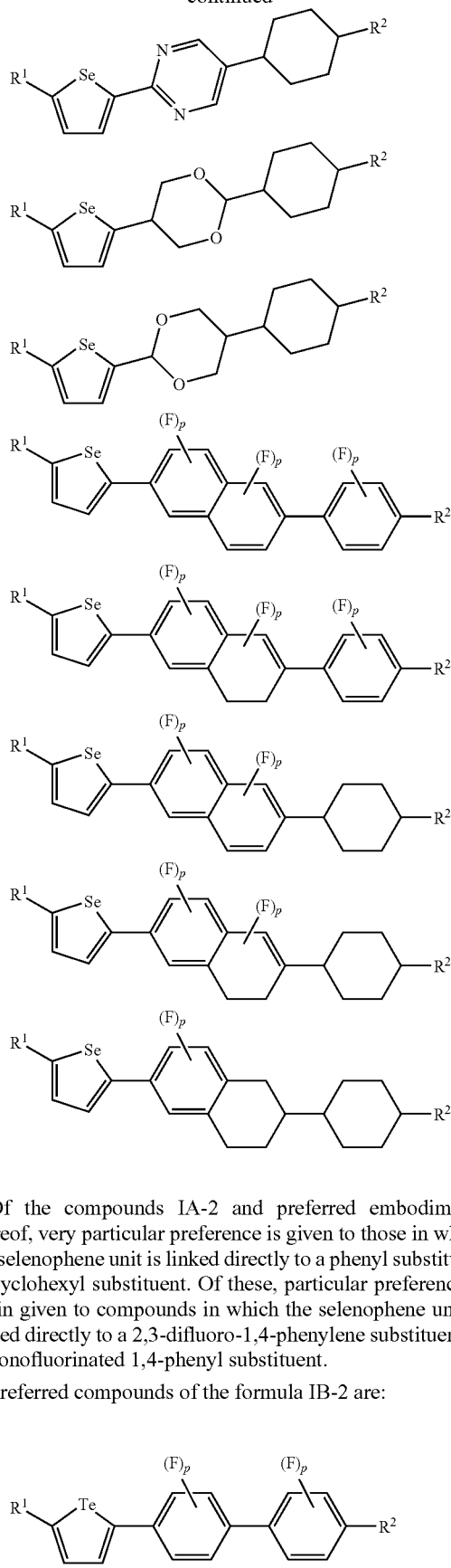

Of the compounds IA-2 and preferred embodiments thereof, very particular preference is given to those in which the selenophene unit is linked directly to a phenyl substituent or cyclohexyl substituent. Of these, particular preference is again given to compounds in which the selenophene unit is linked directly to a 2,3-difluoro-1,4-phenylene substituent or a monofluorinated 1,4-phenyl substituent.

Preferred compounds of the formula IB-2 are:

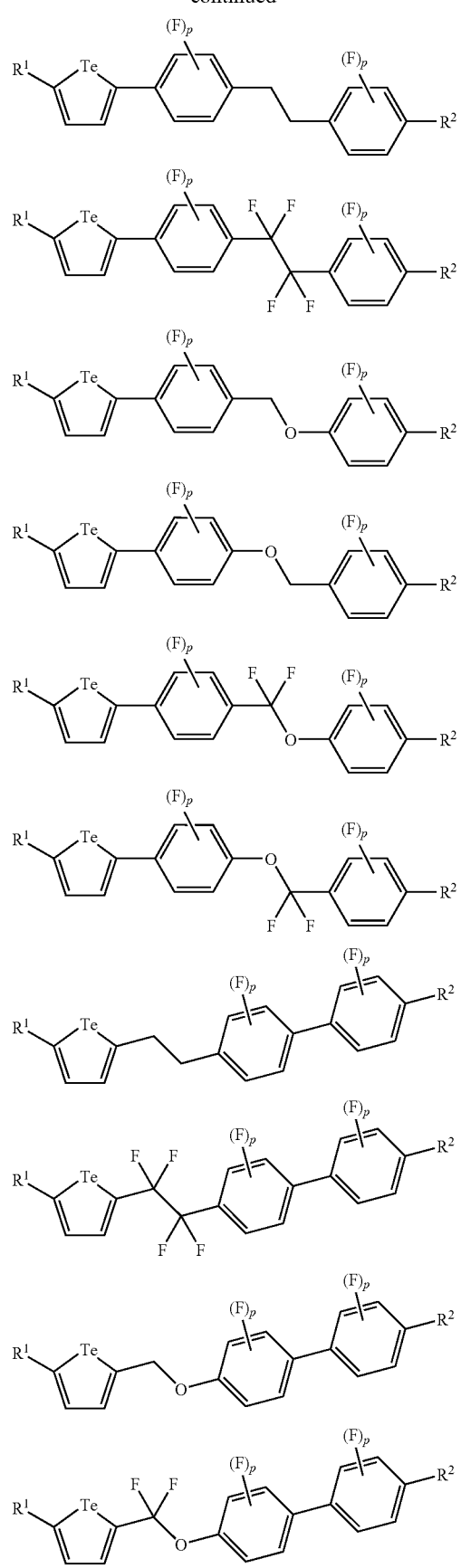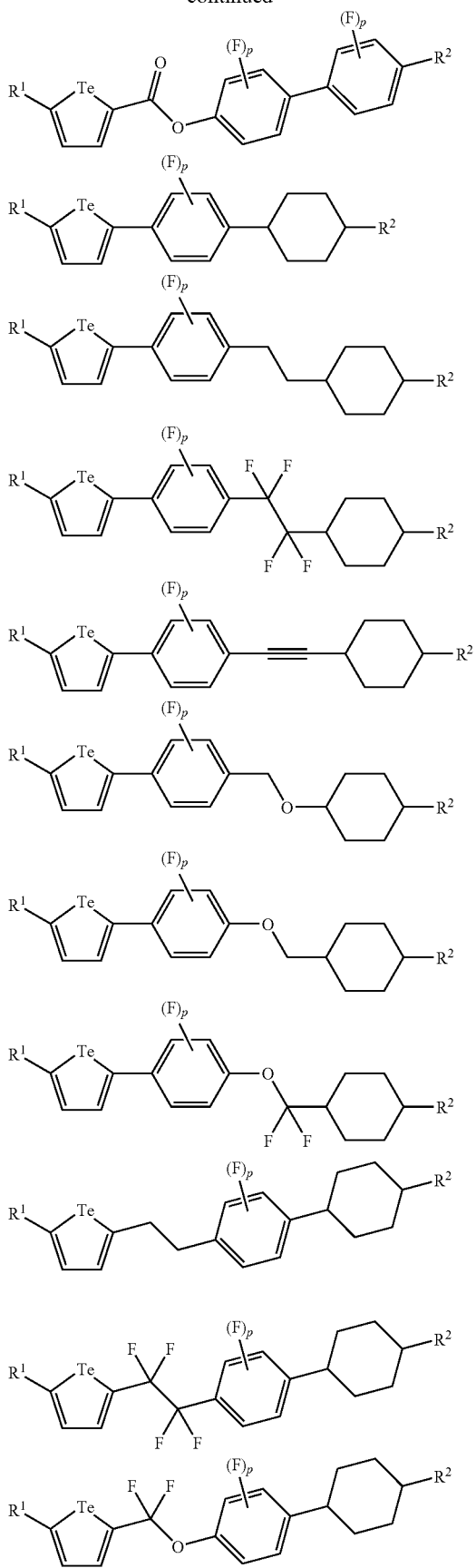

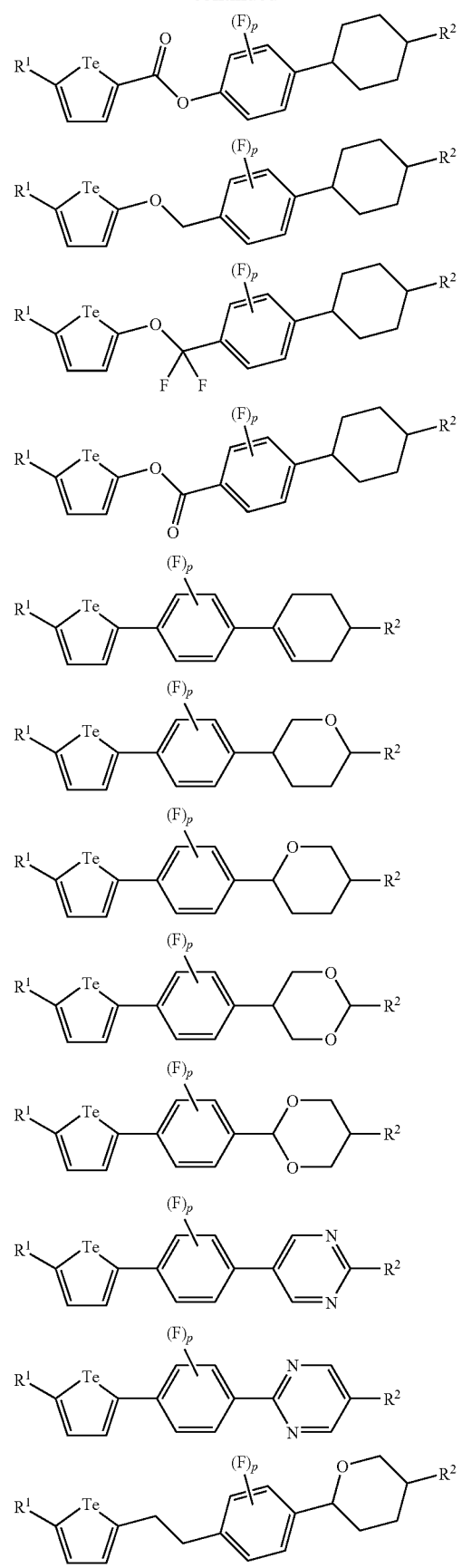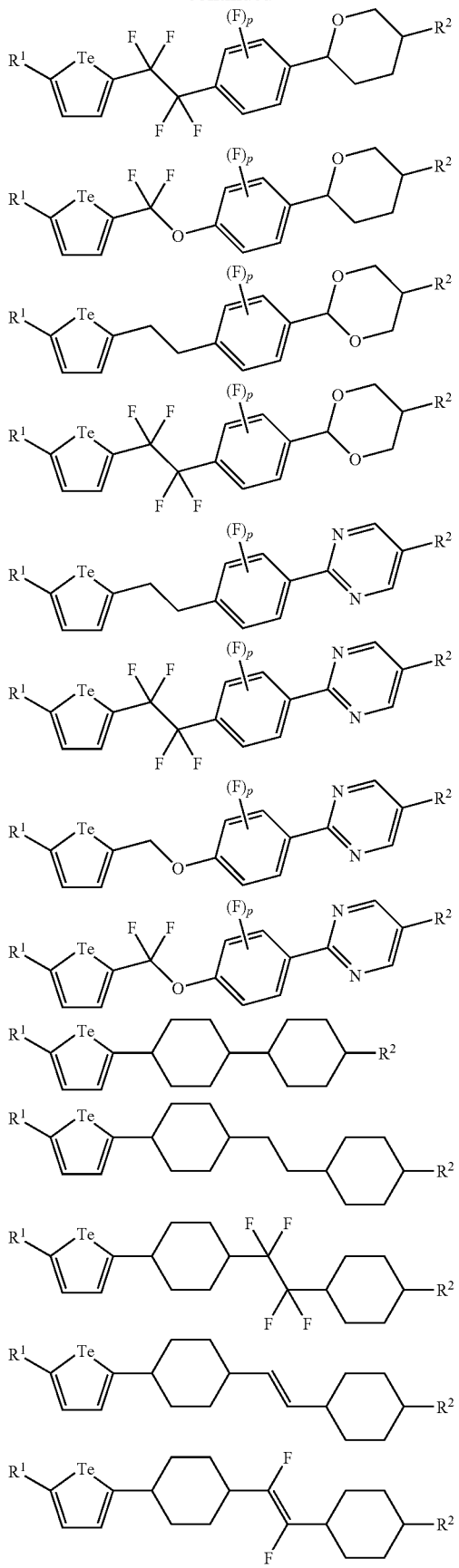

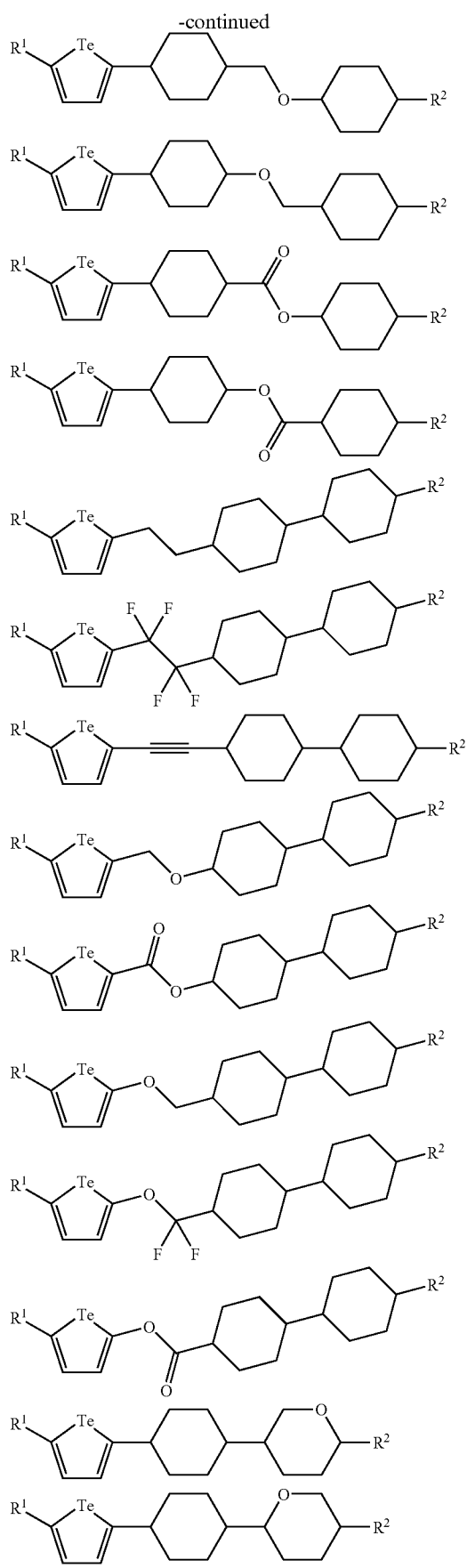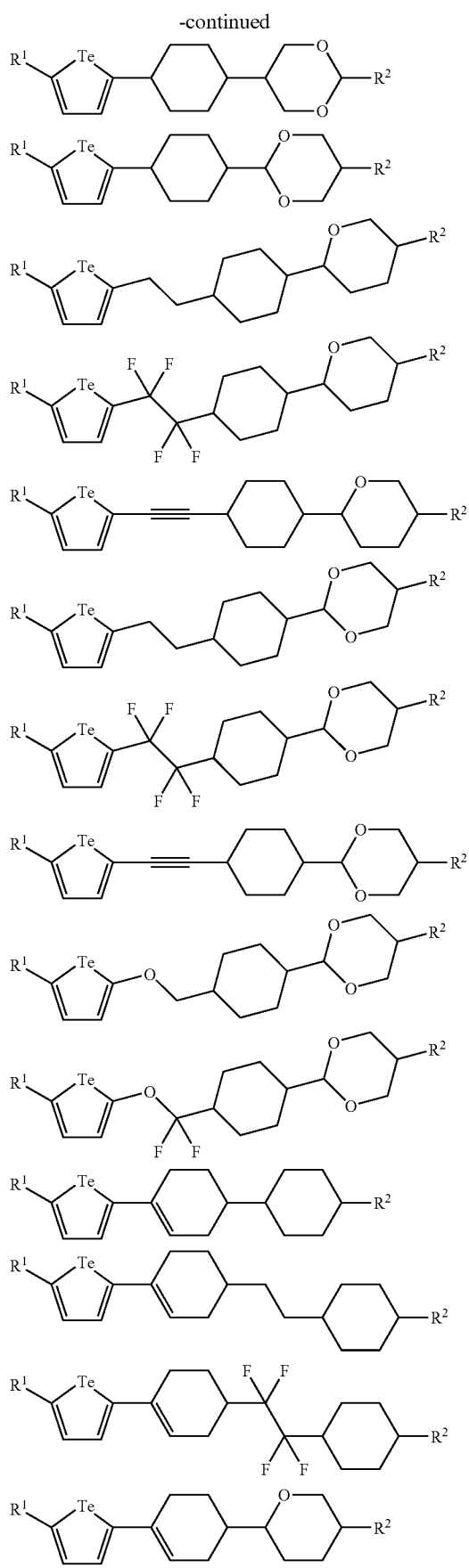

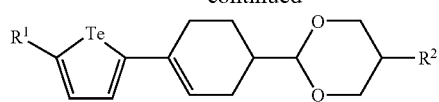
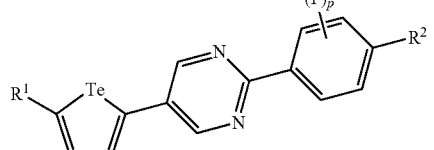
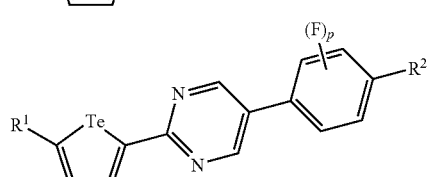
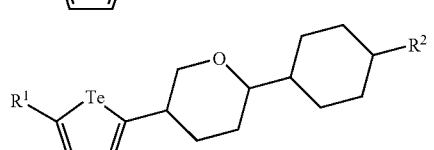
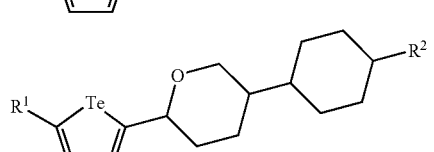
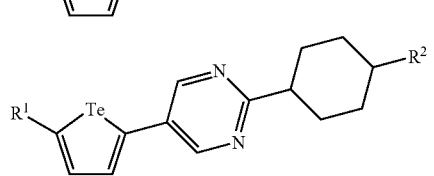
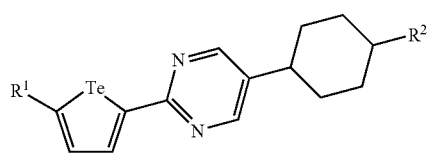
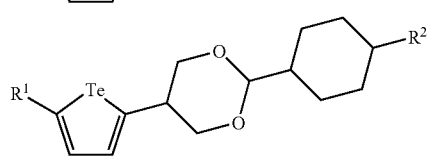
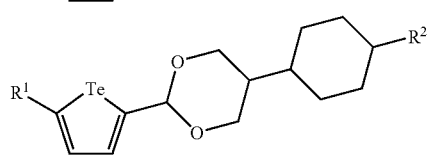
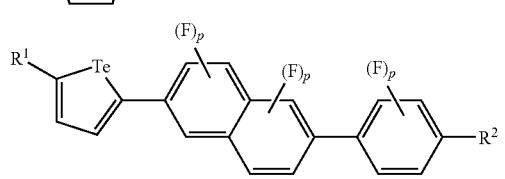
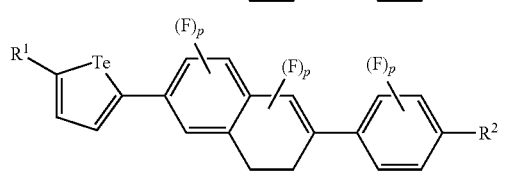
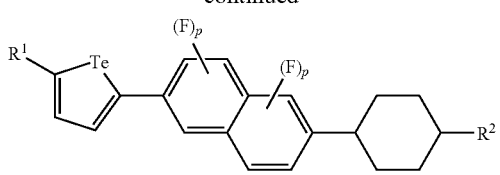
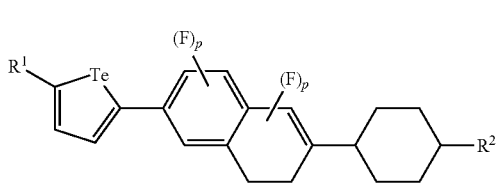
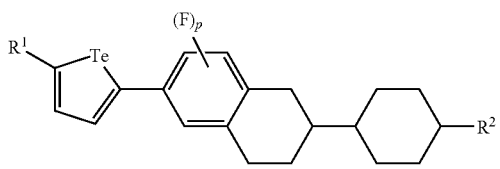
Of the compounds IB-2 and preferred embodiments thereof, very particular preference is given to those in which the tellurophene unit is linked directly to a phenyl substituent or cyclohexyl substituent.
Preferred compounds of the formula IA-9 are:
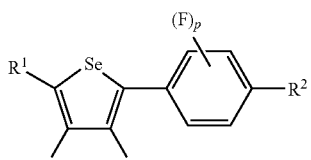
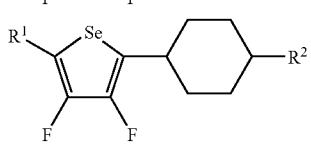
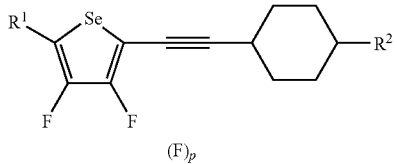
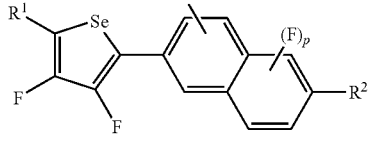
Preferred compounds of the formula IA-10 are:
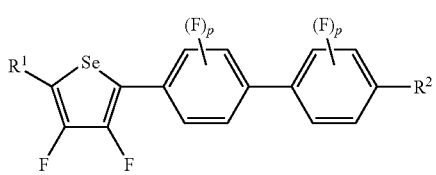

-continued

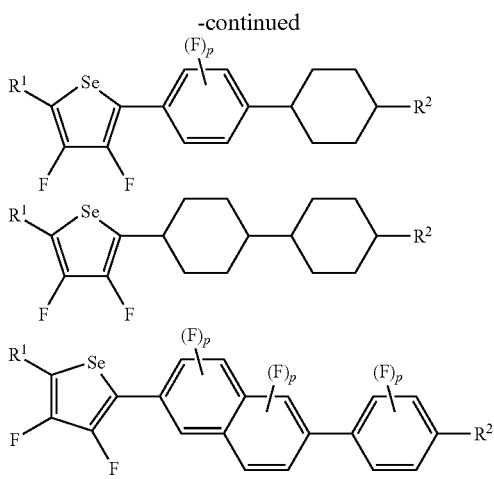

Preferred compounds of the formula IA-11 are:

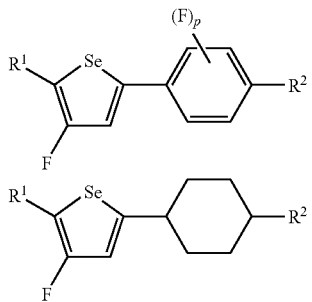

Preferred compounds of the formula IA-12 are:

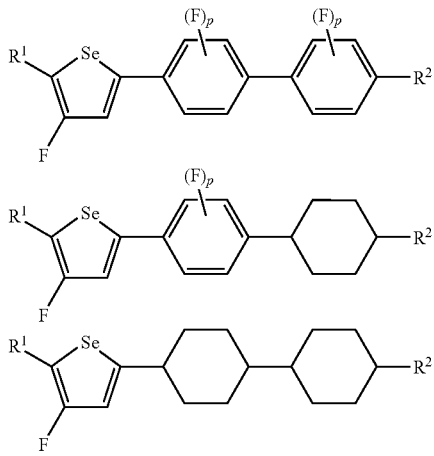

Preferred compounds of the formula IA-13 are:

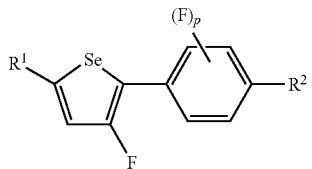

-continued

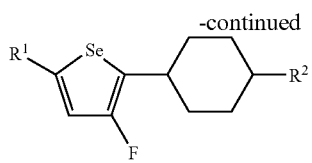

Preferred compounds of the formula IA-14 are:

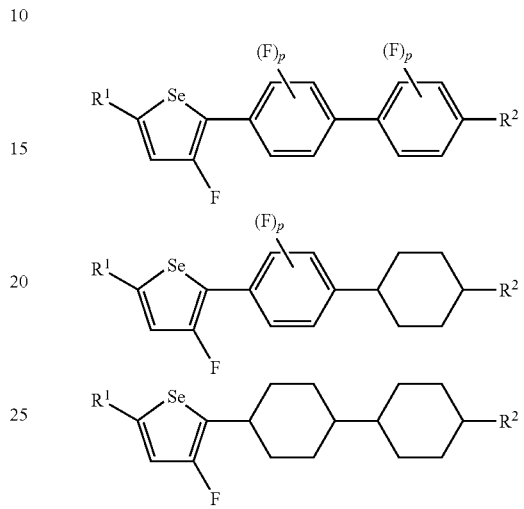

The compounds of the formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail. The compounds of the formula I can advantageously be prepared as can be seen from the following illustrative syntheses (Schemes 1, 2 and Schemes I to XXIII).

Typical for a series of compounds according to the invention is a preparation process for these which comprises a process step in which a 2-bromo- or 2-iodoselenophene compound or a 2-iodo- or 2-bromotellurophene compound is coupled to an arylboronic acid or an arylboronic acid ester (Scheme 1). This possibility opens up for 2-haloselenophene or 2-halotellurophene or for 2-haloselenophenes or 2-halotellurophenes which are additionally substituted in the 5-position by a variable radical.

Scheme 1. Preparation of compounds of the formula I by means of a Suzuki coupling (r = 0, 1, 2).

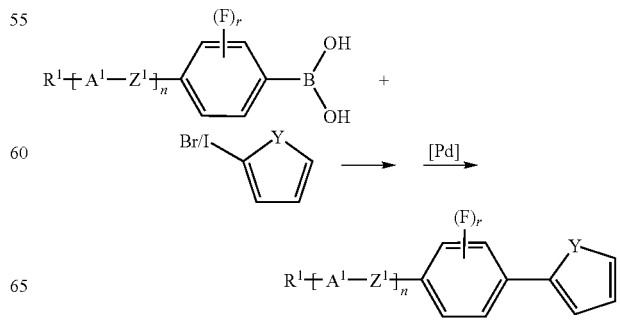

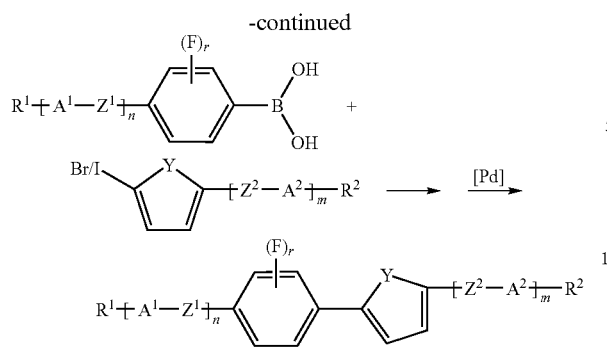

In the former case, the 5-position of the chalcogenophene unit can be further functionalised in a subsequent step by deprotonation or metallation using a strong base and a reaction with suitable electrophiles. In this way, the position is successfully alkylated, for example by addition of butyllithium followed by methyl iodide.

Instead of an alkylating agent, it is also possible to add, for example, N-formylmorpholine or N-formylpiperidine in order to produce an aldehyde.

The aldehyde function is the starting point for a further CC linking reaction by Wittig reaction or the formation of a dioxane ring from a 1,3-diol. Oxidation of the aldehyde function gives access to carboxylic acid derivatives, and reduction equally gives access to ethers of the carbinol formed.

An alternative derivatisation of the heteroaromatic ring is in turn achieved by 1,2-addition of the metallated chalcogenophenes onto substituted cyclohexanones. The further steps are elimination to give the cyclohexene and hydrogenation to give 2-selenophene- or tellurophene-cyclohexane derivatives (Scheme 2). This possibility again arises for selenophene and tellurophene and for chalcogenophene derivatives which are functionalised/substituted in the 5-position.

Scheme 2. Preparation of compounds of the formula I

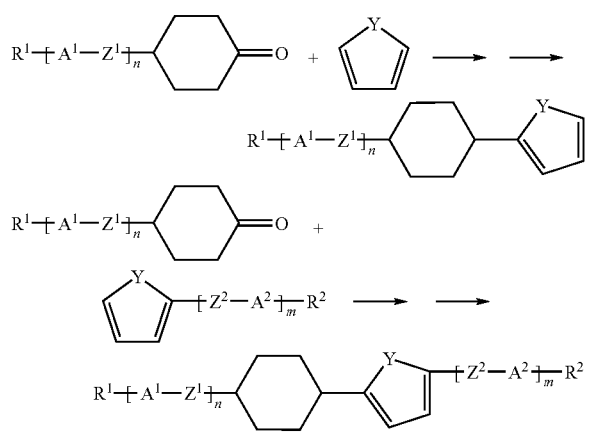

In this way, very different Se- and Te-heteroaromatic derivatives according to the invention are obtained.

The synthesis of compounds according to the invention is explained again below with reference to detailed preparation processes.

The synthesis of the selenophene derivatives (I, Y=Se) and tellurophene derivatives (I, Y=Te) is preferably carried out starting from the 2-halochalcogenophenes 6 (Y=Se, Te and X=Br, I), where 2-bromoselenophene (6, Y=Se, X=Br, $L^1=L^2=H$) and 2-bromotellurophene 6 (Y=Te, X=Br, $L^1=L^2=H$) are particularly preferred starting materials.

Scheme I: Synthesis of 2-haloselenophnes 6 ( Y = Se, X = Br, I) and 2-halotellurophenes 6 (Y = Te, X = Br, I)

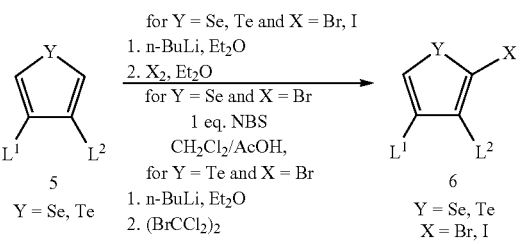

2-Iodoselenophenes (6, Y=Se, X=I) and 2-iodotellurophenes (6, Y=Te, X=I) are formed by metallation of selenophenes (5, Y=Se) and tellurophenes (5, Y=Te) respectively using n-BuLi and reaction of the resultant 2-lithio compounds with iodine [P. Prediger, A. V. Moro, C. W. Nogueira, L. Savegnago, P. H. Menezes, J. B. T. Rocha, G. Zeni, *J. Org. Chem.* 2006, 71, 3786-3792 and K. Takahashi, S. Tarutani, *Heterocycles* 1996, 43, 1927-1935]. 2-Bromoselenophenes (6, Y=Se, X=Br) and 2-bromo-tellurophenes (6, Y=Te, X=Br) are obtained in conceptionally the same way. Alternatively, the bromination of selenophenes (5, Y=Se) can be carried out using NBS [J. Nakayama, H. Dong, K. Sawada, A. Ishii, S. Kamakura, *Tetrahedron* 1996, 52, 471-488] and the bromination of 2-lithio-tellurophenes can be carried out using 1,2-dibromo-1,1,2,2-tetrachloroethane (cf. Scheme I) [R. B. Panatieri, J. S. Reis, L. P. Borges, C. W. Nogueira, G. Zeni, *Synlett* 2006, 3161-3163 and S. Inoue, T. Jigami, H. Nozoe, Y. Aso, F. Ogura, T. Otsubao, *Heterocycles* 2000, 52, 159-170]. Selenophene (5, Y=Se, $L^1=L^2=H$) is commercially available, tellurophene (5, Y=Te, $L^1=L^2=H$) is prepared as described in the literature [T. J. Barton, R. W. Roth, *J. Organomet. Chem.* 1972, 39, C66-C68 and W. Lohner, K. Praefcke, *Chem. Ber.* 1978, 111, 3745-3746].

Transition metal-mediated cross-couplings of the 2-halochalcogenophenes 6 (Y=Se, Te and X=Br, I), for example using arylboronic acids 7 (Suzuki coupling) [P. Prediger, A. V. Moro, C. W. Nogueira, L. Savegnago, P. H. Menezes, J. B. T. Rocha, G. Zeni, *J. Org. Chem.* 2006, 71, 3786-3792], terminal alkynes 9 (Sonogashira coupling), Grignard reagents 11 (Kumada coupling), alkenylboronic acids 13 [C. Sun, R. Bittman, *J. Org. Chem.* 2006, 71, 2200-2202 and A. Torrado, S. Lopez, R. Alvarez, A. R. de Lera, *Synthesis* 1995, 285-293], organozinc reagents 15 (Negishi coupling) or alkenes 16 (Heck coupling) [*Metal-Catalyzed Cross-Coupling Reactions* (Eds.: A. de Meijre, F. Diederich), Wiley-VCH, Weinheim, 2nd Edn. 2004] (cf. Scheme II), are particularly preferred methods of obtaining functionalised selenophene derivatives 8, 12 and 14 (Y=Se) and tellurophene derivatives 8, 12 and 14 (Y=Te). The requisite coupling partners 7, 9, 11, 13, 15 and 16 are either commercially available or can be prepared by known methods [*Methoden der organischen Chemie* (*Methods of Organic Chemistry*) (Houben-Weyl), Georg Thieme Verlag, Stuttgart, New York, 4th Edn. 1993].

Scheme II: Functionalized 2-selenophene derivatives 8, 12 and 14 (Y = Se) and 2-tellurophene derivatives 8, 12 and 14 (Y = Te) from transition metal-mediated cross-couplings
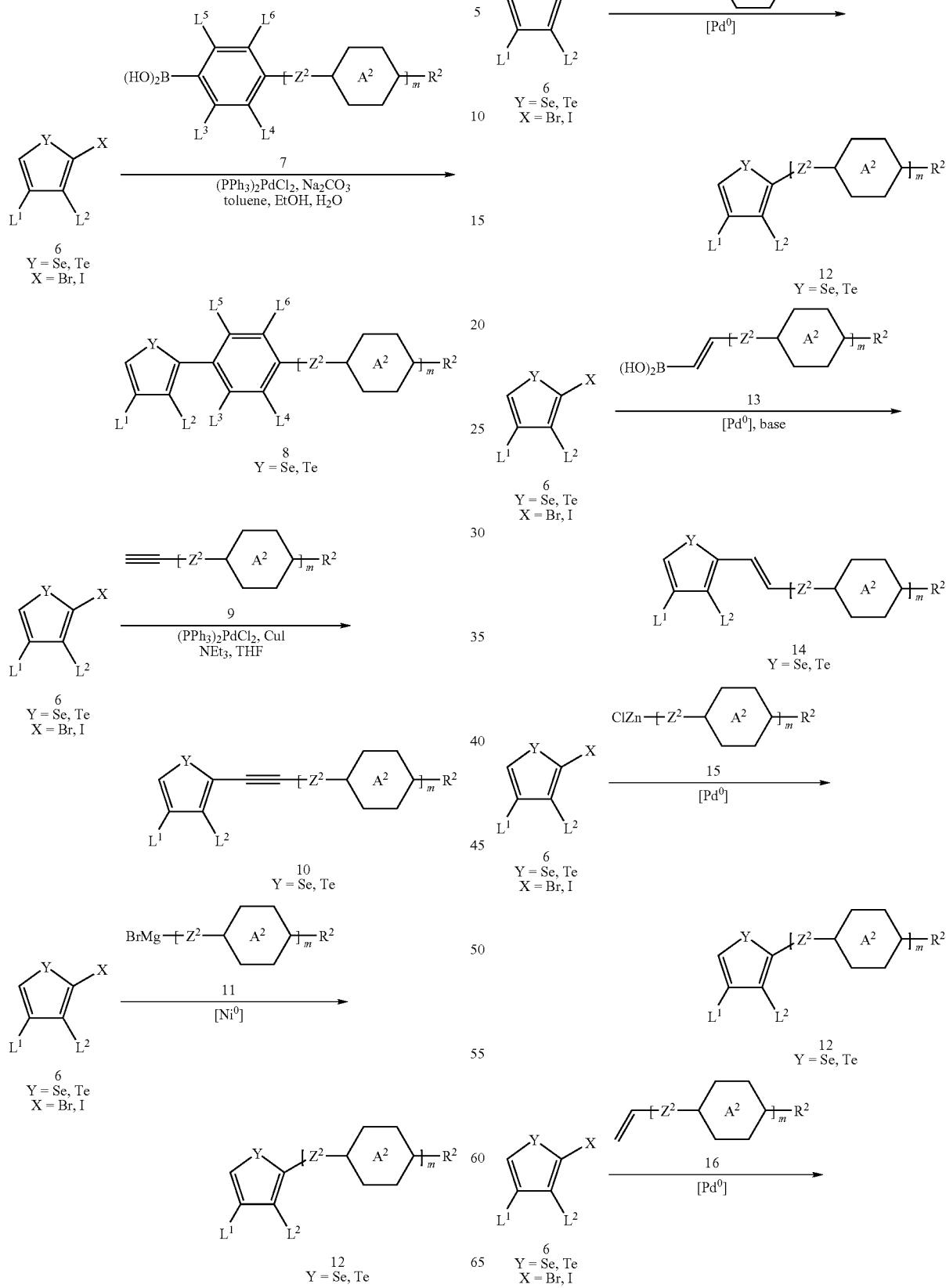

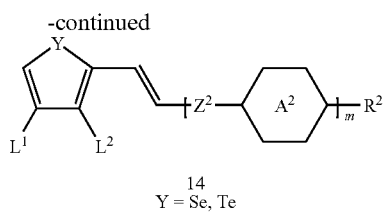

14
Y = Se, Te

The invention therefore furthermore also relates to a process for the preparation of compounds of the formula I comprising reaction of a 2-bromo- or 2-iodoselenophene compound or a 2-iodo- or 2-bromotellurophene compound with an aryl- or alkenylboronic acid, an aryl- or alkenylboronic acid ester, a terminal alkyne, a terminal alkene or an organomagnesium or organozinc compound. The reaction is generally carried out in the presence of a transition-metal compound. In this connection, the reaction means in the narrower sense a coupling or a C—C linking reaction. The transition-metal compound is preferably employed as catalyst. The catalyst can also be generated in situ by adding suitable precursors of the catalyst (procatalysts) to the reaction. Preferred transition metals are Pd, Ni, Cu and Fe. The transition metals which are suitable for the individual reactions and the transition-metal complexes specifically used are also evident from the schemes or the cited literature.

Furthermore, metallation of chalcogenophene derivatives 6 (Y═Se, Te; X═H) or halogen-metal exchange reactions on 2-halochalcogenophene derivatives 6 (Y═Se, Te; X═Br, I) and optionally trans-metallation using, for example, zinc halides gives, inter alia, the chalcogenophene-metal compounds 17 (Y═Se, Te, M=Li, Na, K, MgX, Mg$_{1/2}$, ZnX, Zn$_{1/2}$) (cf. Scheme III), which can be converted in a versatile manner into further novel synthetic building blocks [*Methoden der organischen Chemie* (*Methods of Organic Chemistry*) (Houben-Weyl), Georg Thieme Verlag, Stuttgart, N.Y., 4th Edn. 1993].

Scheme III: Chalcogenophene-metal compounds 17 (Y = Se, Te)

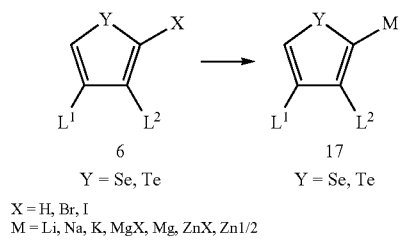

6
Y = Se, Te
X = H, Br, I

17
Y = Se, Te
M = Li, Na, K, MgX, Mg, Zn X, Zn1/2

The further functionalisation of the remaining 5-position of the selenophenes 8, 12 and 14 (Y═Se) and tellurophenes 8, 12 and 14 (Y═Te) is again carried out via halogen compounds 18 (Y═Se, Te and X═Br, I; X═Br is preferred). The halogenation is carried out as above (cf. Scheme IV). If A$^2$ represents one (or more) mono- or polyfluorinated 1,4-phenylene group(s), metallation using LiTMP as base is preferred.

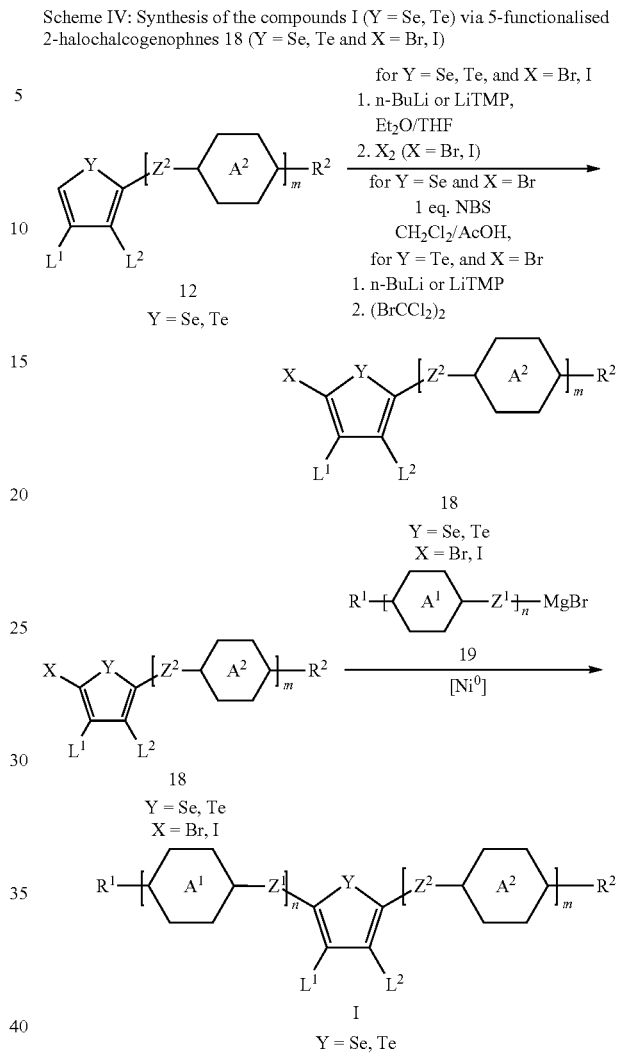

The 5-functionalised 2-halochalcogenophenes 18 (Y═Se, Te and X═Br, I) can then again be converted into the desired compounds of the formula I (Y═Se, Te) via conventional cross-coupling processes (cf. Scheme II) [*Metal-Catalyzed Cross-Coupling Reactions* (Eds.: A. de Meijre, F. Diederich) Wiley-VCH, Weinheim, 2nd Edn. 2004]. Scheme IV shows by way of example the conversion of the compounds 18 (Y═Se, Te and X═Br, I) into the target compounds of the formula I (Y═Se, Te) via a Kumada coupling using the Grignard reagents 19. Further particularly preferred processes are Suzuki couplings, Sonogashira couplings [*Metal-Catalyzed Cross-Coupling Reactions* (Eds.: A. de Meijre, F. Diederich), Wiley-VCH, Weinheim, 2nd Edn. 2004] and couplings using alkenylboronic acids [C. Sun, R. Bittman, *J. Org. Chem.* 2006, 71, 2200-2202 and A. Torrado, S. Lopez, R. Alvarez, A. R. de Lera, *Synthesis* 1995, 285-293] (cf. also Scheme II).

Furthermore, as already also described above, for example, metallation of chalcogenophene derivatives 20 (Y═Se, Te; X═H) or halogen-metal exchange reactions on 2-halochalcogenophene derivatives 20 (Y═Se, Te; X═Br, I) and optionally trans-metallation using, for example, zinc halides gives, inter alia, the chalcogenophene-metal compounds 21 (Y═Se, Te, M=Li, Na, K, MgX, Mg, ZnX, Zn$_{1/2}$) (cf.

Scheme V), which can be converted in a versatile manner into further novel synthetic building blocks [*Methoden der organischen Chemie* (*Methods of Organic Chemistry*) (Houben-Weyl), Georg Thieme Verlag, Stuttgart, N.Y., 4th Edn. 1993].

Scheme V: Chalcogenophene-metal compounds 21 (Y = Se, Te)

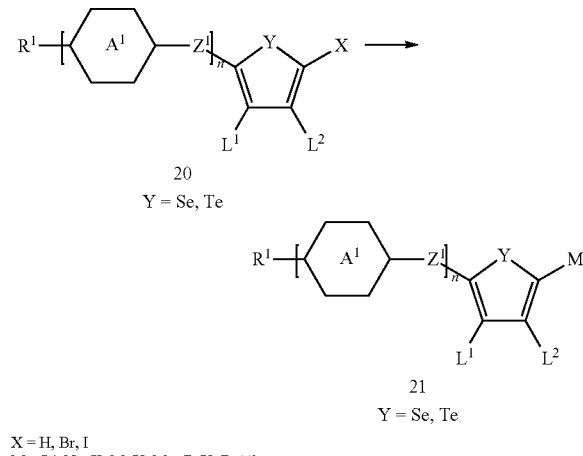

20
Y = Se, Te

21
Y = Se, Te

X = H, Br, I
M = Li, Na, K, MgX, Mg, ZnX, Zn1/2

Compounds I (Y=Se, Te) in which an $R^1$-$A^1$-$Z^1$ or $R^2$-$A^2$-$Z^2$ group represents an alkenyl or alkyl radical, or $Z^1$ and/or $Z^2$ represent alkenyl or alkyl bridges are particularly preferred. A process which includes the reduction of 2-ketoselenophene intermediates has already been published [Y. K. Yur'ew, N. K. Sadovaya, *J. Gen. Chem. USSR* 1961, 31, 3296-3297]. According to the synthesis in Scheme IV and the methods from Scheme II, these substances can preferably also be prepared via transition metal-mediated coupling of the compounds 6 and 18 (Y=Se, Te and X=Br, I) using alkenylboronic acids or alkylmagnesium reagents. If, as shown in Scheme II, alkynes are used as coupling partner, the products 10 (Y=Se, Te) or I (Y=Se, Te and $Z^{1,2}$=C≡C) can be converted into these particularly preferred compounds by suitable hydrogenations.

Furthermore, an alkylation of the 2-lithio compounds obtained from the compounds 22 (Y=Se, Te) using, for example, alkyl halides (23, X=Br, I) can be carried out (cf. Scheme VI). The latter method is particularly preferred for strong alkylating agents 23 (X=Br, I), particularly preferably for compounds I (Y=Se, Te) in which an $R^1$-$A^1$-$Z^1$ or $R^2$-$A^2$-$Z^2$ group is intended to represent a methyl radical.

Scheme VI: Alkylation of 2-lithiochalcogenophne derivatives using alkyl halides 23 (X = Br, I)

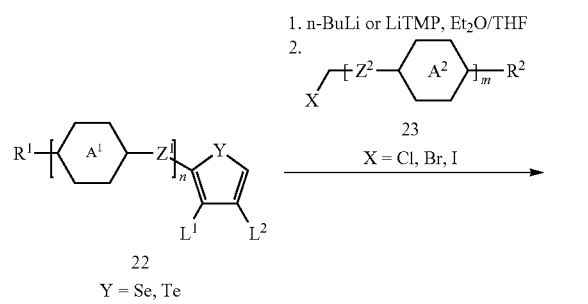

22
Y = Se, Te

24
Y = Se, Te

A particularly preferred process for the synthesis of the compounds I (Y=Se, Te) in which an $R^1$-$A^1$-$Z^1$ Z or $R^2$-$A^2$-$Z^2$ group represents an alkenyl or alkyl radical or $Z^1$ and/or $Z^2$ represents alkenyl or alkyl bridges uses 2-formylchalcogenophene derivatives 25 (Y=Se, Te) as intermediates, or 2-formylselenophene (25, Y=Se, n=0, $R^1$=H and $L^1$=$L^2$=H) and 2-formyltellurophene (25, Y=Te, n=0, $R^1$=H and $L^1$=$L^2$=H) as starting materials.

These are prepared by metallation of chalcogenophene derivatives 22 (Y=Se, Te) (or selenophene (22, Y=Se, n=0 and $R^1$=H, $L^1$=$L^2$=H) or tellurophene (22, Y=Te, n=0 and $R^1$=H, $L^1$=$L^2$=H)) and formylation of the corresponding lithio compounds using N-formylmorpholine (cf. Scheme VII). If $A^1$ represents one (or more) mono- or polyfluorinated 1,4-phenylene group(s), metallation using LiTMP as base is preferred. Alternatively, the formylation can also be carried out via the Vilsmayer-Haack reaction.

Scheme VII: Preparation of the 2-formylchalcogenophene derivatives 25 (Y = Se, Te)

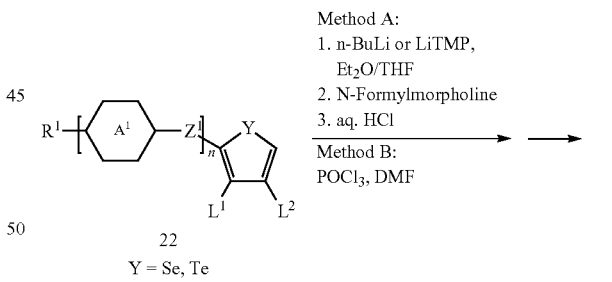

22
Y = Se, Te

Method A:
1. n-BuLi or LiTMP, Et$_2$O/THF
2. N-Formylmorpholine
3. aq. HCl

Method B:
POCl$_3$, DMF

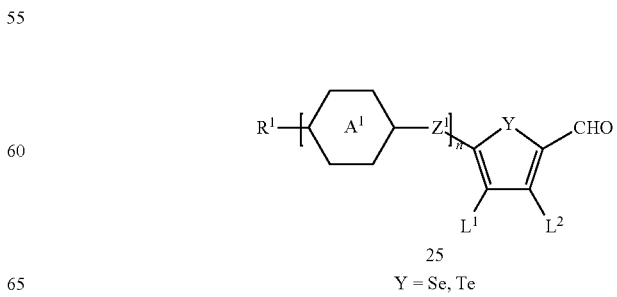

25
Y = Se, Te

Scheme VIII: Functionalisation of 2-formylchalcogenophene derivatives 25 (Y = Se, Te) by Witting olefination

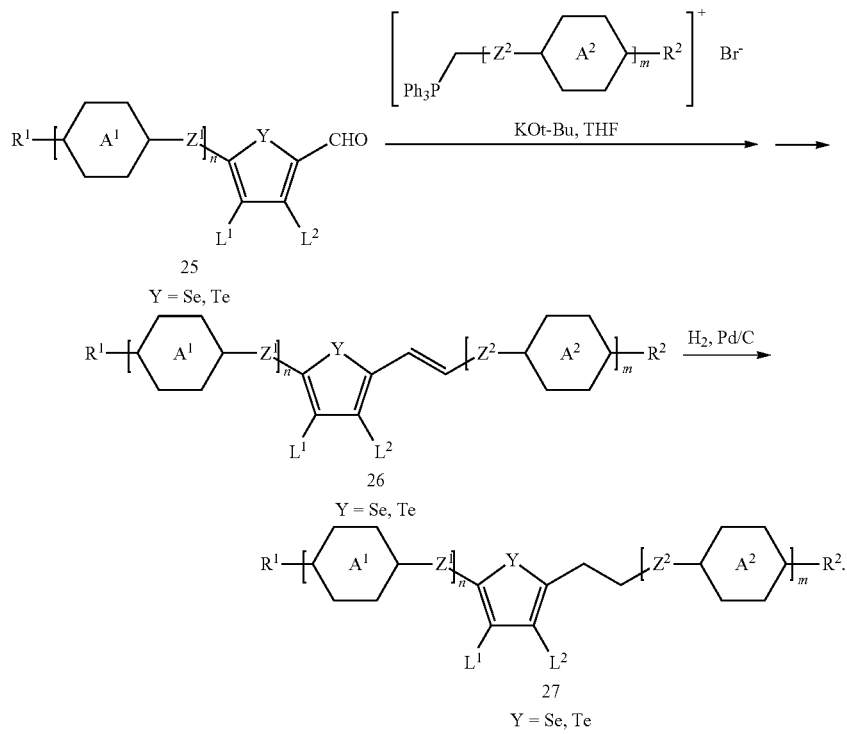

A particularly preferred way of further functionalisation of the 2-formylchalcogenophene derivatives 25 (Y=Se, Te) is the Wittig olefination (cf. Scheme VIII). This gives the corresponding compounds 26 (Y=Se, Te) containing alkenyl bridges or alkenyl radicals (m=0), which can be hydrogenated further to give the very particularly preferred compounds 27 (Y=Se, Te) containing alkyl bridges or alkyl radicals (m=0).

A preferred additional way of functionalisation of the 2-formylchalcogenophene derivatives 25 (Y=Se, Te) consists in the reaction with Grignard or organolithium reagents. The resultant alcohols 28 (Y=Se, Te) can then be converted, for example in an ionic reduction, into compounds of type 24 (Y=Se, Te) (cf. Scheme IX).

Scheme IX: Functionalisation of 2-formylchalcogenophene derivatives 25 (Y = Se, Te) by 1, 2-addition of Grignard or organolithium reagents

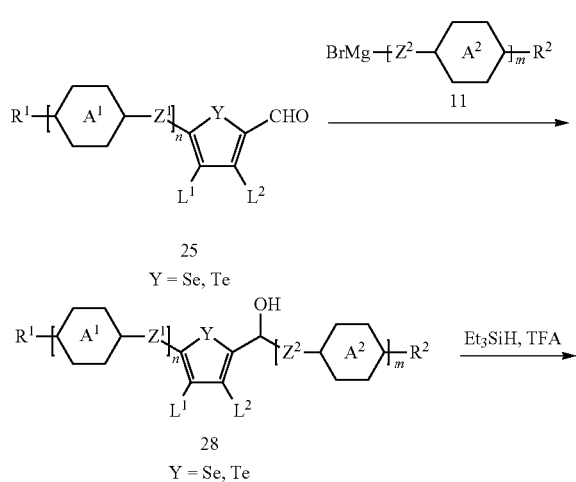

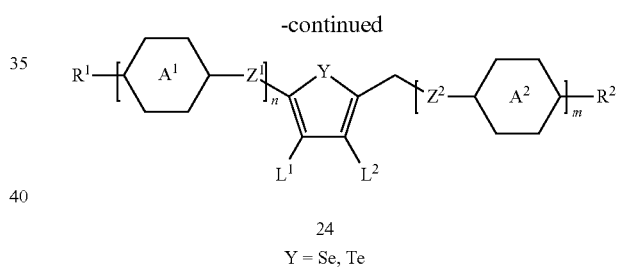

-continued

The possibilities described for the functionalisation of the 2- and 5-position of the selenophenes or tellurophenes via lithiated (generally metallated), brominated or formylated intermediates can be combined as desired. Thus, 2-formylselenophenes (29, Y=Se) [Y. K. Yur'ew, Saizewa; *J. Gen. Chem. USSR* 1958; 28, 2203-2205 and Y. K. Yur'ew, Saizewa; *J. Gen. Chem. USSR* 1959; 29, 3644-3645 and P. Chierici; *Gazz. Chim. Ital.;* 1958, 88; 453-455] and 2-formyltellurophenes (29, Y=Te) [D. Catalano, A. M. Caporusso, F. Da Settimo, C. Forte, C. A. Veracini, *Gazz. Chim. Ital.* 1988; 118, 529-532] are also suitable starting materials for the synthesis of the target compounds I (Y=Se, Te) (cf. Scheme X).

Scheme X: Synthesis of the compounds I (Y = Se, Te) starting from 2-formylchalcogenophenes 29 (Y = Se, Te)

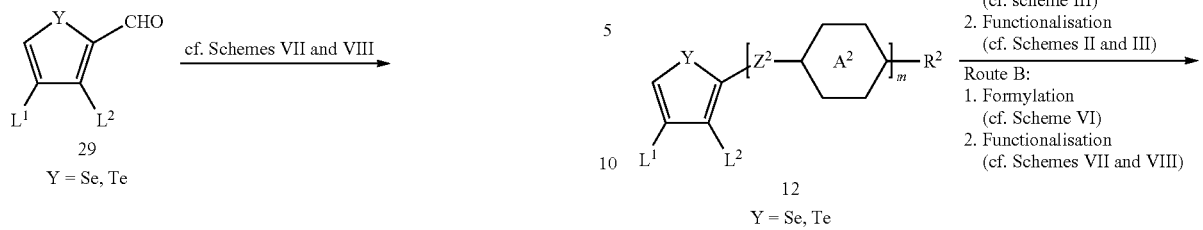

Scheme XI: Synthesis of the compounds I (Y = Se, Te) starting from 2-halochalcogenophenes 6 (Y = Se, Te)

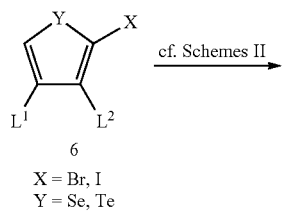

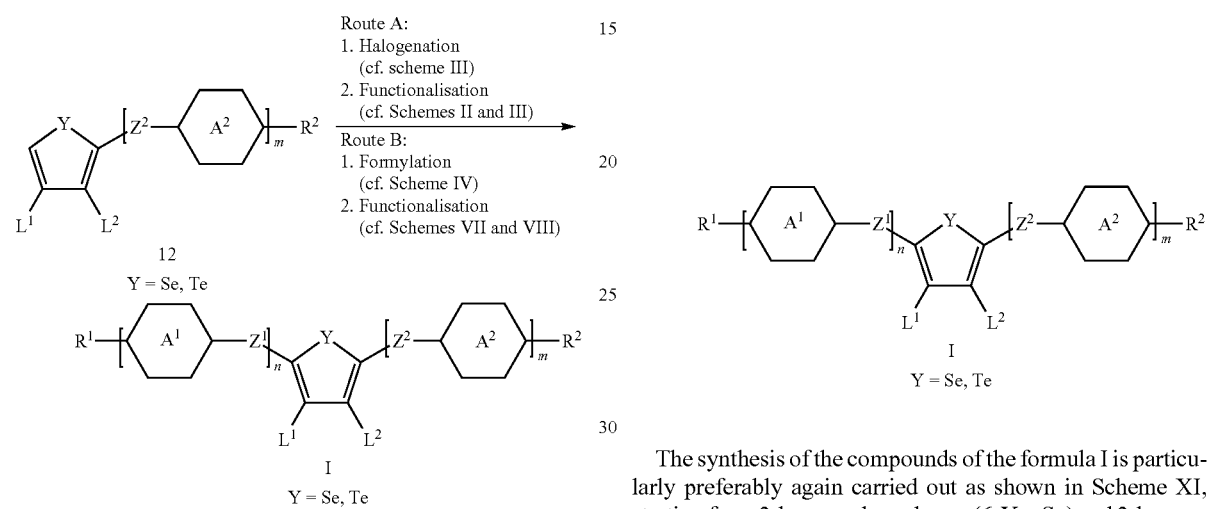

The synthesis of the compounds of the formula I is particularly preferably again carried out as shown in Scheme XI, starting from 2-bromoselenophenes (6, Y=Se) and 2-bromotellurophenes (6, Y=Te). The subsequent functionalisation of the intermediates 12 (Y=Se, Te) is particularly preferably carried out via a formylation (route B in Scheme XI).

Particularly preferred embodiments of the compounds I (Y=Se, Te) are those in which $Z^1$-$A^1$ and/or $Z^2$-$A^2$ represents a cyclohexyl or cyclohexenyl substituent. For the synthesis of these compounds 33 (Y=Se, Te) and 32 (Y=Se, Te), the 2-lithio compounds 21 (Y=Se, Te, M=Li) are added onto corresponding cyclohexyl ketones 30. After elimination, the resultant alcohols 31 (Y=Se, Te) give the compounds 32 (Y=Se, Te) containing cyclohexenyl substituents, which can then be hydrogenated to give cyclohexane derivatives 33 (Y=Se, Te) (cf. Scheme XII).

Scheme XII: Synthesis of the compounds I (Y = Se, Te) containing cyclohexenyl and cyclohexyl substituents

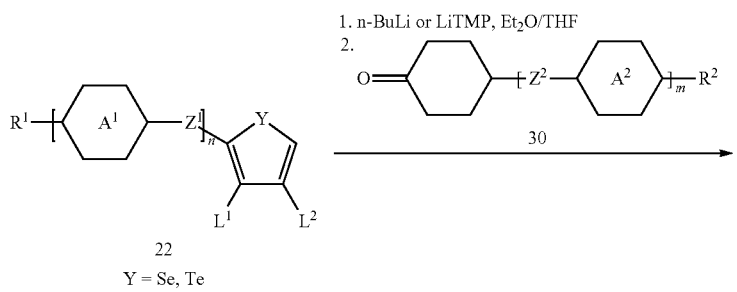

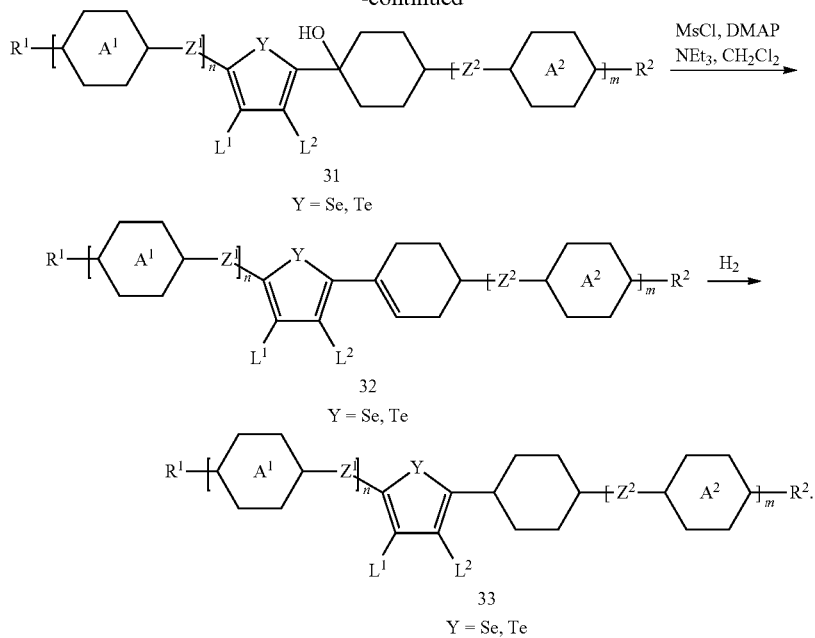

31
Y = Se, Te

32
Y = Se, Te

33
Y = Se, Te

A further particularly preferred method for the synthesis of compounds I (Y=Se, Te) in which $Z^1$-$A^1$ and/or $Z^2$-$A^2$ represents a cyclohexyl radical is the Kumada coupling of substituted or unsubstituted chalcogenophene halides (compounds 6 and 18) using cyclohexyl-Grignard reagents (generally compounds II and 19 respectively) (cf. Scheme II and Scheme IV).

Scheme XIII: Compounds I (Y = Se, Te) containing methyleneoxy bridges

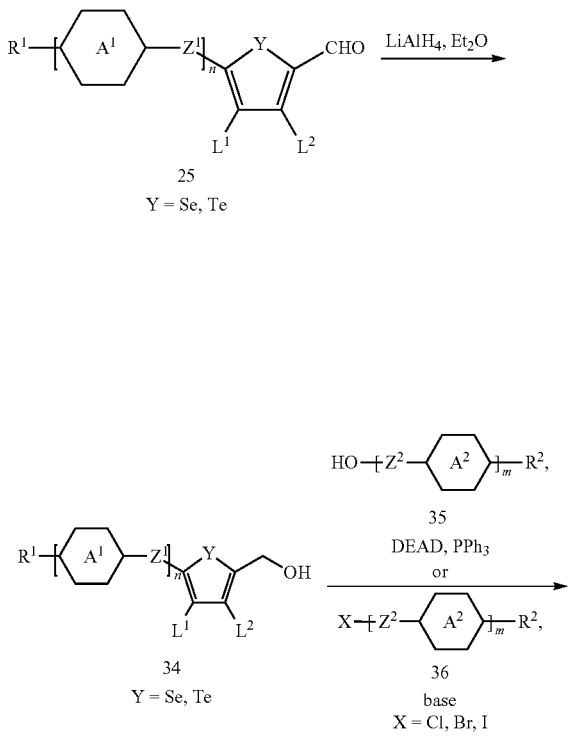

25
Y = Se, Te

34
Y = Se, Te

35

36
base
X = Cl, Br, I

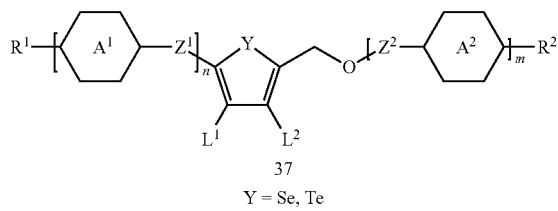

37
Y = Se, Te

In a further preferred embodiment of the compounds I (Y=Se, Te), the selenophene or tellurophene unit is linked to further $R^2$-A2-$Z^2$ or $R^1$-$A^1$-$Z^1$ groups in the 2-position (and/or 5-position) via one (or two) methyleneoxy group(s). Key compounds for the synthesis of these compounds 37 (Y=Se, Te) are the alcohols 34 (Y=Se, Te), which are obtained by reduction of 2-formylchalcogenophenes 25 (Y=Se, Te) [S. Iwatsuki, M. Kubo, N. Kamei, *Chem. Lett.* 1992, 1551-1554]. The alcohols 34 (Y=Se, Te) can then be etherified by suitable methods [*Organikum* (*Practical Organic Chemistry*), Wiley-VCH, Weinheim, 21st Edn. 2001]. Very particular preference is given to etherification using phenol derivatives, for example via a Mitsunobu reaction [O. Mitsunobu, *Synthesis* 1981, 1], or using alkyl halides (X=Cl, Br, I) with addition of base (cf. Scheme XIII).

The alcohol intermediates 34 (Y=Se, Te) can also be converted, for example, into compounds of the formula I (Y=Se, Te) containing polymerisable groups $R^2$-$A^2$-$Z^2$, for example of the particularly preferred acrylate type (cf. Scheme XIV).

Scheme XIV: Compounds I ( Y = Se, Te) containing polymerisable groups of the acrylate type

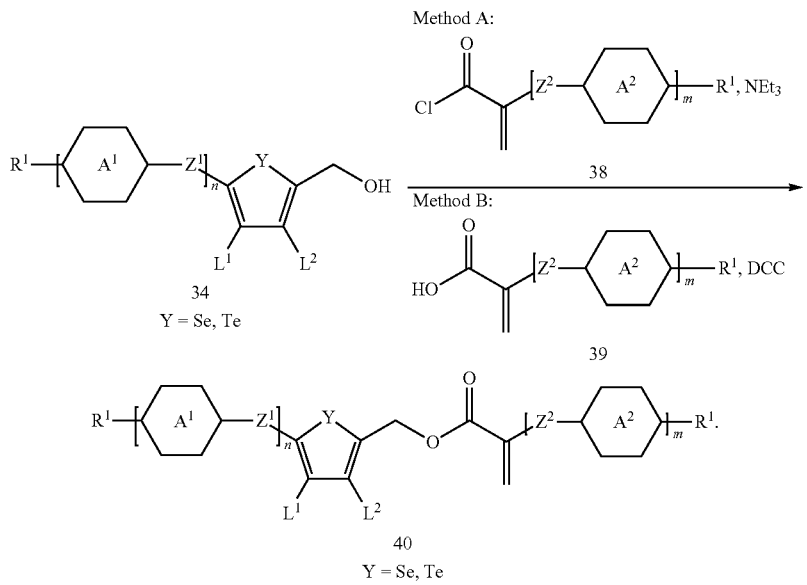

In a particularly preferred embodiment of the compounds I (Y═Se, Te), the selenophene or tellurophene unit is linked to further $R^2$-$A^2$-$Z^2$ or $R^1$-$A^1$-$Z^1$ groups in the 2-position (and/or 5-position) via one (or two) difluoromethyleneoxy group(s). To this end, the lithio compounds produced from 22 (Y═Se, Te) are reacted with dibromodifluoromethane. The resultant compounds 41 (Y═Se, Te) can then be etherified using suitable alcohols 35, in particular phenols 35, to give the compounds 42 (Y═Se, Te) (cf. Scheme XV).

Scheme XV: Compounds I (Y = Se, Te) containing difluoromethyleneoxy bridges

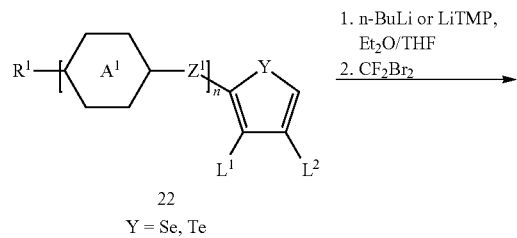

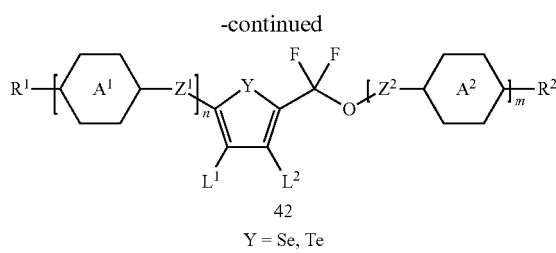

In a preferred embodiment of the compounds I (Y═Se, Te), the selenophene or tellurophene unit is linked to further $R^2$-$A^2$-$Z^2$ or $R^1$-$A^1$-$Z^1$ groups in the 2-position (and/or 5-position) via one (or two) ester groups (for example compounds 44). The carboxylic acids 43 (Y═Se, Te) required for the synthesis are obtained by reaction of the lithio compounds obtained from the compounds 22 (Y═Se, Te) with carbon dioxide. The resultant carboxylic acids 43 (Y═Se, Te) can then be esterified by standard methods [*Organikum* (*Practical Organic Chemistry*), Wiley-VCH, Weinheim, 21st Edn. 2001] using suitable alcohols 35, in particular phenols 35 (cf. Scheme XVI).

Scheme XVI: Compounds I (Y = Se, Te) containing ester bridges

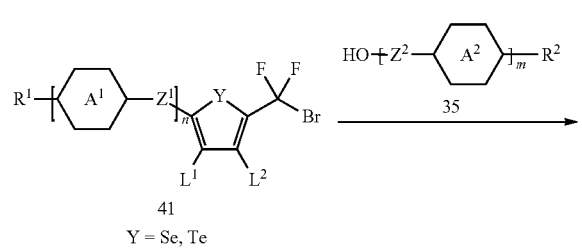

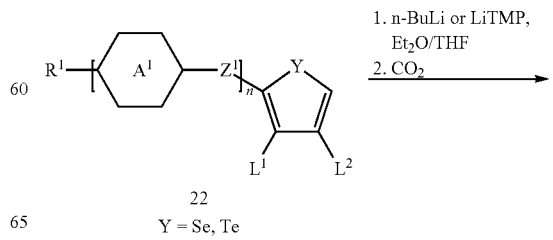

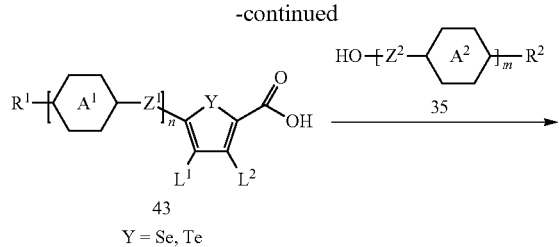

43
Y = Se, Te

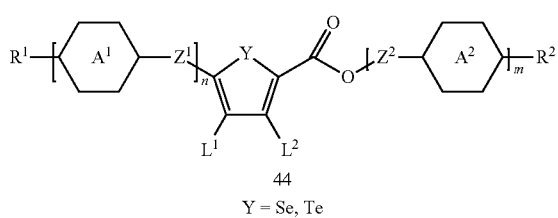

44
Y = Se, Te

In a particularly preferred embodiment of the compounds I, the selenophene or tellurophene unit is linked directly to a tetrahydropyranyl substituent. These compounds 47 (Y=Se, Te) are prepared from formylchalcogenophenes 25 (Y=Se, Te) and homoallyl alcohols 45. In a Prins-like cyclisation, generally mediated by Lewis acid halides [L. Coppi, A. Ricci, M. Taddei, *J. Org. Chem.* 1988, 53, 911-913], firstly the tetrahydropyranyl halides 46 (Y=Se, Te) are obtained, which are then converted into the desired compounds 47 (Y=Se, Te) by elimination and hydrogenation (cf. Scheme XVII).

Scheme XVII: Synthesis of the compounds I (Y = Se, Te) containing tetra-hydropyranyl substituents

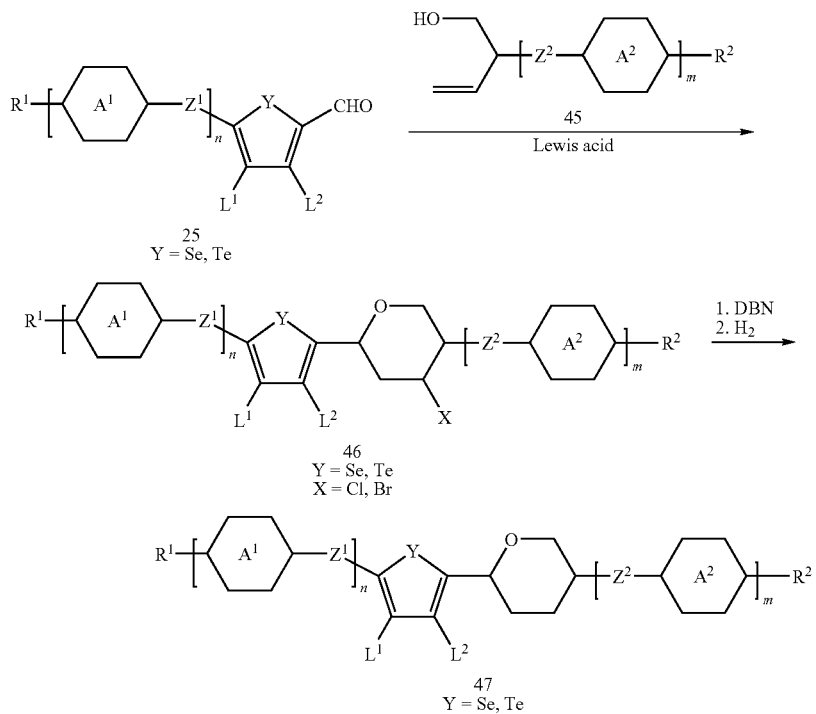

Scheme XVIII: Synthesis of the compounds I (Y = Se, Te) containing 1,3-dioxane substituents

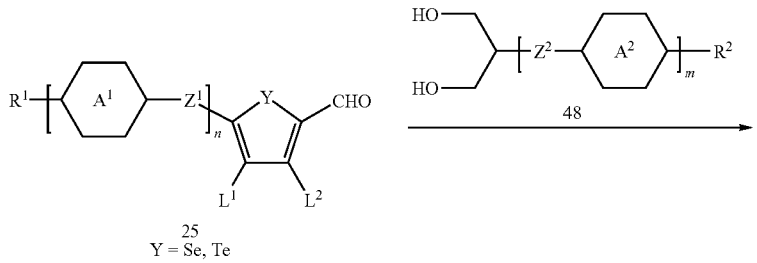

-continued

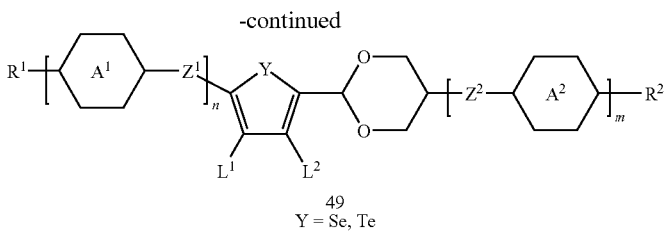

49
Y = Se, Te

In a particularly preferred embodiment of the compounds I, the selenophene or tellurophene unit is linked directly to a dioxane ring (cf. Scheme XVIII). To this end, 2-formylchalcogenophene compounds 25 (Y=Se, Te) are reacted with corresponding 1,3-diols 48.

Particular preference is given to compounds in which one (or two) oxygen atom(s) is (are) bonded directly to the chalcogenophene unit (for example compounds 53, cf. Scheme XX). Compounds of this type are particularly preferably prepared from 2-hydroxychalcogenophenes 50 (Y=Se, Te) (cf. Schemes XIX and XX).

Scheme XIX: 2-hydroxyselenophenes (50, Y = Se) and 2-hydroxytelluro-phenes (50, Y = Te)

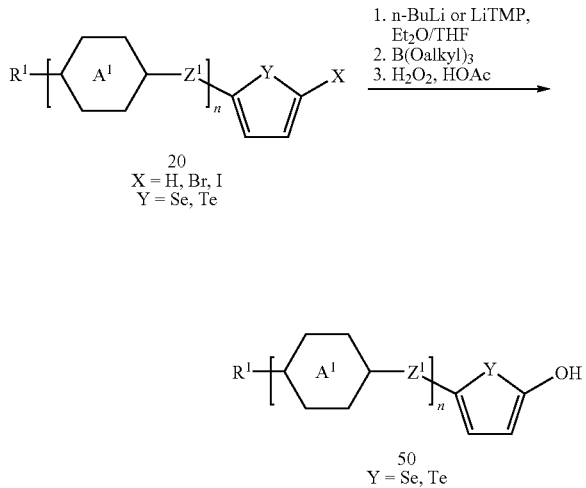

2-Hydroxychalcogenophenes 50 (Y=Se, Te) are accessible via the 2-lithiochalcogenophenes [B. Cederlund, A.-B. Hörnfeldt, *Acta Chem. Scand. Ser. B* 1976, 30, 101-108]. The latter are reacted with trialkyl borate, and the boronic acid esters generated in situ are oxidised using hydrogen peroxide to give the hydroxychalcogenophenes 50 (Y=Se, Te). 2-Hydroxychalcogenophenes 50 (Y=Se, Te) are in the form of a mixture of various tautomers [B. Cederlund, A.-B. Hörnfeldt, *Acta Chem. Scand. Ser. B* 1976, 30, 101-108]. For reasons of simplicity, only the hydroxyl form is shown here, and the substances are also referred to below as hydroxychalcogenophenes.

Very particular preference is given to compounds of type 53 (Y=Se, Te) containing alkoxy bridges or alkoxy radicals bonded directly to the chalcogenophene unit (m=0) (cf. Scheme XX). Through the choice of suitable alkylating agents (those of the sulfate type 52 are particularly preferred), a sufficiently high proportion of the O-alkylation product 53 can generally be obtained, which can then be isolated from the reaction mixture by standard laboratory separation methods (Method A in Scheme XX). A further preferred method consists in the reaction of chalcogenophene halides 20 (Y=Se, Te and X=Br, I) with alkoxides in the presence of copper salts [analogously to M. A. Keegstra, T. H. A. Peters, L. Brandsma, *Tetrahedron* 1992, 48, 3633-3652].

Scheme XX: Synthesis of 2-alkoxychalcogenophenes 53 (Y = Se, Te)

Method A:
From hydroxychalcogenophenes 50 (Y = Se, Te)

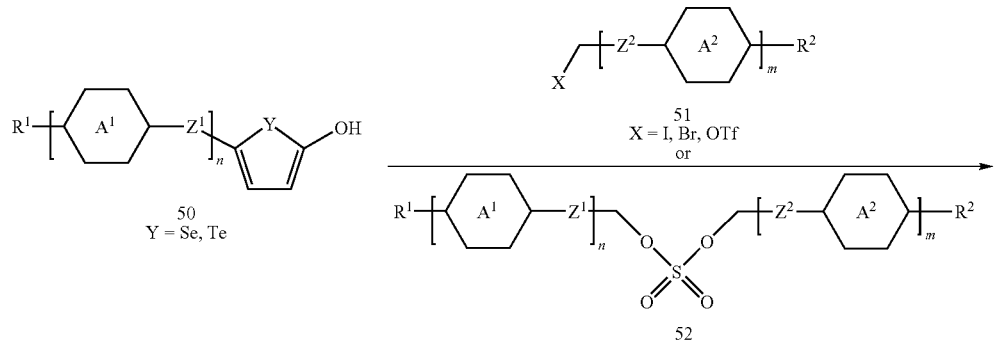

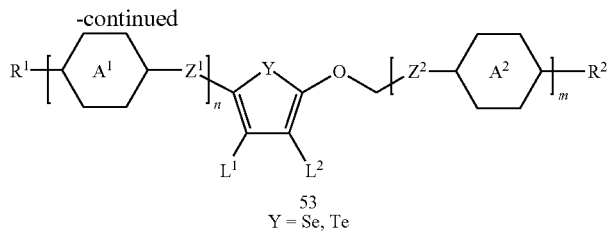

53
Y = Se, Te

Method B:

From chalcogenophene halides 20 (Y=Se, Te and X=Br, I)

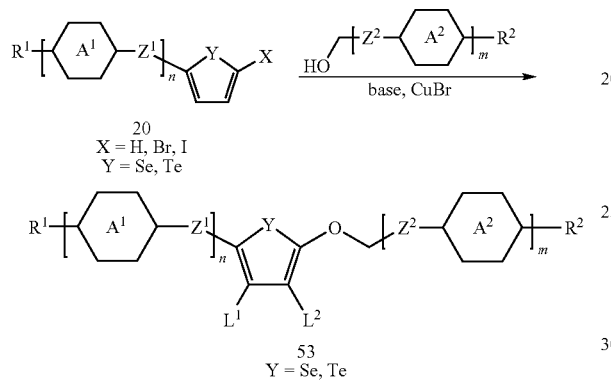

Further, particularly preferred compounds which are obtained from 2-hydroxychalcogenophenes 50 (Y=Se, Te) are those containing OCF$_2$ units 55 (Y=Se, Te) (cf. Scheme XXI) and ester groups 56 (Y=Se, Te) (cf. Scheme XXII).

The former are obtained from hydroxychalcogenophenes 50 (Y=Se, Te) in a substitution reaction with difluorobromo compounds 54. Esters, such as the compounds 56, can be obtained by acylation of hydroxychalcogenophenes 50 (Y=Se, Te).

Scheme XXI: Compounds containing OCF$_2$ units 55 (Y = Se, Te)

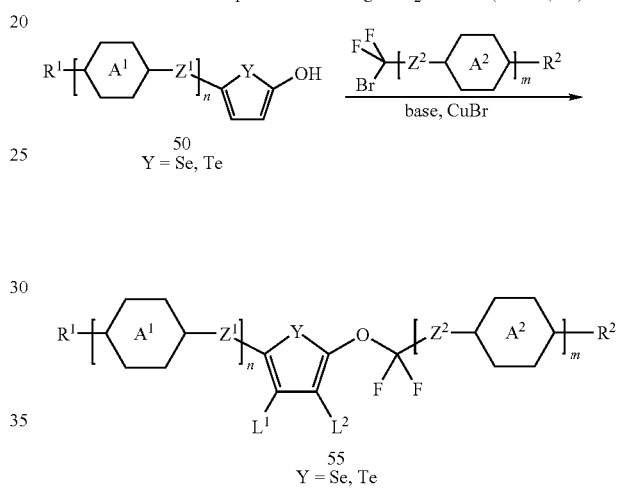

Scheme XXII: Acylation of 2-hydroxychalcogenophenes 50 (Y = Se, Te)

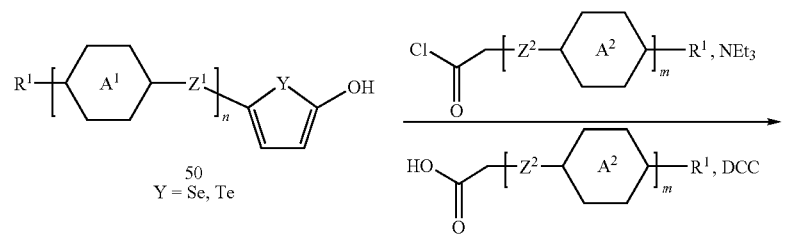

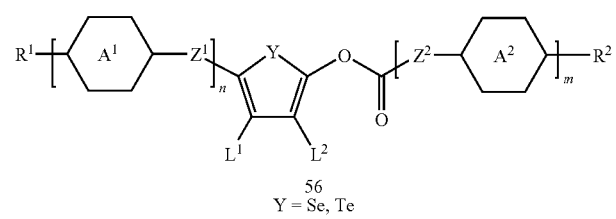

The chalcogenopheneboronic acid esters 57 (Y=Se, Te) or chalcogenopheneboronic acids 58 (Y=Se, Te) formed as intermediates in the synthesis of 2-hydroxychalcogenophenes 50 (Y=Se, Te) can also be isolated (cf. Scheme XXIII). These compounds are valuable intermediates, and they can be used further in a variety of ways, but preferably in Suzuki couplings [cf. in this respect *Metal-Catalyzed Cross-Coupling Reactions* (Eds.: A. de Meijre, F. Diederich), Wiley-VCH, Weinheim, 2004].

Scheme XXIII: Chalcogenopheneboronic acid esters 57 (Y = Se, Te) and chalcogenopheneboronic acids 58 (Y = Se, Te)

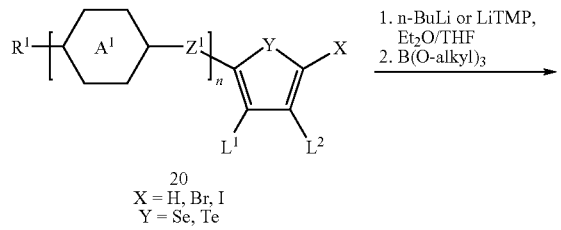

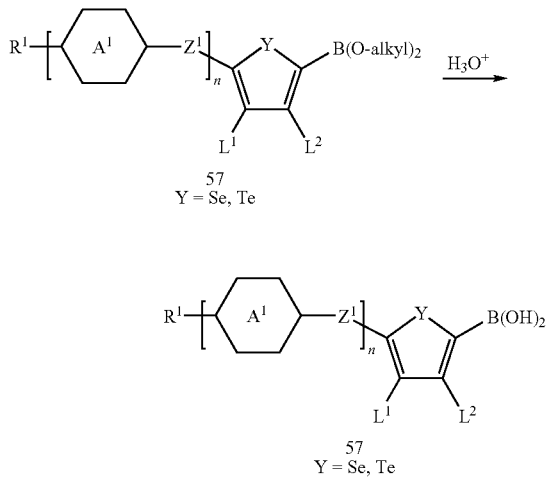

Particular preference is also given to chalcogenophenes in which m=0 and $R^2$ denotes fluorine. Such compounds are obtained from the reaction of lithiated or metallated chalcogenophene derivatives 21 (cf. Scheme V; Y=Se, Te and M=Li and MgBr are particularly preferred) with electrophilic fluorinating reagents [G. S. Lal, G. P. Pez, R. G. Syvret, *Chem. Rev.* 1996, 96, 1737-1756], in particular N-fluoro-N-(phenylsulfonyl)benzenesulfonamide ((PhSO$_2$)$_2$NF).

Scheme XXIV: 2-Fluorochalcogeneophene derivatives 58 (Y = Se, Te)

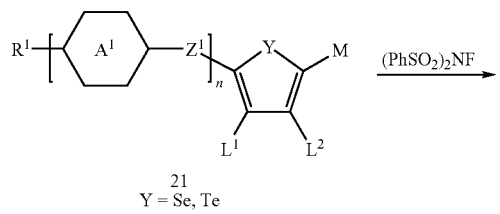

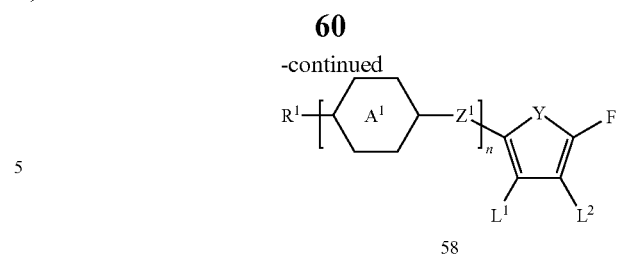

The synthesis of the compounds I in which $L^1$ and $L^2$ denote fluorine starts from 2,5-bis(trimethylsilyl)-3,4-dibromochalcogenophenes 61. These are prepared from the chalcogenophenes 59 via the tetrabromochalcogenophenes 60. As already described for the corresponding thiophene analogues [Y. Sakamoto, S. Komatsu, T. Suzuki, *J. Am. Chem. Soc.* 2001, 123, 4643-4644], the fluorinated building block 62 can be prepared by halogen-metal exchange and scavenging of the metallated intermediate using N-fluoro-N-(phenylsulfonyl)benzenesulfonamide ((PhSO$_2$)$_2$NF). Removal of the trimethylsilyl groups gives 3,4-difluorochalcogenophenes 63 (Y=Se, Te), which can be converted, as described in the above schemes, into compounds of type I where $L^1=L^2=F$.

Scheme XXV: Preparation of building blocks for the synthesis of the compounds I (Y = Se, Te) in which $L^1 = L^2 = F$.

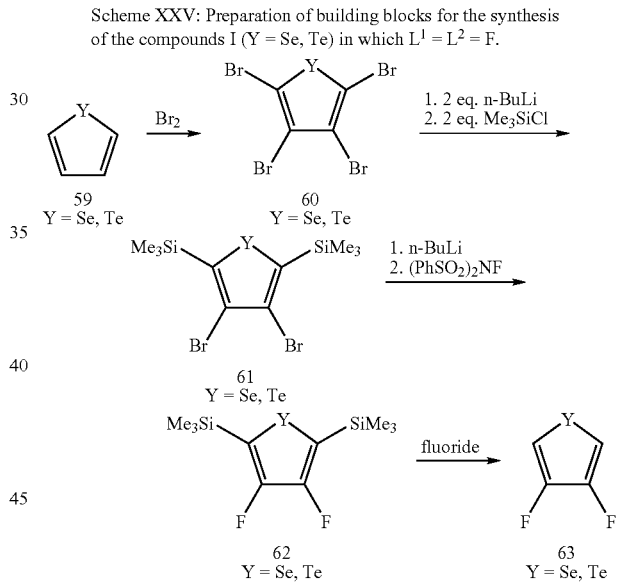

Further important synthetic building blocks for liquid-crystalline chalcogenophene derivatives of type I (where Y=Se, Te and $L^1=L^2=F$) are obtained starting from the compounds 62 by treatment with NBS. The compounds 64 and the compounds 65 accessible starting therefrom can be used, as described, as synthetic building blocks.

Scheme XXVI: Further building blocks 64 and 65 for the synthesis of the compounds I (Y = Se, Te) in which $L^1 = L^2 = F$.

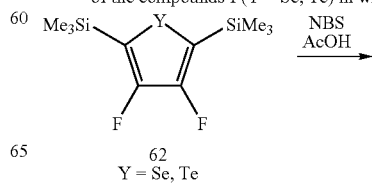

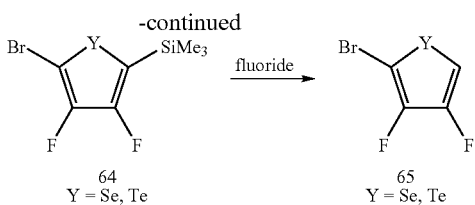

Synthetic building blocks 66 and 67 are also accessible by the person skilled in the art in accordance with these reaction principles [for example analogously to E. Dvornikova, M. Bachcicka, K. Kamienska-Trela, A. Krowczynski, *J. Fluor. Chem.* 2003, 124, 159-168] in which only one of the substituents $L^1$ or $L^2$ denotes fluorine and the other substituent is equal to hydrogen.

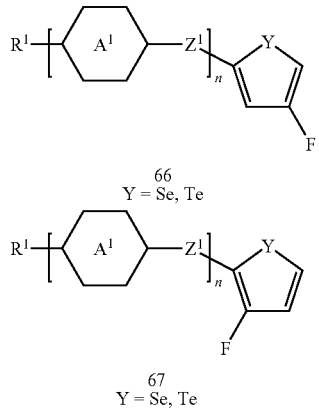

Scheme XXVII: Building blocks for the synthesis of the compounds I (Y = Se, Te) in which $L^1$ = F and $L^2$ = H or $L^1$ = H and $L^2$ = F.

In the preparation of compounds of the formula I, chalcogenophene-containing intermediates occur which are depicted and explained in the schemes shown above. The radicals $R^1$—-$[A^1$-$Z^1]_n$- and —$[Z^2$-$A^2]_m$—$R^2$ generally have the same definition, so only the radical $R^1$-$[A^1$-$Z^1]_n$- will be expressly indicated for the following intermediates.

The invention also encompasses compounds and intermediates of the formula II:

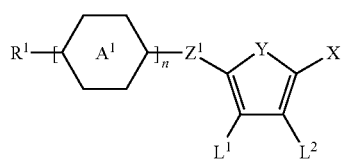

in which
$R^1$, $A^1$, $Z^1$, Y, $L^1$ and $L^2$ are as defined for formula I and preferred forms thereof, and
n denotes 1, 2, 3 or 4,
X denotes —Br, —I, —OH, —O(SO$_2$)R$^3$, —B(OH)$_2$, —B(OR$^4$)$_2$, —CH$_2$OH, —CF$_2$Br or —CHO, preferably —Br, —I, —B(OH)$_2$, —CF$_2$Br or —CHO,
$R^3$ denotes 1-5 C alkyl, 1-5 C perfluoroalkyl or p-tolyl, and
$R^4$ denotes 1-12 C alkyl or $R^4$+$R^4$ together denote a 1,2- or 1,3-alkylene or a 1,2-phenylene group, which may be substituted by 1-4 C alkyl.

The intermediates of the formula II can be prepared easily, as indicated, and result in a simple manner in the desired end compounds of the formula I.

As already mentioned, the compounds of the general formula I can be used in liquid-crystalline media.

The present invention therefore also relates to a liquid-crystalline medium comprising at least two liquid-crystalline compounds, comprising at least one compound of the formula I.

The present invention also relates to liquid-crystalline media comprising 2 to 40, preferably 4 to 30, components as further constituents besides one or more compounds of the formula I according to the invention. These media particularly preferably comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, 1,3-dioxanes, 2,5-tetrahydropyrans, phenyl or cyclohexyl benzoates, phenyl or cyclohexyl esters of cyclohexanecarboxylic acid, phenyl or cyclohexyl esters of cyclohexoylbenzoic acid, phenyl or cyclohexyl esters of cyclohexylcyclohexane-carboxylic acid, cyclohexylphenyl esters of benzoic acid, of cyclohexanecarboxylic acid or of cyclohexylcyclohexanecarboxylic acid, phenylcyclohexane, cyclohexylbiphenyls, phenylcyclohexylcyclohexanes, cyclohexyl-cyclohexanes, cyclohexylcyclohexylcyclohexenes, 1,4-biscyclohexylbenzenes, 4',4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylethanes, 1-phenyl-2-cyclohexylphenyl-ethanes, optionally halogenated stilbenes, benzyl phenyl ethers, tolans and substituted cinnamic acids. The 1,4-phenylene groups in these compounds may also be mono- or polyfluorinated.

The most important compounds suitable as further constituents of media according to the invention can be characterised by the formulae (II), (III), (IV), (V) and (VI):

R'-L-E-R"  (II)

R'-L-(CO)O-E-R"  (III)

R'-L-O(CO)-E-R"  (IV)

R'-L-CH$_2$CH$_2$-E-R"  (V)

R'-L-CF$_2$O-E-R"  (VI)

In the formulae (II), (III), (IV), (V) and (VI), L and E, which may be identical or different, each, independently of one another, denote a divalent radical from the group formed by -Phe-, -Cyc-, -Phe-Phe-, -Phe-Cyc-, -Cyc-Cyc-, -Pyr -Dio-, -Thp-, -G-Phe- and -G-Cyc- and their mirror images, where Phe denotes unsubstituted or fluorine-substituted 1,4-phenylene, Cyc denotes trans-1,4-cyclohexylene or 1,4-cyclohexenylene, Pyr denotes pyrimidine-2,5-diyl or pyridine-2,5-diyl, Dio denotes 1,3-dioxane-2,5-diyl, Thp denotes tetrahydropyran-2,5-diyl and G denotes 2-(trans-1,4-cyclohexyl)ethyl, pyrimidine-2,5-diyl, pyridine-2,5-diyl, 1,3-dioxane-2,5-diyl or tetrahydropyran-2,5-diyl.

One of the radicals L and E is preferably Cyc or Phe. E is preferably Cyc, Phe or Phe-Cyc. The media according to the invention preferably comprise one or more components selected from the compounds of the formulae (II), (III), (IV), (V) and (VI) in which L and E are selected from the group Cyc and Phe and simultaneously one or more components selected from the compounds of the formulae (II), (III), (IV), (V) and (VI) in which one of the radicals L and E is selected from the group Cyc and Phe and the other radical is selected from the group -Phe-Phe-, -Phe-Cyc-, -Cyc-Cyc-, -G-Phe- and -G-Cyc-, and optionally one or more components selected from the compounds of the formulae (II), (III), (IV), (V) and (VI) in which the radicals L and E are selected from the group -Phe-Cyc-, -Cyc-Cyc-, -G-Phe- and -G-Cyc-.

In a smaller sub-group of the compounds of the formulae (II), (III), (IV), (V) and (VI), R' and R" each, independently of one another, denote alkyl, alkenyl, alkoxy, alkoxyalkyl (oxaalkyl), alkenyloxy or alkanoyloxy having up to 8 C atoms. This smaller sub-group is called group A below, and the compounds are referred to by the sub-formulae (IIa), (IIIa), (IVa), (Va) and (VIa). In most of these compounds, R' and R" are different from one another, one of these radicals usually being alkyl, alkenyl, alkoxy or alkoxyalkyl (oxaalkyl).

In another smaller sub-group of the compounds of the formulae (II), (III), (IV), (V) and (VI), which is known as group B, E denotes a fluorinated phenylene radical of the formula

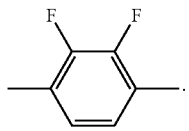

In the compounds of group B, which are referred to by the sub-formulae (IIb), (IIIb), (IVb), (Vb) and (VIb), R' and R" have the meaning indicated for the compounds of the sub-formulae (IIa) to (Via) and are preferably alkyl, alkenyl, alkoxy or alkoxyalkyl (oxaalkyl).

In a further sub-group of the compounds of the formulae (II), (III), (IV), (V) and (VI), R" denotes —F, —Cl, —CN, —NCS or —(O)$_i$CH$_{3-k}$F$_k$, where i is 0 or 1 and k is 1, 2 or 3. This sub-group is referred to below as group C, and the compounds of this sub-group are correspondingly described by sub-formulae (IIc), (IIIc), (IVc), (Vc) and (VIc). In the compounds of the subformulae (IIc), (IIIc), (IVc), (Vc) and (VIc), R' has the meaning indicated for the compounds of the sub-formulae (IIa) to (Via) and is preferably alkyl, alkenyl, alkoxy or alkoxyalkyl (oxaalkyl).

Besides the preferred compounds of groups A, B and C, other compounds of the formulae (II), (III), (IV), (V) and (VI) having other variants of the proposed substituents are also customary. All these substances are obtainable by methods which are known from the literature or analogously thereto.

Besides the compounds of the general formula I according to the invention, the media according to the invention preferably comprise one or more compounds from groups A, B and/or C. The media preferably comprise one or more compounds from group A and one or more compounds from group B for dielectrically negative mixtures or additionally one or more compounds from group C for dielectrically positive mixtures. The proportions by weight of the compounds from these groups in the media according to the invention are:

group A:
0 to 90%, preferably 15 to 90%, in particular 20 to 85%.
group B:
0 to 80%, preferably 10 to 85%, in particular 15 to 80%.
group C:
0 to 80%, preferably 15 to 90%, in particular 20 to 85%.

The media according to the invention preferably comprise 1 to 40%, particularly preferably 5 to 30%, of the compounds of the formula I according to the invention. Preference is furthermore given to media comprising more than 40%, in particular 45 to 90%, of compounds of the formula I according to the invention. The media preferably comprise one, two, three, four or five compounds of the formula I according to the invention.

The media according to the invention are prepared in a manner conventional per se. In general, the components are dissolved in one another, preferably at elevated temperature. By means of suitable additives, the liquid-crystalline phases of the present invention can be modified in such a way that they can be used in all types of liquid-crystal display element that have been disclosed hitherto. Additives of this type are known to the person skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems or substances can be added in order to modify the dielectric anisotropy, the viscosity and/or the alignment of the nematic phases.

In the case of a negative $\Delta\epsilon$, the compounds of the formula I are particularly suitable for use in VA-TFT display systems, in the case of a positive $\Delta\epsilon$ they are particularly, but not exclusively, suitable for TN-TFT, STN or IPS display systems. Dielectrically approximately neutral derivatives are of importance as nematic phase formers or low-viscosity component for all liquid-crystalline media. Further display types in which media having correspondingly suitable dielectric properties can be employed will be known to the person skilled in the art.

The present invention also relates to electro-optical liquid-crystal display elements containing a liquid-crystalline medium according to the invention.

The following examples are intended to explain the invention without limiting it. Above and below, percentage data denote percent by weight. All temperatures are indicated in degrees Celsius. Furthermore, C=crystalline state, N=nematic phase, Sm=smectic phase and I=isotropic phase. The data between these symbols represent the transition temperatures. $\Delta n$ denotes the optical anisotropy (589 nm, 20° C.), $\Delta\epsilon$ denotes the dielectric anisotropy (1 kHz, 20° C.) and $\gamma_1$ denotes the rotational viscosity (in the unit mPa·s).

Physical, physicochemical or electro-optical parameters are determined by generally known methods, as described, inter alia, in the brochure "Merck Liquid Crystals—Licristal®—Physical Properties of Liquid Crystals—Description of the Measurement Methods", 1998, Merck KGaA, Darmstadt. Above and below, $\Delta n$ denotes the optical anisotropy (589 nm, 20° C.) and $\Delta\epsilon$ denotes the dielectric anisotropy (1 kHz, 20° C.). The dielectric anisotropy $\Delta\epsilon$ is determined at 20° C. and 1 kHz. The optical anisotropy $\Delta n$ is determined at 20° C. and a wavelength of 589.3 nm.

The $\Delta\epsilon$ and $\Delta n$ values and the rotational viscosity ($\gamma_1$) of the compounds according to the invention are obtained by linear extrapolation from liquid-crystalline mixtures consisting of 5 to 10% of the respective compound according to the invention and 90-95% of the commercially available liquid-crystal mixture ZLI-2857 (for $\Delta\epsilon<1$) or ZLI-4792 (for $\Delta\epsilon>1$, $\Delta n$, $\gamma_1$) (mixtures, Merck KGaA, Darmstadt).

The following abbreviations are used:
THF tetrahydrofuran
MTBE MTB ether, methyl t-butyl ether
sat. saturated
NMP N-methyl-2-pyrrolidone
RT room temperature (20-25° C.)

TMP 2,2,6,6-tetramethylpiperidine
IPA 2-propanol
NBS n-bromosuccinimide

EXAMPLES

Example 1

2-Methyl-5-[4-(4-propylcyclohexyl)phenyl]selenophene

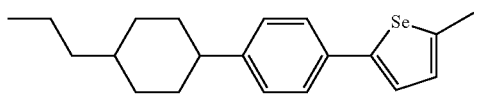

1.1 Preparation of 2-[4-(4-propylcyclohexyl)phenyl]selenophene

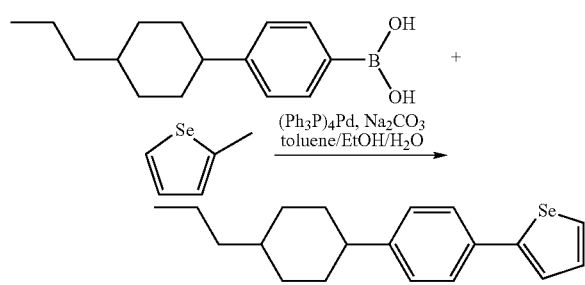

A mixture of 11.0 g (41.1 mmol) of 2-iodoselenophene, 7.98 g (32.4 mmol) of 4-(4-propylcyclohexyl)phenylboronic acid, 3.70 g (3.20 mmol) of tetrakis(triphenylphosphine)palladium(0) and 60 ml of 2 N sodium carbonate soln. in 160 ml of toluene/ethanol (1:1) is heated under reflux for 22 h. After cooling, water is added, and the batch is extracted a number of times with MTBE. The combined organic phases are washed with water, sat. sodium hydrogencarbonate soln., 1 N hydrochloric acid and sat. sodium chloride soln. The solution is dried using sodium sulfate and concentrated to dryness. The residue is purified by column chromatography (SiO$_2$, n-heptane:EtOAc=20:1). The further purification is carried out by recrystallisation from n-heptane; 2-[4-(4-propylcyclohexyl)phenyl]selenophene is obtained as a colourless solid.

1.2 Preparation of 2-methyl-5-[4-(4-propylcyclohexyl)phenyl]selenophene

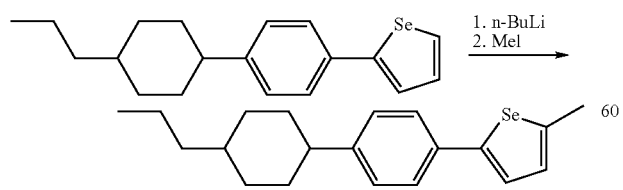

3.4 g (10.3 mmol) of 2-[4-(4-propylcyclohexyl)phenyl]selenophene are initially introduced in 100 ml of diethyl ether, and 9.0 ml (14.3 mmol, 15% soln. in hexane) of n-BuLi are metered in rapidly. The mixture is heated under reflux for 25 min and subsequently cooled to −78° C. 1.60 ml (25.7 mmol) of methyl iodide are added in one portion, and the mixture is warmed to RT and stirred for 24 h. Sat. ammonium chloride soln. and conc. ammonia soln. are added, and the batch is stirred vigorously for a few minutes. The mixture is acidified using hydrochloric acid, and the organic phase is separated off. The aqueous phase is extracted with MTBE, and the combined organic phases are dried using sodium sulfate. The solution is concentrated to dryness, and the residue is purified by column chromatography (SiO$_2$, n-heptane:EtOAc=25:1). The further purification is carried out by recrystallisation from ethanol and n-heptane. 2-Methyl-5-[4-(4-propylcyclohexyl)phenyl]selenophene is obtained as a colourless solid (m.p. 98° C.).

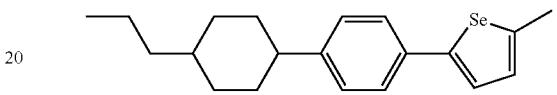

Δ∈=0.0
Δn=0.1885
$γ_1$=332 mPa·s
C 98 SmB 102 N 166 I
$^1$H-NMR (250 MHz, CHCl$_3$): δ=7.40 (dm, 2H, J=8.3 Hz, H$_{arom.}$), 7.19-7.14 (m, 3H, H$_{arom.}$), 6.87-6.85 (m, 1H, H$_{arom.}$), 2.57 (d, 3H, J=1.0 Hz, Me$_{selenophene}$), 2.45 (ddd*, 1H, J=12.1 Hz, J=3.0 Hz, H$_{benzyl.}$), 1.93-1.83 (m, 4H, H$_{aliph.}$), 1.52-1.16 (m, 7H, H$_{aliph.}$), 1.12-1.01 (m, 2H, H$_{aliph.}$), 0.90 (t, 3H, J=7.1 Hz, CH$_2$CH$_2$CH$_3$).
MS (EI): m/e (%)=346 (100, [M+1]$^+$).

Example 2

2-Propyl-5-[4-(4-propylcyclohexyl)phenyl]selenophene

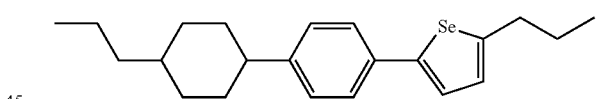

2.1 Preparation of 5-[4-(4-propylcyclohexyl)phenyl]selenophene-2-carbaldehyde

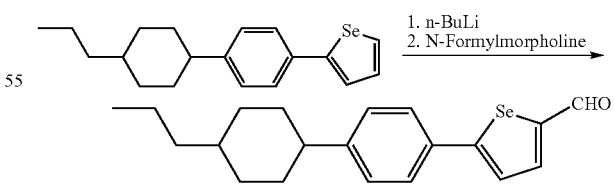

1.48 g (4.47 mmol) of 2-[4-(4-propylcyclohexyl)phenyl]selenophene are initially introduced in 15 ml of diethyl ether, and 4.4 ml (7.0 mmol, 15% soln. in hexane) of n-BuLi are metered in rapidly. The mixture is heated under reflux for 15 min and subsequently cooled to −78° C. 1.4 ml (14.0 mmol) of N-formylmorpholine are added in one portion, and the mixture is warmed to RT and stirred for 24 h. The batch is diluted with MTBE, and 1 N hydrochloric acid is added. The organic phase is separated off, and the aqueous phase is extracted with MTBE. The combined organic phases are washed with sat. sodium chloride solution and dried using sodium sulfate. The solution is concentrated to dryness, and the residue is recrystallised from n-heptane. 5-[4-(4-Propylcyclohexyl)phenyl]selenophene-2-carbaldehyde is obtained as a red solid.

2.2 Preparation of 2-(propenyl)-5-[4-(4-propylcyclohexyl)phenyl]selenophene

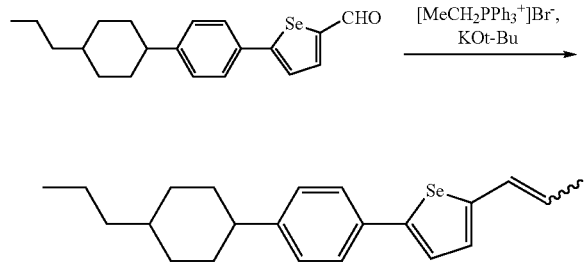

1.80 g (4.85 mmol) of ethyltriphenylphosphonium bromide are initially introduced in 8 ml of THF at 0° C., and 533 mg (4.75 mmol) of potassium tert-butoxide are added. After 1.5 h at RT, a solution of 1.16 g (3.23 mmol) of 5-[4-(4-propylcyclohexyl)phenyl]selenophene-2-carbaldehyde in 7 ml of THF is added, and the batch is stirred for 2.5 h. The mixture is diluted with MTBE, and sat. ammonium chloride soln. and 2 N hydrochloric acid are added. The organic phase is separated off, and the aqueous phase is extracted with MTBE. The combined organic phases are washed with sat. sodium chloride soln. and dried using sodium sulfate. The solution is concentrated to dryness, and the residue is purified by column chromatography (SiO$_2$, n-heptane→n-heptane:EtOAc=20:1). 2-(Propenyl)-5-[4-(4-propylcyclohexyl)phenyl]selenophene is obtained as an E/Z isomer mixture.

2.3 Preparation of 2-propyl-5-[4-(4-propylcyclohexyl)phenyl]selenophene

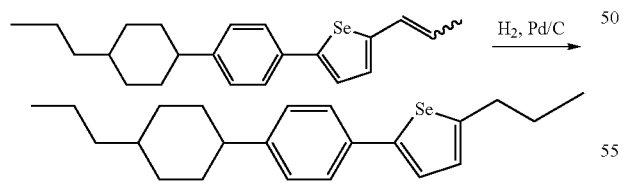

1.0 g (2.69 mmol) of 2-(propenyl)-5-[4-(4-propylcyclohexyl)phenyl]selenophene is hydrogenated in 10 ml of ethyl acetate, in the presence of Pd/C (5% of Pd) at atmospheric pressure and RT. The reaction soln. is filtered and concentrated to dryness, and the crude product is purified by column chromatography (SiO$_2$, n-heptane→n-heptane:EtOAc=20:1). The further purification is carried out by recrystallisation from n-heptane. 2-Propyl-5-[4-(4-propylcyclohexyl)phenyl]selenophene is obtained as a colourless solid.

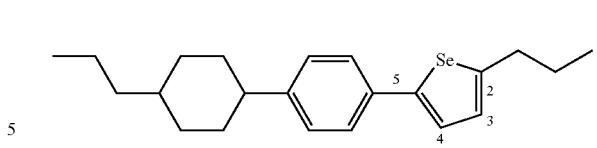

Δ∈c=2.3

Δn=0.1759

γ$_1$=218 mPa·s

? SmB 126 N 149 I $^1$H-NMR (300 MHz, CHCl$_3$): δ=7.42 (dm, 2H, J=8.3 Hz, H$_{arom.}$), 7.20-7.15 (m, 3H, H$_{arom.}$), 6.89 (dt, 1H, J=3.6 Hz, J=1.2 Hz, 3-H), 2.84 (dt, 2H, J=7.5 Hz, J=2.8 Hz, CH$_2$CH$_2$CH$_3$), 2.46 (ddd*, 1H, J=12.2 Hz, J=3.3 Hz, H$_{benzyl.}$), 1.92-1.84 (m, 4H, H$_{aliph.}$), 1.78-1.66 (m, 2H, H$_{aliph.}$), 1.51-1.41 (m, 2H, H$_{aliph.}$), 1.40-1.27 (m, 3H, H$_{aliph.}$), 1.26-1.17 (m, 2H, H$_{aliph.}$), 1.12-0.98 (m, 5H, CH$_2$CH$_2$CH$_3$, H$_{aliph.}$), 0.90 (t, 3H, J=7.1 Hz, H$_3$CCH$_2$CH$_2$).

MS (EI): m/e (%)=374 (100, [M+1]$^+$), 345 (76, [M-Et]$^+$).

Example 3

2-Methyl-5-(4-trifluoromethoxyphenyl)selenophene

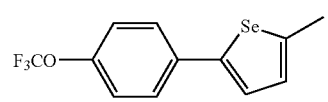

3.1 Preparation of 2-(4-trifluoromethoxyphenyl)selenophene

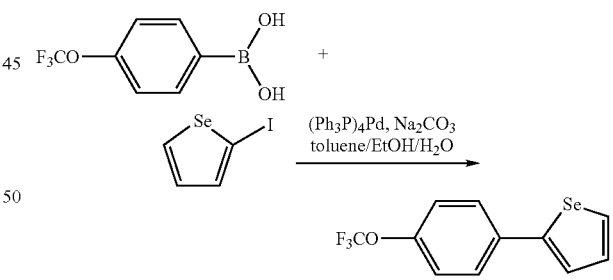

A mixture of 15.1 g (58.7 mmol) of 2-iodoselenophene, 13.9 g (67.7 mmol) of 4-trifluoromethoxyphenylboronic acid, 3.90 g (3.38 mmol) of tetrakis(triphenylphosphine)palladium(0) and 150 ml of 2 N sodium carbonate soln. in 400 ml of toluene/ethanol (1:1) is heated under reflux for 23 h. After cooling, the organic phase is separated off, and the aqueous phase is extracted a number of times with MTBE. The combined organic phases are washed with 1 N hydrochloric acid and sat. sodium chloride soln. The solution is dried using sodium sulfate and concentrated to dryness. The residue is purified by column chromatography (SiO$_2$, n-heptane:EtOAc=20:1→10:1→1:1). Further purification is carried out by recrystallisation from n-heptane; 2-(4-trifluoromethoxyphenyl)selenophene is obtained as a yellowish solid.

3.2 Preparation of 2-methyl-5-(4-trifluoromethoxyphenyl)selenophene

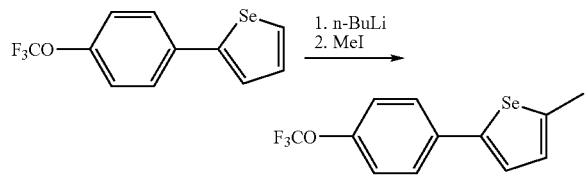

8.6 g (29.5 mmol) of 2-(4-trifluoromethoxyphenyl)selenophene are initially introduced in 50 ml of diethyl ether, and 25.0 ml (39.8 mmol, 15% soln. in hexane) of n-BuLi are metered in rapidly. The mixture is heated under reflux for 25 min and subsequently cooled to −70° C. 7.4 ml (0.12 mol) of methyl iodide are added in one portion, and the mixture is warmed to RT and stirred for 24 h. Sat. ammonium chloride soln. and conc. ammonia soln. are added, and the batch is stirred vigorously for a few minutes. The organic phase is separated off, and the aqueous phase is extracted with MTBE. The combined organic phases are washed successively with water, 2 N hydrochloric acid and sat. sodium chloride soln. and dried using sodium sulfate. The solution is concentrated to dryness, and the residue is purified by column chromatography (SiO$_2$, n-heptane:EtOAc=20:1→10:1). The further purification is carried out by recrystallisation from n-heptane. 2-Methyl-5-(4-trifluoromethoxyphenyl)selenophene is obtained as a colourless solid (m.p. 122° C.).

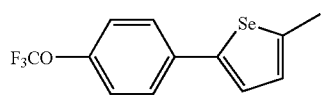

Δε=8.5
Δn=0.1424
γ$_1$=20 mPa·s
C 122 I
$^1$H-NMR (300 MHz, CHCl$_3$): δ=7.49 (dm, 2H, J=8.7 Hz, H$_{arom.}$), 7.21-7.16 (m, 3H, H$_{arom.}$), 6.90-6.88 (m, 1H, H$_{arom.}$), 2.59 (d, 3H, J=0.9 Hz, Me).
$^{19}$F-NMR (282 MHz, CHCl$_3$): δ=−57.9 (s, 3F).
MS (EI): m/e (%)=306 (42, [M+1]$^+$), 225 (28), 41 (100).

Example 4

2-(4-Ethoxy-2,3-difluorophenyl)-5-methylselenophene

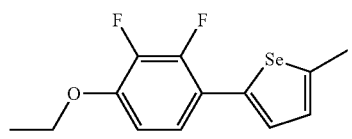

4.1 Preparation of 2-(4-ethoxy-2,3-difluorophenyl)selenophene

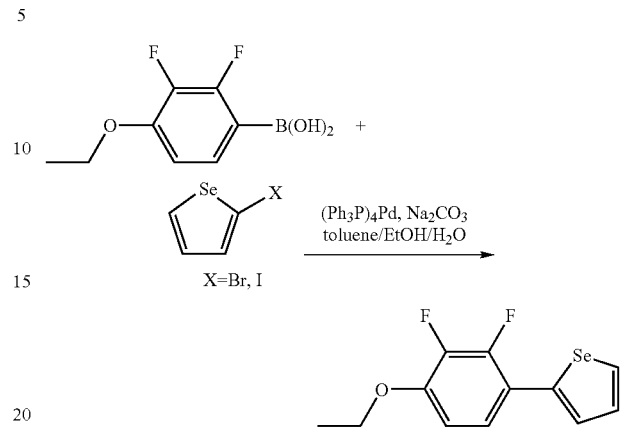

Method A (from 2-iodoselenophene):

A mixture of 34.8 g (0.14 mol) of 2-iodoselenophene, 32.8 g (0.16 mol) of 4-ethoxy-2,3-difluorophenylboronic acid, 8.10 g (77.01 mmol) of tetrakis-(triphenylphosphine)palladium(0) and 300 ml of 2 N sodium carbonate soln. in 800 ml of toluene/ethanol (1:1) is heated under reflux for 23 h. The mixture is diluted with MTBE and washed with water. The aqueous phase is extracted with MTBE, and the combined organic phases are washed with 2 N hydrochloric acid and sat. sodium chloride soln. The solution is dried using sodium sulfate and concentrated to dryness. The residue is purified by column chromatography (SiO$_2$, n-heptane:EtOAc=15:1-10:1→5:1). Further purification is carried out by recrystallisation from n-heptane; 2-(4-ethoxy-2,3-difluorophenyl)selenophene is obtained as a beige solid.

Method B (from 2-bromoselenophene):

A mixture of 45.0 g (0.21 mol) of 2-bromoselenophene, 52.0 g (0.26 mol) of 4-ethoxy-2,3-difluorophenylboronic acid, 20.0 g (17.3 mmol) of tetrakis(triphenylphosphine)palladium(0) and 600 ml of 2 N sodium carbonate soln. in 1100 ml of toluene/ethanol (1:1) is heated under reflux for 20 h. After cooling, the organic phase is separated off, and the aqueous phase is extracted with toluene. The combined organic phases are washed with sat. sodium hydrogencarbonate soln., 1 N hydrochloric acid and sat. sodium chloride soln. The solution is dried using sodium sulfate and concentrated to dryness. The residue is purified by column chromatography (SiO$_2$, n-heptane:toluene=3:2). Further purification is carried out by recrystallisation from ethanol; 2-(4-ethoxy-2,3-difluorophenyl)selenophene is obtained as a beige solid.

4.2 Preparation of 2-(4-ethoxy-2,3-difluorophenyl)-5-methylselenophene

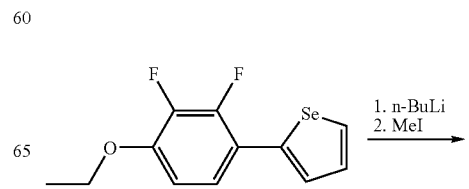

-continued

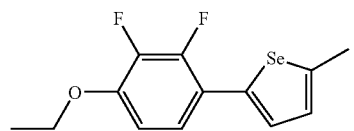

6.25 g (20.7 mmol) of 2-(4-ethoxy-2,3-difluorophenyl)selenophene are initially introduced in 50 ml of diethyl ether, and 16.9 ml (26.9 mmol, 15% soln. in hexane) of n-BuLi are metered in rapidly. The mixture is heated under reflux for 25 min and subsequently cooled to −70° C. 7.0 ml (0.11 mol) of methyl iodide are added in one portion, and the mixture is warmed to RT and stirred for 22 h. Sat. ammonium chloride soln. and conc. ammonia soln. are added, and the batch is stirred vigorously for a few minutes. The organic phase is separated off, and the aqueous phase is extracted with MTBE. The combined organic phases are washed with 2 N hydrochloric acid and sat. sodium chloride soln. and dried using sodium sulfate. The solution is concentrated to dryness, and the residue is purified by column chromatography (SiO$_2$, n-heptane:EtOAc=20:1→10:1→5:1). The further purification is carried out by recrystallisation from n-heptane; 2-(4-ethoxy-2,3-difluorophenyl)-5-methylselenophene is obtained as a colourless solid (m.p. 76° C.).

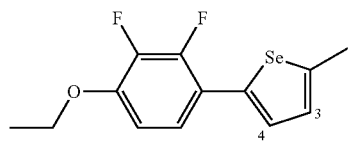

$\Delta\varepsilon$=5.5
$\Delta$n=0.1803
$\gamma_1$=53 mPa·s
C 76 I $^1$H-NMR (300 MHz, CHCl$_3$): δ=7.31 (d, 1H, J=3.3 Hz, 4-H), 7.15 (ddd, 1H, J=8.3 Hz, J=7.2 Hz, J=2.0 Hz, H$_{arom.}$), 6.91-6.89 (m, 1H, 3-H), 6.71 (ddd, 1H, J=8.3 Hz, J=7.2 Hz, J=2.0 Hz, H$_{arom.}$), 4.13 (q, 2H, J=7.0 Hz, H$_3$CCH$_2$O—), 2.59 (d, 3H, J=1.2 Hz, Me), 1.45 (t, 3H, J=7.0 Hz, H$_3$CCH$_2$O—).

$^{19}$F-NMR (282 MHz, CHCl$_3$): δ=−138.8 (dd, 2F, J=19.3 Hz, J=8.3 Hz), −158.7 (dd, 2F, J=19.3 Hz, J=8.3 Hz).

MS (EI): m/e (%)=302 (100, [M+1]$^+$), 273 (89, [M+1−Et]$^+$), 193 (70).

Example 5

2-(4-Ethoxy-2,3-difluorophenyl)-5-ethylselenophene

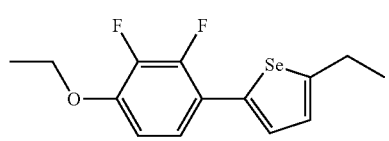

5.1 Preparation of 5-(4-ethoxy-2,3-difluorophenyl)selenophene-2-carbaldehyde

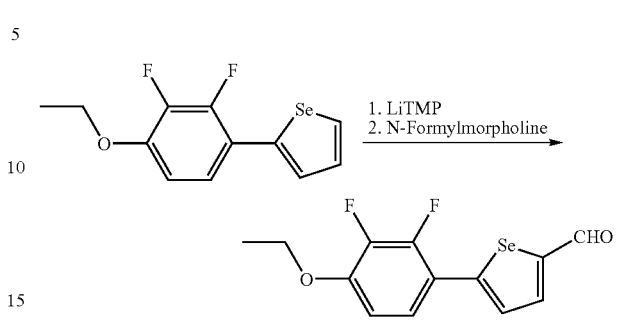

7.6 ml (44.4 mmol) of TMP are initially introduced at −20° C. in THF, and 26.7 ml (42.4 mmol, 15% soln. in hexane) of n-BuLi are metered in. After 25 min at this temperature, a solution of 11.7 g (38.6 mmol) of 2-(4-ethoxy-2,3-difluorophenyl)selenophene in 80 ml of THF is added. When the addition is complete, the batch is warmed to RT over the course of 45 min and left at this temperature for 20 min. The solution is cooled to −40° C., and N-formylmorpholine is added. The reaction mixture is warmed to RT and stirred for 4.5 h. The solution is diluted with a lot of dichloromethane, and 2 N hydrochloric acid is added. The mixture is briefly stirred vigorously, and the organic phase is separated off. The aqueous phase is extracted with dichloromethane, and the combined organic phases are washed with water. The solution is dried using sodium sulfate and concentrated to dryness. The residue is digested in cold ethanol, and the solid is filtered off with suction. Drying in vacuo gives 5-(4-ethoxy-2,3-difluorophenyl)selenophene-2-carbaldehyde as a violet solid.

5.2 Preparation of 2-(4-ethoxy-2,3-difluorophenyl)-5-vinylselenophene

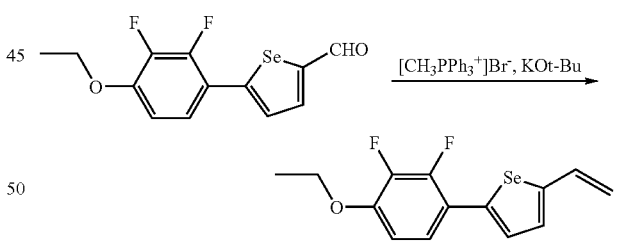

3.0 g (8.4 mmol) of methyltriphenylphosphonium bromide are initially introduced in 50 ml of THF at 0° C., and 0.89 g (7.9 mmol) of potassium tertbutoxide is dissolved in 7 ml of THF is added. After 1.5 h at RT, 2.0 g (6.4 mmol) of 5-(4-ethoxy-2,3-difluorophenyl)selenophene-2-carbaldehyde are added, and the batch is stirred for 2.5 h. The mixture is diluted with MTBE, and water and 2 N hydrochloric acid are added. The organic phase is separated off, and the aqueous phase is extracted with MTBE. The combined organic phases are washed with sat. sodium chloride soln. and dried using sodium sulfate. The solution is concentrated to dryness, and the residue is purified by column chromatography (SiO$_2$, n-heptane:EtOAc=10:1→5:1). Further purification is carried out by recrystallisation from n-heptane; 2-(4-ethoxy-2,3-difluorophenyl)-5-vinylselenophene is obtained as a yellow-orange solid.

5.3 Preparation of 2-(4-ethoxy-2,3-difluorophenyl)-5-ethylselenophene

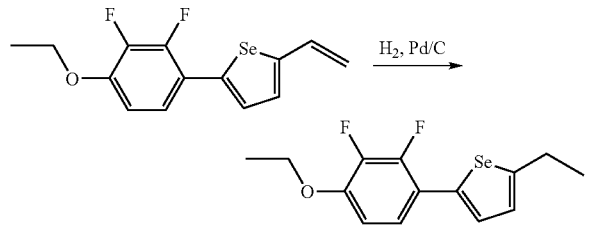

1.50 g (4.77 mmol) of 2-(4-ethoxy-2,3-difluorophenyl)-5-vinylselenophene are hydrogenated in 15 ml of ethyl acetate, in the presence of Pd/C (5% of Pd) at atmospheric pressure and RT. The reaction soln. is filtered and concentrated to dryness, and the crude product is purified by column chromatography ($SiO_2$, n-heptane:EtOAc=5:1). The further purification is carried out by recrystallisation from n-heptane. 2-(4-Ethoxy-2,3-difluorophenyl)-5-ethylselenophene is obtained as a colourless solid (m.p. 52° C.).

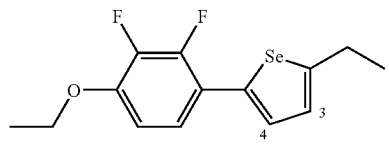

$\Delta\epsilon$=−5.2
$\Delta n$=0.1683
$\gamma_1$=37 mPa·s
C 52 I $^1$H-NMR (300 MHz, $CHCl_3$): $\delta$=7.33 (dd, 1H, J=3.3 Hz, J=0.6 Hz, 4-H), 7.17 (ddd, 1H, J=8.0 Hz, J=7.4 Hz, J=2.4 Hz, $H_{arom.}$), 6.95-6.93 (m, 1H, 3-H), 6.71 (ddd, 1H, J=8.0 Hz, J=7.4 Hz, J=2.0 Hz, $H_{arom.}$), 4.13 (q, 2H, J=7.0 Hz, $H_3CCH_2O$—), 2.92 (dq, 2H, J=7.5 Hz, J=1.2 Hz, $CH_2Me$), 1.45 (t, 3H, J=7.0 Hz, $H_3CCH_2O$—), 1.34 (t, 3H, J=7.5 Hz, $CH_2Me$).

$^{19}$F-NMR (282 MHz, $CHCl_3$): $\delta$=−138.8 (dd, 2F, J=19.3 Hz, J=8.0 Hz), −158.7 (ddd, 2F, J=19.3 Hz, J=7.4 Hz, J=2.0 Hz).

MS (EI): m/e (%)=316 (100, [M+1]$^+$), 301 (28, [M+1−Me]$^+$), 287 (39, [M+1−Et]$^+$), 273 (98).

Example 6

2-(4-Ethoxy-2,3-difluorophenyl)-5-propylselenophene

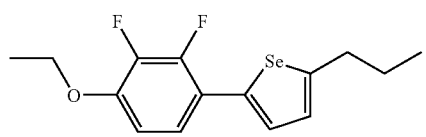

6.1 Preparation of 2-(4-ethoxy-2,3-difluorophenyl)-5-propenylselenophene

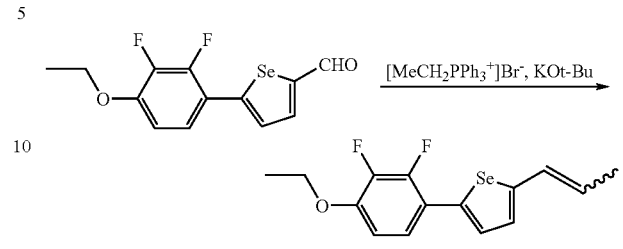

7.66 g (20.6 mmol) of ethyltriphenylphosphonium bromide are initially introduced in 80 ml of THF at 0° C., and 2.23 g (19.8 mmol) of potassium tert-butoxide dissolved in 20 ml of THF are added. After 1.5 h at RT, 5.0 g (15.9 mmol) of 5-(4-ethoxy-2,3-difluorophenyl)selenophene-2-carbaldehyde are added in portions with ice-cooling, and the batch is stirred at RT for 3.5 h. The mixture is diluted with MTBE, and water and 2 N hydrochloric acid are added. The organic phase is separated off, and the aqueous phase is extracted with MTBE. The combined organic phases are washed with sat. sodium chloride soln. and dried using sodium sulfate. The solution is concentrated to dryness, and the residue is purified by column chromatography ($SiO_2$, n-heptane:EtOAc=5:1→2:1). Further purification is carried out by recrystallisation from n-heptane; 2-(4-ethoxy-2,3-difluorophenyl)-5-propenylselenophene is obtained as a yellow solid.

6.2 Preparation of 2-(4-ethoxy-2,3-difluorophenyl)-5-propylselenophene

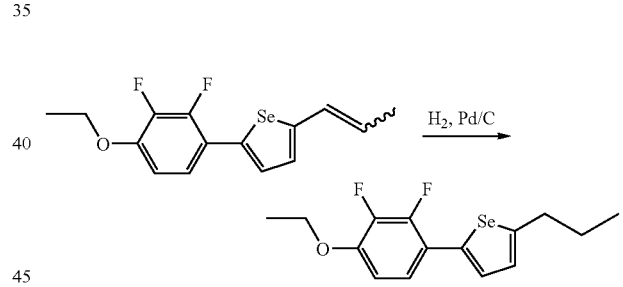

3.65 g (11.0 mmol) of 2-(4-ethoxy-2,3-difluorophenyl)-5-propenylselenophene are hydrogenated in 35 ml of ethyl acetate, in the presence of Pd/C (5% of Pd) at atmospheric pressure and RT. The reaction soln. is filtered and concentrated to dryness, and the crude product is purified by column chromatography ($SiO_2$, n-heptane:EtOAc=4:1→2:1). The further purification is carried out by recrystallisation from n-heptane. 2-(4-Ethoxy-2,3-difluorophenyl)-5-propylselenophene is obtained as a colourless solid (m.p. 64° C.).

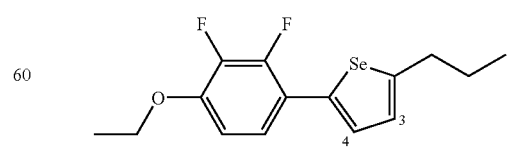

$\Delta\epsilon$=−5.0
$\Delta n$=0.1625
Cl.p.=23.4° C.

$\gamma_1$=40 mPa·s
C 64 1

$^1$H-NMR (300 MHz, CHCl$_3$): δ=7.33 (dd, 1H, J=3.8 Hz, J=0.8 Hz, 4-H), 7.17 (ddd, 1H, J=8.3 Hz, J=7.6 Hz, J=2.3 Hz, H$_{arom.}$), 6.94-6.92 (m, 1H, 3-H), 6.71 (ddd, 1H, J=8.3 Hz, J=7.6 Hz, J=2.1 Hz, H$_{arom.}$), 4.13 (q, 2H, J=6.9 Hz, H$_3$CCH$_2$O—), 2.86 (t, 2H, J=7.5 Hz, CH$_2$CH$_2$Me), 1.79-1.67 (m, 2H, CH$_2$CH$_2$Me), 1.46 (t, 3H, J=6.9 Hz, H$_3$CCH$_2$O—), 1.01 (t, 3H, J=7.4 Hz, CH$_2$CH$_2$Me).

$^{19}$F-NMR (282 MHz, CHCl$_3$): δ=−138.8 (dd, 2F, J=19.2 Hz, J=7.6 Hz), −158.7 (ddd, 2F, J=19.3 Hz, J=7.6 Hz. J=2.3 Hz).

MS (EI): m/e (%)=330 (78, [M+1]$^+$), 301 (100, [M+1−Et]$^+$), 273 (87).

Example 7

2-(4-Ethoxy-2,3-difluorophenyl)-5-butylselenophene

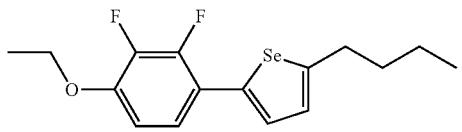

7.1 Preparation of 2-(4-ethoxy-2,3-difluorophenyl)-5-but-1-enylselenophene 14.1 g (35.0 mmol) of propyltriphenylphosphonium bromide are initially introduced in 150 ml of THF at 0° C., and 3.93 g (35.0 mmol) of potassium tert-butoxide dissolved in 50 ml of THF are added. After 1 h at this temperature, 9.0 g (28.6 mmol) of 5-(4-ethoxy-2,3-difluorophenyl)selenophene-2-carbaldehyde are added as a solution in 300 ml of THF, and the batch is stirred at RT for 19 h. Water and 2 N hydrochloric acid are added to the mixture, and the batch is extracted with MTBE. The combined organic phases are washed with sat. sodium chloride soln. and dried using sodium sulfate. The solution is concentrated to dryness, and the residue is purified by column chromatography (SiO$_2$, toluene). 2-(4-Ethoxy-2,3-difluorophenyl)-5-but-1-enylselenophene is obtained as a reddish solid.

7.2 Preparation of 2-(4-ethoxy-2,3-difluorophenyl)-5-butylselenophene

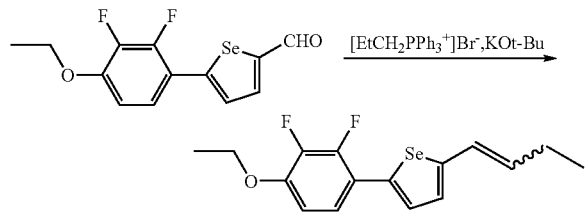

2.30 g (6.22 mmol) of 2-(4-ethoxy-2,3-difluorophenyl)-5-but-1-enylselenophene are hydrogenated in 70 ml of ethyl acetate, in the presence of Pd/C (5% of Pd) at atmospheric pressure and RT. The reaction soln. is filtered and concentrated to dryness, and the crude product is purified by recrystallisation from n-heptane. 2-(4-Ethoxy-2,3-difluorophenyl)-5-butylselenophene is obtained as a colourless solid (m.p. 47° C.).

Δε=−4.7
Δn=0.1504
$\gamma_1$=39 mPa·s
C47 1

$^1$H-NMR (400 MHz, CHCl$_3$): δ=7.33 (dd, 1H, J=3.8 Hz, J=0.8 Hz, 4-H), 7.17 (ddd, 1H, J=8.3 Hz, J=7.2 Hz, J=2.4 Hz, H$_{arom.}$), 6.93-6.91 (m, 1H, 3-H), 6.71 (ddd, 1H, J=8.3 Hz, J=7.2 Hz, J=2.4 Hz, H$_{arom.}$), 4.13 (q, 2H, J=6.9 Hz, H$_3$CCH$_2$O—), 2.89 (t, 2H, J=7.2 Hz, CH$_2$(CH$_2$)$_3$Me), 1.72-1.65 (m, 2H, H$_{aliphat.}$), 1.47-1.38 (m, 5H, H$_{aliphat.}$), 0.95 (t, 3H, J=7.5 Hz, CH$_2$(CH$_2$)$_2$Me).

$^{19}$F-NMR (376 MHz, CHCl$_3$): δ=−138.8 (dd, 1F, J=19.3 Hz, J=7.5 Hz), −158.7 (ddd, 1F, J=19.3 Hz, J=7.2 Hz, J=2.4 Hz).

MS (EI): m/e (%)=344 (97, [M+1]$^+$), 301 (100, [M+1−Pr]$^+$), 273 (83).

Example 8

2-(4-Ethoxy-2,3-difluorophenyl)-5-pentylselenophene

8.1 Preparation of 2-(4-ethoxy-2,3-difluorophenyl)-5-pent-1-enylselenophene

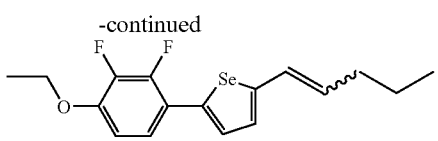

4.12 g (10.3 mmol) of butyltriphenylphosphonium bromide are initially introduced in 50 ml of THF at 0° C., and 1.04 g (9.27 mmol) of potassium tert-butoxide dissolved in 7 ml of THF are added. After 1.75 h at RT, 2.27 g (7.20 mmol) of 5-(4-ethoxy-2,3-difluorophenyl)selenophene-2-carbaldehyde are added in one portion with ice-cooling, and the batch is stirred at RT for 6 h. The mixture is diluted with MTBE, and water and 2 N hydrochloric acid are added. The organic phase is separated off, and the aqueous phase is extracted with MTBE. The combined organic phases are washed with sat. sodium chloride soln. and dried using sodium sulfate. The solution is concentrated to dryness, and the residue is purified by column chromatography (SiO$_2$, n-heptane:EtOAc=5:1-2:1). 2-(4-Ethoxy-2,3-difluorophenyl)-5-pent-1-enylselenophene is obtained as an orange oil.

8.2 Preparation of 2-(4-ethoxy-2,3-difluorophenyl)-5-pentylselenophene

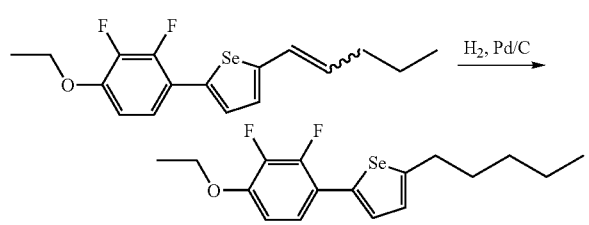

2.30 g (6.22 mmol) of 2-(4-ethoxy-2,3-difluorophenyl)-5-pent-1-enylselenophene are hydrogenated in 25 ml of ethyl acetate, in the presence of Pd/C (5% of Pd) at atmospheric pressure and RT. The reaction soln. is filtered and concentrated to dryness. The crude product is purified by column chromatography (SiO$_2$, n-heptane:EtOAc=5:1→2:1). The further purification is carried out by recrystallisation from n-heptane. 2-(4-Ethoxy-2,3-difluorophenyl)-5-pentylselenophene is obtained as a colourless solid (m.p. 66° C.).

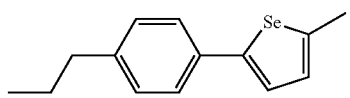

Δε=−4.7
Δn=0.1565
γ$_1$=45 mPa·s
C 66 I $^1$H-NMR (300 MHz, CHCl$_3$): δ=7.33 (d, 1H, J=3.8 Hz, 4-H), 7.17 (ddd, 1H, J=8.3 Hz, J=7.2 Hz, J=2.4 Hz, H.), 6.94-6.91 (m, 1H, 3-H), 6.71 (ddd, 1H, J=8.3 Hz, J=7.2 Hz, J=2.4 Hz, H.), 4.13 (q, 2H, J=6.9 Hz, H$_3$CCH$_2$O—), 2.88 (t, 2H, J=7.4 Hz, CH$_2$(CH$_2$)$_3$Me), 1.75-1.65 (m, 2H, H$_{aliphat.}$), 1.45 (t, 3H, J=6.9 Hz, H$_3$CCH$_2$O—), 1.42-1.34 (m, 2H, H$_{aliphat.}$), 1.34 (t, 3H, J=7.5 Hz, CH$_2$(CH$_2$)$_3$Me).

$^{19}$F-NMR (282 MHz, CHCl$_3$): δ=−138.8 (dd, 2F, J=19.3 Hz, J=7.2 Hz), −158.7 (ddd, 2F, J=19.3 Hz, J=7.2 Hz, J=2.4 Hz).

MS (EI): m/e (%)=358 (72, [M+1]$^+$), 301 (100, [M+1−Bu]$^+$), 273 (70).

Example 9

2-Methyl-5-(4-propylphenyl)selenophene

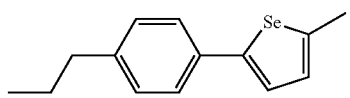

9.1 Preparation of 2-(4-propylphenyl)selenophene

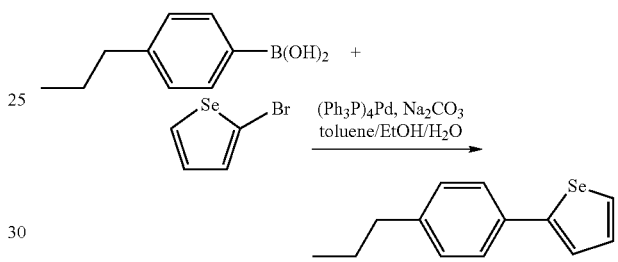

A mixture of 26.0 g (0.12 mol) of 2-bromoselenophene, 20.5 g (0.13 mol) of 4-propylphenylboronic acid, 7.0 g (6.1 mmol) of tetrakis-(triphenylphosphine)palladium(0) and 140 ml of 2 N sodium carbonate soln. in 300 ml of toluene/ethanol (1:1) is heated under reflux for 20 h. A further 7.0 g (6.06 mmol) of tetrakis(triphenylphosphine)palladium(0) are added, and the mixture is refluxed again for 3 h. After cooling, water is added, and the organic phase is separated off. The aqueous phase is extracted with toluene, and the combined organic phases are washed with water and sat. sodium chloride soln. The solution is dried using sodium sulfate and concentrated to dryness. The residue is purified by column chromatography (SiO$_2$, n-heptane). 2-(4-Propylphenyl)selenophene is obtained as a yellow liquid.

9.2 Preparation of 2-methyl-5-(4-propylphenyl)selenophene

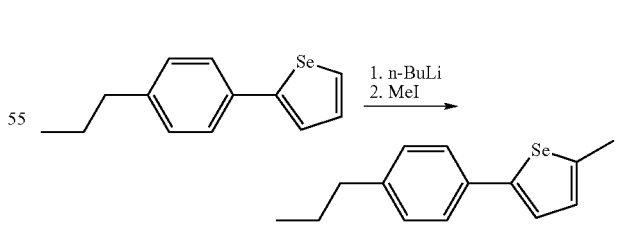

3.0 g (12.0 mmol) of 2-(4-propylphenyl)selenophene are initially introduced in 30 ml of diethyl ether, and 9.4 ml (15.0 mmol, 15% soln. in hexane) of n-BuLi are metered in rapidly. The mixture is heated under reflux for 30 min and subsequently cooled to −70° C. 3.0 ml (48.2 mol) of methyl iodide are added in one portion, and the mixture is warmed to RT and stirred for 3 h. Sat. ammonium chloride soln. and conc.

ammonia soln. are added, and the batch is stirred vigorously for a few minutes. The organic phase is separated off, and the aqueous phase is extracted with MTBE. The combined organic phases are washed with 2 N hydrochloric acid and sat. sodium chloride soln. and dried using sodium sulfate. The solution is concentrated to dryness, and the residue is purified by column chromatography (SiO$_2$, n-heptane:EtOAc=20:1→10:1→5:1). The further purification is carried out by flash chromatography (SiO$_2$ RP-18, ACN:water=9:1); 2-methyl-5-(4-propylphenyl)selenophene is obtained as a colourless solid (m.p. 31° C.).

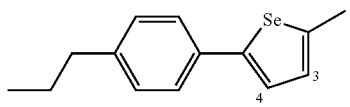

Δ∈=2.1
Δn=0.1698
γ$_1$=47 mPa·s
C 31 I $^1$H-NMR (300 MHz, CHCl$_3$): δ=7.40 (d, 2H, J=8.1 Hz, H$_{arom.}$), 7.18 (d, 1H, J=3.6 Hz, 4-H), 7.13 (d, 2H, J=8.1 Hz, H$_{arom.}$), 6.87-6.85 (m, 1H, 3-H), 2.59-2.54 (m, 5H, Me, CH$_2$CH$_2$CH$_3$), 1.70-1.58 (m, 2H, CH$_2$CH$_2$CH$_3$) 0.94 (t, 3H, J=7.4 Hz, CH$_2$CH$_2$CH$_3$).

MS (EI): m/e (%)=264 (64, [M+1]$^+$), 235 (100, [M+1−Et]$^+$).

Example 10

2-(4-Ethoxy-2,3-difluorophenyl)-5-methoxymethylselenophene

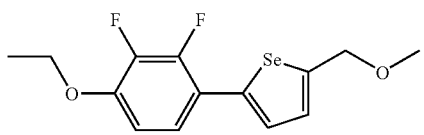

10.1 Preparation of [5-(4-ethoxy-2,3-difluorophenyl) selenophen-2-yl]-methanol

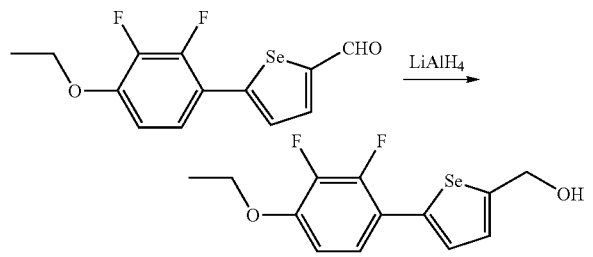

3.9 g (12.4 mmol) of 5-(4-ethoxy-2,3-difluorophenyl)selenophene-2-carbaldehyde as a suspension in 100 ml of diethyl ether are added slowly to a suspension of 0.47 g (12.4 mmol) of lithium aluminium hydride in 20 ml of diethyl ether with ice-cooling. When the addition is complete, the mixture is stirred for 5 min, and water is added dropwise to the mixture until evolution of hydrogen no longer occurs. The mixture is filtered through Celite with MTBE. The filtrate is washed with water and dried using sodium sulfate. The solution is concentrated to dryness, and the crude product (yellowish crystals) is used directly for the subsequent reaction.

10.2 Preparation of 2-(4-ethoxy-2,3-difluorophenyl)-5-methoxymethylselenophene

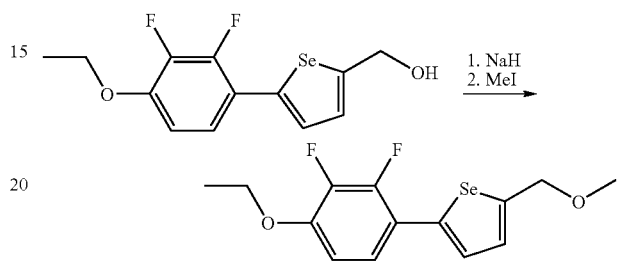

400 mg (10.0 mmol) of sodium hydride (60% suspension in paraffin oil) are washed with n-pentane and suspended in 5 ml of THF. A solution of 1.9 g (about 6.0 mmol) of crude [5-(4-ethoxy-2,3-difluorophenyl)selenophen-2-yl]methanol in 20 ml of THF is added dropwise, and the mixture is stirred for 2 h. 1.0 ml (16.1 mmol) of methyl iodide is metered in, and the batch is stirred at RT for 2 h. Water is carefully added to the reaction mixture, which is then acidified using 2 N hydrochloric acid. The mixture is extracted with MTBE, and the extract is washed with sat. sodium chloride soln. The solution is dried using sodium sulfate and concentrated to dryness. The crude product is purified by column chromatography (SiO$_2$, toluene). The further purification is carried out by recrystallisation from ethanol and MTBE. 2-(4-Ethoxy-2,3-difluorophenyl)-5-methoxymethylselenophene is obtained as a solid having an m.p. of 84° C.

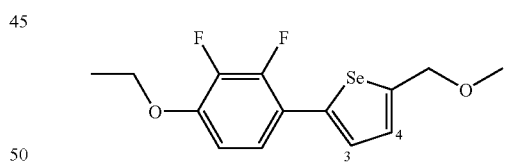

Δ∈c=−5.0
Δn=0.1521
γ$_1$=55 mPa·s
C 84 I $^1$H-NMR (300 MHz, CHCl$_3$): δ=7.39 (dd, 1H, J=3.8 Hz, J=0.8 Hz, 4-H), 7.19 (ddd, 1H, J=8.3 Hz, J=7.2 Hz, J=2.4 Hz, H$_{arom.}$), 7.14-7.11 (m, 1H, 3-H), 6.73 (ddd, 1H, J=8.3 Hz, J=7.2 Hz, J=2.4 Hz, H$_{arom.}$), 4.65 (s, 2H, CH$_2$OMe), 4.13 (q, 2H, J=6.9 Hz, H$_3$CCH$_2$O—), 3.42 (s, 3H, CH$_2$OMe), 1.46 (t, 3H, J=6.9 Hz, H$_3$CCH$_2$O—).

$^{19}$F-NMR (282 MHz, CHCl$_3$): δ=−138.5 (dd, 1F, J=19.2 Hz, J=8.3 Hz), −158.6 (ddd, 1F, J=19.2 Hz, J=7.2 Hz, J=2.4 Hz).

MS (EI): m/e (%)=332 (100, [M+1]⁺), 301 (87, [M+1−Et]⁺), 273 (82).

Example 11

2-[4-(4-Ethylcyclohexyl)-2,3-difluorophenyl]-5-methylselenophene

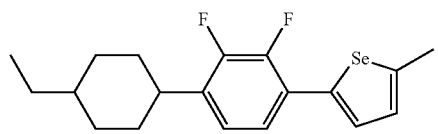

11.1 Preparation of 2-[4-(4-ethylcyclohexyl)-2,3-difluorophenyl]selenophene

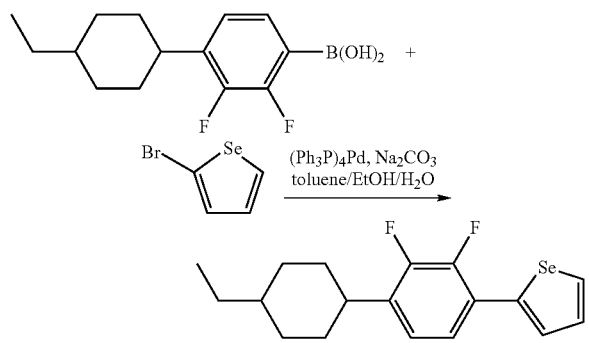

A mixture of 8.9 g (42.4 mmol) of 2-bromoselenophene, 16.0 g (59.7 mmol) of 4-(4-ethylcyclohexyl)-2,3-difluorophenylboronic acid, 3.93 g (3.40 mmol) of tetrakis(triphenylphosphine)palladium(0) and 125 ml of 2 N sodium carbonate soln. in 600 ml of toluene/ethanol (1:1) is heated under reflux for 20 h. After cooling, the organic phase is separated off, and the aqueous phase is extracted with toluene. The combined organic phases are washed with sat. sodium chloride soln., and the solution is dried using sodium sulfate. The solution is concentrated to dryness, and the residue is purified by column chromatography (SiO₂, toluene). The further purification is carried out by recrystallisation from n-heptane:EtOH=1:1 and IPA. 2-[4-(4-Ethylcyclohexyl)-2,3-difluorophenyl]selenophene is obtained as a pale-yellowish solid.

11.2 Preparation of 2-[4-(4-ethylcyclohexyl)-2,3-difluorophenyl]-5-methylselenophene

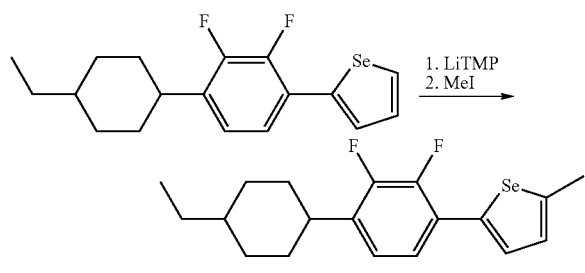

2.2 ml (13.0 mmol) of TMP are initially introduced at −15° C. in 15 ml of diethyl ether, and 8.2 ml (13.0 mmol, 15% soln. in hexane) of n-BuLi are metered in. After 25 min, a solution of 3.5 g (9.9 mmol) of 2-[4-(4-ethyl-cyclohexyl)-2,3-difluorophenyl]selenophene in 35 ml of diethyl ether is metered in at 0° C., and the mixture is stirred at RT for 2 h. The batch is cooled to −70° C., and 3.0 ml (48.2 mmol) of methyl iodide are added. The mixture is warmed to RT and stirred for 24 h. Sat. ammonium chloride soln. and conc. ammonia soln. are added successively, and the mixture is briefly stirred vigorously. The organic phase is separated off, and the aqueous phase is extracted with MTBE. The combined organic phases are washed with 2 N hydrochloric acid and sat. sodium chloride soln. and dried using sodium sulfate. The solution is concentrated to dryness, and the residue is purified by column chromatography (SiO₂, n-heptane). The further purification is carried out by recrystallisation from ethanol. 2-[4-(4-Ethylcyclohexyl)-2,3-difluorophenyl]-5-methylselenophene is obtained as a solid having an m.p. of 63° C.

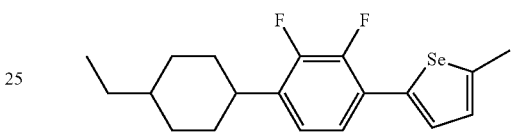

$\Delta\varepsilon = -3.5$
$\Delta n = 0.1746$
$\gamma_1 = 227$ mPa·s
C 63 N 95 I $^{1}$H-NMR (300 MHz, CHCl₃): δ=7.38 (d, 1H, J=3.9 Hz, H$_{seleno.}$), 7.22-7.16 (m, 1H, H$_{arom.}$), 6.95-6.90 (m, 2H, H$_{arom.}$), 2.87-2.76 (m, 1H, H$_{aliph.}$), 2.59 (d, 3H, J=1.0 Hz, Me$_{seleno.}$), 1.88 (dm, 4H, J=10.8 Hz, H$_{aliph.}$), 1.53-1.40 (m, 2H, H$_{aliph.}$), 1.32-1.16 (m, 3H, H$_{aliph.}$), 1.13-1.00 (m, 2H, H$_{aliph.}$), 0.91 (t, 3H, J=7.2 Hz, CH₂CH₃).
$^{19}$F-NMR (282 MHz, CHCl₃): δ=−144.4 (dd, 1F, J=19.9 Hz, J=6.5 Hz), −141.0 (dd, 1F, J=19.9 Hz, J=6.9 Hz).
MS (EI): m/e (%)=368 (100, [M+1]⁺).

Example 12

2-(2',3'-Difluoro-4'-propoxybiphenyl-4-yl)-5-methylselenophene

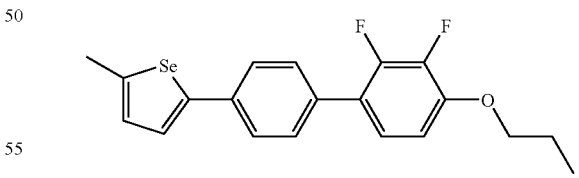

12.1 Preparation of 2-(2',3'-difluoro-4'-propoxybiphenyl-4-yl)selenophene

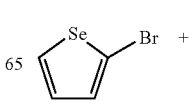 +

-continued

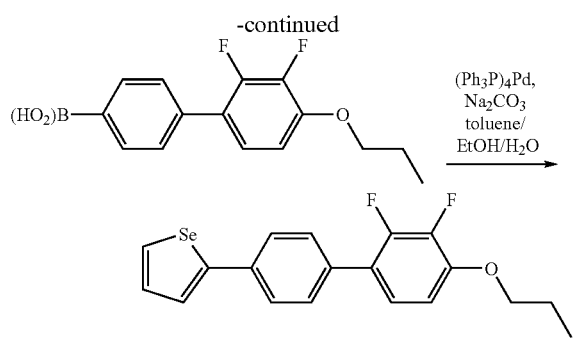

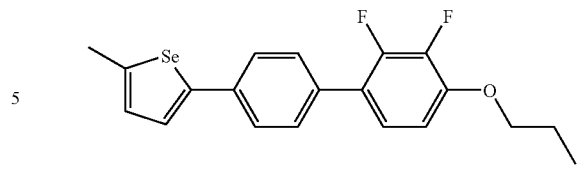

A mixture of 12.7 g (60.6 mmol) of 2-bromoselenophene, 17.7 g (60.6 mmol) of 2',3'-difluoro-4'-propoxybiphenyl-4-ylboronic acid, 5.55 g (4.80 mmol) of tetrakis(triphenylphosphine)palladium(0) and 180 ml of 2 N sodium carbonate soln. in 600 ml of toluene/ethanol (1:1) is heated under reflux for 20 h. After cooling, the organic phase is separated off, and the aqueous phase is extracted with toluene. The combined organic phases are washed with sat. sodium chloride soln., and the solution is dried using sodium sulfate. The solution is concentrated to dryness, and the residue is purified by column chromatography (SiO$_2$, toluene). Further purification is carried out by recrystallisation from n-heptane:EtOH=3:1. 2-(2',3'-Difluoro-4'-propoxybiphenyl-4-yl)selenophene is obtained as a yellow solid.

$\Delta\varepsilon$=−5.6
$\Delta$n=0.2768
$\gamma_1$=387 mPa·s
C 143 N 171 I $^1$H-NMR (300 MHz, CHCl$_3$): $\delta$=7.55 (d, 2H, J=8.4 Hz, H$_{arom.}$), 7.48 (dd, 2H, J=8.4 Hz, J=1.5 Hz, H$_{arom.}$), 7.29 (d, 1H, J=3.9 Hz, H$_{arom.}$), 6.92-6.90 (m, 1H, H$_{arom.}$), 6.83-6.77 (m, 1H, H$_{arom.}$), 4.04 (t, 2H, J=6.6 Hz, OCH$_2$CH$_2$CH$_3$), 2.60 (d, 3H, J=1.0 Hz, Me$_{seleno.}$), 1.93-1.81 (m, 2H, OCH$_2$CH$_2$CH$_3$), 1.07 (t, 3H, J=7.4 Hz, OCH$_2$CH$_2$CH$_3$).

$^{19}$F-NMR (282 MHz, CHCl$_3$): $\delta$=−158.7 (ddd, 1F, J=19.6 Hz, J=7.5 Hz, J=2.1 Hz), −141.6 (ddd, 1F, J=19.6 Hz, J=8.0 Hz, J=1.4 Hz).

MS (EI): m/e (%)=392 (100, [M+1]$^+$), 349 (93, [M+1−Pr]$^+$).

Example 13

2-(2',3'-Difluoro-4'-propoxybiphenyl-4-yl)-5-ethylselenophene

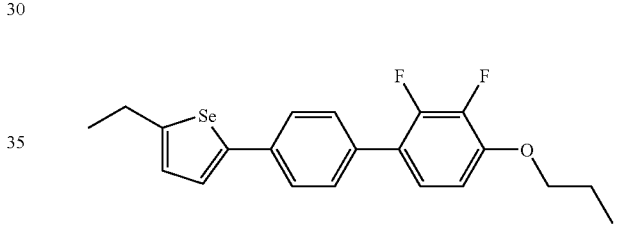

12.2 Preparation of 2-(2',3'-difluoro-4'-propoxybiphenyl-4-yl)-5-methylselenophene

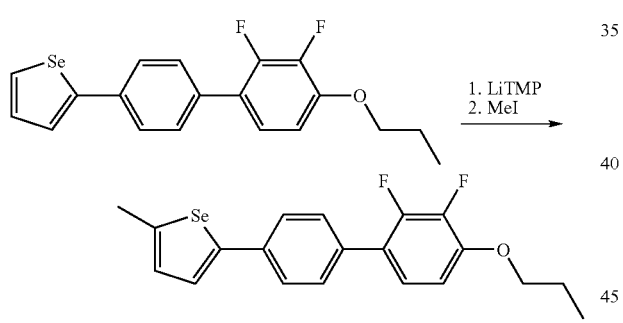

2.0 ml (11.8 mmol) of TMP are initially introduced at −15° C. in 15 ml of diethyl ether, and 7.0 ml (11.1 mmol, 15% soln. in hexane) of n-BuLi are metered in. After 25 min, a solution of 3.5 g (9.3 mmol) of 2-(2',3'-difluoro-4'-propoxybiphenyl-4-yl)selenophene in 35 ml of diethyl ether is metered in, and the mixture is stirred at RT for 45 min. The batch is cooled to −70° C., and 3.0 ml (48.2 mmol) of methyl iodide are added. The mixture is warmed to RT and stirred for 3 h. Sat. ammonium chloride soln. and conc. ammonia soln. are added successively, and the mixture is briefly stirred vigorously. The organic phase is separated off, and the aqueous phase is extracted with MTBE. The combined organic phases are washed with 2 N hydrochloric acid and sat. sodium chloride soln. and dried using sodium sulfate. The solution is concentrated to dryness, and the residue is purified by column chromatography (SiO$_2$, n-heptane:toluene=1:1). The further purification is carried out by digestion in ethanol and recrystallisation from n-heptane/toluene (2:1). 2-(2',3'-Difluoro-4'-propoxybiphenyl-4-yl)-5-methylselenophene is obtained as a solid having an m.p. of 143° C.

13.1 Preparation of 5-(2',3'-difluoro-4'-propoxybiphenyl-4-yl)selenophene-2-carbaldehyde

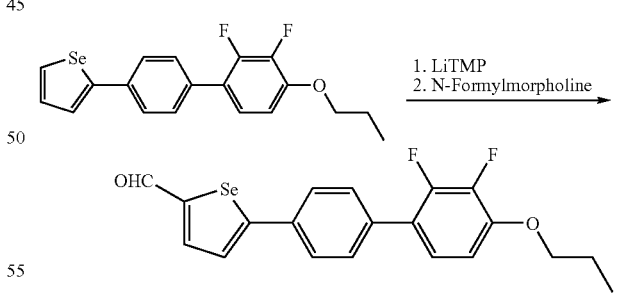

5.5 ml (32.3 mmol) of TMP are initially introduced at −20° C. in 50 ml of THF, and 20.0 ml (31.8 mmol, 15% soln. in hexane) of n-BuLi are metered in. The mixture is warmed to 5° C., and a solution of 10.0 g (26.5 mmol) of 2-(2',3'-difluoro-4'-propoxybiphenyl-4-yl)selenophene in 100 ml of THF is metered in. The batch is warmed to RT and stirred for 30 min. The mixture is cooled to −70° C., and 3.5 ml (35.0 mmol) of N-formylmorpholine are added. The reaction mixture is warmed to RT and stirred for 1 h. 2 N hydrochloric acid is added, and the batch is added to 1 l of water. The solid forming is filtered off and crystallised from toluene, giving 5-(2',3'-difluoro-4'-propoxybiphenyl-4-yl)selenophene-2-carbaldehyde as a brown solid.

13.2 Preparation of 2-(2',3'-difluoro-4'-propoxybiphenyl-4-yl)-5-vinylselenophene

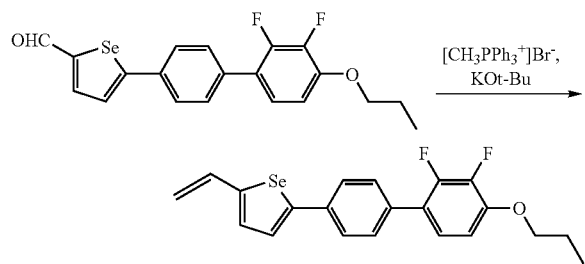

4.50 g (12.6 mmol) of methyltriphenylphosphonium bromide are initially introduced in 50 ml of THF at 0° C., and 1.40 g (12.5 mmol) of potassium tert-butoxide dissolved in 30 ml of THF are added. After 1 h, 4.1 g (10.1 mmol) of 5-(2',3'-difluoro-4'-propoxybiphenyl-4-yl)selenophene-2-carbaldehyde in 100 ml of THF are added, and the batch is stirred at RT for 17 h. Water and 2 N hydrochloric acid are added to the mixture, and the batch is extracted with MTBE. The combined organic phases are washed with sat. sodium chloride soln. and dried using sodium sulfate. The solution is concentrated to dryness, and the residue is purified by column chromatography (SiO$_2$, toluene). 2-(2',3'-Difluoro-4'-propoxy-biphenyl-4-yl)-5-vinylselenophene is obtained as an orange solid.

13.3 Preparation of 2-(2',3'-difluoro-4'-propoxybiphenyl-4-yl)-5-ethylselenophene

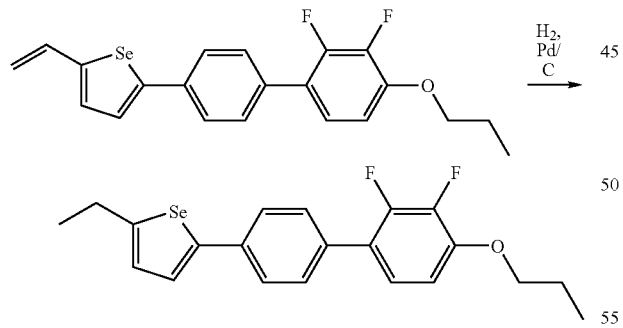

3.0 g (5.0 mmol) of 2-(2',3'-difluoro-4'-propoxybiphenyl-4-yl)-5-vinylselenophene are hydrogenated in 90 ml of ethyl acetate/toluene (2:1), in the presence of Pd/C (5% of Pd) at atmospheric pressure and RT. The reaction soln. is filtered and concentrated to dryness. The crude product is purified by column chromatography (SiO$_2$, n-heptane:toluene=2:1). The further purification is carried out by recrystallisation from n-heptane. 2-(2',3'-Difluoro-4'-propoxybiphenyl-4-yl)-5-ethylselenophene is obtained as a solid having an m.p. of 126° C.

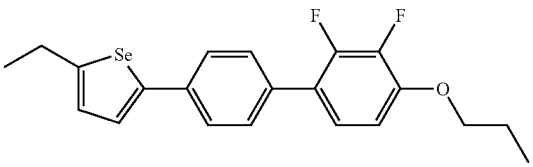

$\Delta\varepsilon=-5.4$
$\Delta n=0.2684$
$\gamma_1=271$ mPa·s
C 126 N 156 I $^1$H-NMR (300 MHz, CHCl$_3$): δ=7.57 (d, 2H, J=8.6 Hz, H$_{arom.}$), 7.48 (dd, 2H, J=8.6 Hz, J=1.5 Hz, H$_{arom.}$), 7.31 (d, 1H, J=3.9 Hz, H$_{seleno.}$), 7.15-7.08 (m, 1H, H$_{arom.}$), 6.97-6.94 (m, 1H, H$_{arom.}$), 6.84-6.77 (m, 1H, H$_{arom.}$), 4.05 (t, 2H, J=6.7 Hz, OCH$_2$CH$_2$CH$_3$), 2.93 (dq, 2H, J=7.4 Hz, J=1.0 Hz, CH$_2$Me$_{seleno.}$), 1.93-1.81 (m, 2H, OCH$_2$CH$_2$CH$_3$), 1.35 (t, 3H, J=7.5 Hz, CH$_2$Me$_{seleno.}$), 1.07 (t, 3H, J=7.5 Hz, OCH$_2$CH$_2$CH$_3$).

$^{19}$F-NMR (282 MHz, CHCl$_3$): δ=−158.7 (ddd, 1F, J=19.8 Hz, J=7.5 Hz, J=2.0 Hz), −141.6 (ddd, 1F, J=19.8 Hz, J=8.1 Hz, J=1.4 Hz).

MS (EI): m/e (%)=406 (100, [M+1]$^+$).

Example 14

2-(2',3'-Difluoro-4'-propoxybiphenyl-4-yl)-5-propylselenophene

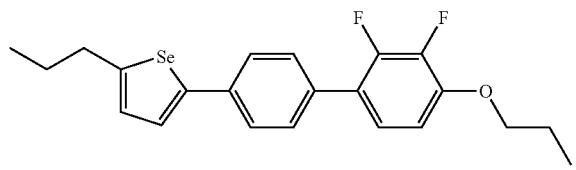

14.1 Preparation of 2-(2',3'-difluoro-4'-propoxybiphenyl-4-yl)-5-propenylselenophene

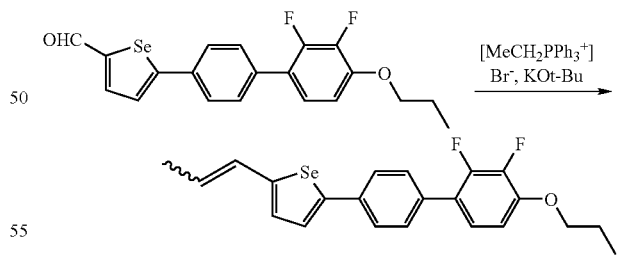

4.70 g (12.5 mmol) of ethyltriphenylphosphonium bromide are initially introduced in 50 ml of THF at 0° C., and 1.40 g (12.5 mmol) of potassium tert-butoxide dissolved in 30 ml of THF are added. After 1 h, 4.2 g (10.4 mmol) of 5-(2',3'-difluoro-4'-propoxybiphenyl-4-yl)selenophene-2-carbaldehyde in 100 ml of THF are added, and the batch is stirred at RT for 18 h. Water and 2 N hydrochloric acid are added to the mixture, and the batch is extracted with MTBE. The combined organic phases are washed with sat. sodium chloride soln. and dried using sodium sulfate. The solution is concen-

14.2 Preparation of 2-(2',3'-difluoro-4'-propoxybi-phenyl-4-yl)-5-propylselenophene

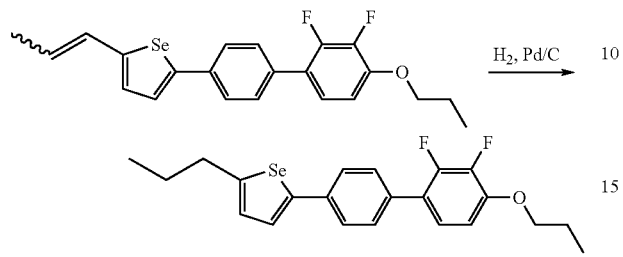

0.7 g (1.7 mmol) of 2-(2',3'-difluoro-4'-propoxybiphenyl-4-yl)-5-propenyl-selenophene is hydrogenated in 30 ml of ethyl acetate/toluene (2:1), in the presence of Pd/C (5% of Pd) at atmospheric pressure and RT. The reaction soln. is filtered and concentrated to dryness. Recrystallisation from n-heptane/toluene (4:1) gives 2-(2',3'-difluoro-4'-propoxybiphenyl-4-yl)-5-propylselenophene as a solid having an m.p. of 114° C.

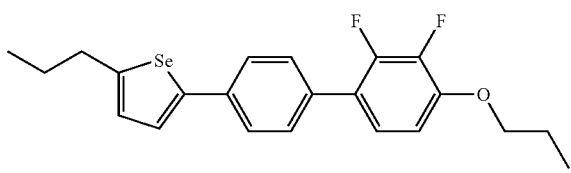

$\Delta\varepsilon = -4.8$
$\Delta n = 0.2587$
$\gamma_1 = 245$ mPa·s
C 114 N 153 I $^1$H-NMR (300 MHz, CHCl$_3$): δ=7.57 (d, 2H, J=8.6 Hz, H$_{arom.}$), 7.48 (dd, 2H, J=8.6 Hz, J=1.5 Hz, H$_{arom.}$), 7.30 (d, 1H, J=3.9 Hz, H$_{seleno.}$), 7.15-7.08 (m, 1H, H$_{arom.}$), 6.97-6.94 (m, 1H, H$_{arom.}$), 6.84-6.77 (m, 1H, H$_{arom.}$), 4.05 (t, 2H, J=6.7 Hz, OCH$_2$CH$_2$CH$_3$), 2.87 (dt, 2H, J=7.5 Hz, J=1.0 Hz, CH$_2$CH$_2$Me$_{seleno.}$), 1.93-1.82 (m, 2H, OCH$_2$CH$_2$CH$_3$), 1.80-1.68 (m, 2H, CH$_2$CH$_2$Me$_{seleno.}$), 1.10-0.99 (m, 6H, OCH$_2$CH$_2$CH$_3$, CH$_2$CH$_2$Me$_{seleno.}$).

$^{19}$F-NMR (282 MHz, CHCl$_3$): δ=−158.7 (ddd, 1F, J=19.8 Hz, J=7.5 Hz, J=2.0 Hz), −141.6 (ddd, 1F, J=19.8 Hz, J=8.1 Hz, J=1.4 Hz).

MS (EI): m/e (%)=420 (100, [M+1]$^+$).

Example 15

2-(3-Fluoro-4'-propylbiphenyl-4-yl)-5-methylselenophene

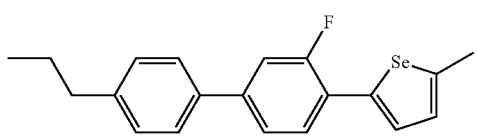

15.1 Preparation of 2-(3-fluoro-4'-propylbiphenyl-4-yl)selenophene

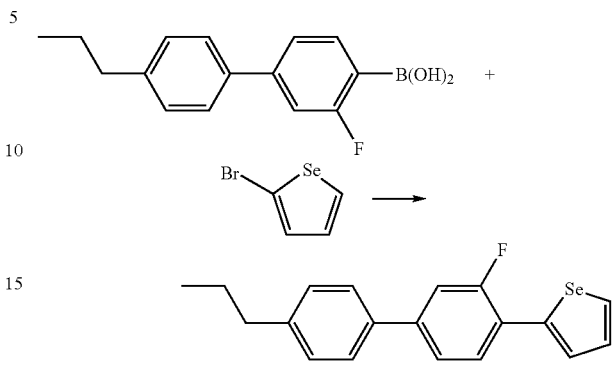

A mixture of 15.0 g (71.5 mmol) of 2-bromoselenophene, 471 mg (0.67 mmol) of bis(triphenylphosphine)palladium(II) chloride, 84 mg (1.34 mmol) of hydrazine hydrate (80%) and 50 ml (50.0 mmol) of aqueous sodium metaborate soln. (1 M) is heated to 60° C. A soln. of 19.1 g (74.0 mmol) of 3-fluoro-4'-propylbiphenyl-4-ylboronic acid in 70 ml of THF is slowly metered in, and the batch is stirred at this temperature for 3 h. After cooling, the mixture is diluted with n-heptane, and the organic phase is separated off. The aqueous phase is extracted with n-heptane, and the combined organic phases are dried using sodium sulfate. The solution is concentrated, and the precipitate forming is filtered off. The residue is purified by column chromatography (SiO$_2$, toluene).

15.2 Preparation of 2-(3-fluoro-4'-propylbiphenyl-4-yl)-5-methylselenophene

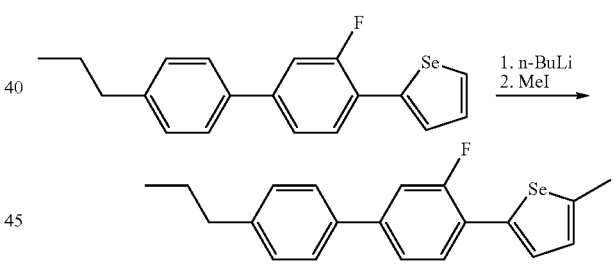

3.5 ml (20.6 mmol) of TMP are initially introduced at −20° C. in THF, and 7.7 ml (19.3 mmol, 2.5 M in hexane) of n-HexLi are metered in. After 25 min at this temperature, a solution of 5.5 g (16.0 mmol) of 2-(3-fluoro-4'-propylbiphenyl-4-yl)selenophene in 50 ml of THF is added. When the addition is complete, the batch is warmed to RT over the course of 45 min and left at this temperature for 20 min. The solution is cooled to −70° C., and 13.6 g (95.8 mmol) of methyl iodide are added. The reaction mixture is warmed to RT and stirred for 20 h. The solution is diluted with MTBE, and sat. ammonium chloride soln. and conc. ammonia soln. are added successively. The mixture is stirred vigorously for a few minutes, and the organic phase is separated off. The aqueous phase is extracted with MTBE, and the combined organic phases washed successively with water, 2 N hydrochloric acid and sat. sodium chloride soln. The solution is dried using sodium sulfate and concentrated to dryness. The crude product is purified by chromatography. The further purification is carried out by recrystallisation from n-heptane.

2-(3-Fluoro-4'-propylbiphenyl-4-yl)-5-methylselenophene is obtained as a solid having an m.p. of 97° C.

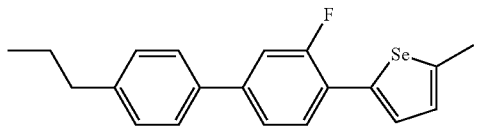

Δ∈=4.0

Δn=0.3080

γ₁=189 mPa·s

C 97 N 162 I

¹H-NMR (300 MHz, CHCl₃): δ=7.61-7.56 (m, 1H, H$_{seleno.}$), 7.51 (d, 2H, J=8.4 Hz, H$_{arom.}$), 7.46 (d, 1H, J=3.8 Hz, H$_{seleno.}$), 7.38-7.36 (m, 1H, H$_{atom.}$), 7.33 (dd, 1H, J=7.1 Hz, J=1.7 Hz, H$_{arom.}$), 7.25 (d, 2H, J=8.4 Hz, H$_{arom.}$), 6.95-6.93 (m, 1H, 3-H), 2.66-2.61 (m, 5H, CH₂CH₂CH₃, Me$_{seleno.}$), 1.74-1.62 (m, 2H, CH₂CH₂CH₃), 0.97 (t, 3H, J=7.4 Hz, CH₂CH₂CH₃).

¹⁹F-NMR (282 MHz, CHCl₃): δ=−114.6 (dd, 1F, J=13.5 Hz, J=8.2 Hz).

MS (EI): m/e (%)=358 (94, [M+1]⁺), 329 (100, [M+1−Et]⁺).

Example 16

2-(3-Fluoro-4'-propylbiphenyl-4-yl)-5-propylselenophene

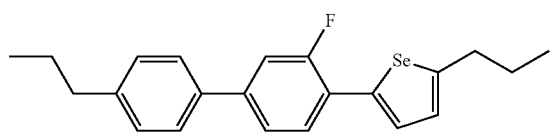

16.1 Preparation of 2-formylselenophene

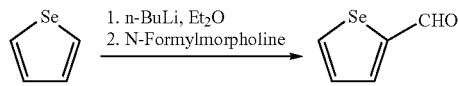

30.0 g (0.23 mol) of selenophene are initially introduced in 300 ml of diethyl ether, and 142 ml (0.23 mol, 15% soln. in hexane) of n-BuLi are metered in rapidly. The mixture is heated under reflux for 1 h and subsequently cooled to 0° C. 31.3 g (0.27 mol) of N-formylmorpholine added, and the mixture is stirred at this temperature for 1 h. The batch is warmed to RT and stirred for 19 h. 250 ml of water are added, and the mixture is acidified using 2 N hydrochloric acid. The organic phase is separated off, and the aqueous phase is extracted with diethyl ether. The combined organic phases are washed a number of times with water and dried using sodium sulfate. The solvents are removed under reduced pressure, and the crude product obtained in this way is used directly for the subsequent reaction.

16.2 Preparation of 2-propenylselenophene

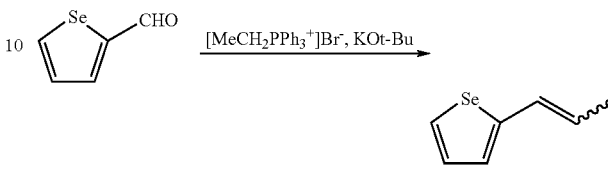

100.5 g (0.27 mol) of ethyltriphenylphosphonium bromide are initially introduced in 300 ml of THF at 0° C., and 29.8 g (0.26 mmol) of potassium tert-butoxide dissolved in 100 ml of THF added. After 1 h, 32.8 g (about 0.21 mol) of crude 2-formylselenophene in 80 ml of THF added, and the batch is stirred at RT for 17 h. Water and 2 N hydrochloric acid are added to the mixture, and the batch is extracted with MTBE. The aqueous phase is extracted with diethyl ether, and the combined organic phases are washed with sat. sodium chloride soln. and dried using sodium sulfate. The solution is concentrated, and n-heptane is added to the residue. Insoluble constituents are filtered off, and the filtrate is concentrated to dryness. The residue is purified by column chromatography (SiO₂, n-heptane). 2-Propenylselenophene is obtained as a yellowish liquid.

16.3 Preparation of 2-propylselenophene

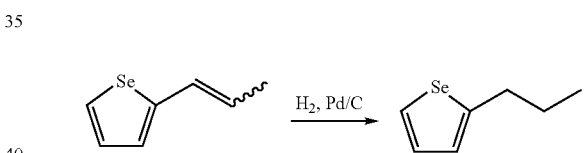

22.3 g (0.13 mol) of 2-propenylselenophene are hydrogenated in 200 ml ethyl acetate, in the presence of Pd/C (5% of Pd) at atmospheric pressure and RT. The reaction solution is filtered and concentrated to dryness. The crude product obtained in this way is used directly for the subsequent reaction.

16.4 Preparation of 2-bromo-5-propylselenophene

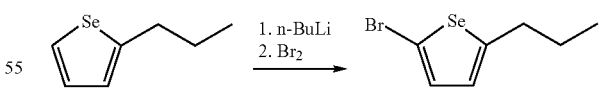

24.3 g (about 0.97 mol) of crude 2-propylselenophene are initially introduced in 100 ml of diethyl ether, and 64.5 ml (0.10 mol, 15% soln. in hexane) of n-BuLi are rapidly metered. The mixture is heated under reflux for 1 h and subsequently cooled to −70° C. 16.5 g (0.10 mol) of bromine are added, and the batch is stirred for 1 h at 0° C. and for 3 h at RT. The mixture is added to semi-conc. sodium hydrogensulfite soln., and the organic phase is separated off. The aqueous phase is extracted with MTBE, and the combined organic phases are washed with sat. sodium chloride soln. The solution is dried using sodium sulfate and concentrated to dryness. The residue is purified by vacuum distillation.

16.5 Preparation of 2-(3-fluoro-4'-propylbiphenyl-4-yl)-5-propylselenophene

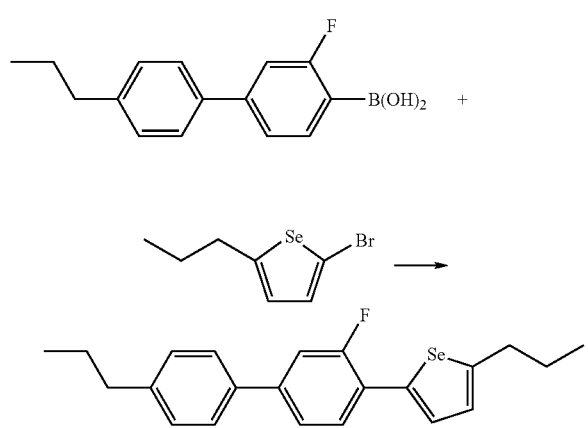

A mixture of 2.0 g (7.33 mmol) of 2-bromoselenophene (purity 92%), 51 mg (0.07 mmol) of bis(triphenylphosphine)palladium(II) chloride, 10 µl (0.2 mmol) of hydrazine hydrate (80%) and 5 ml (5.0 mmol) of aqueous sodium metaborate soln. (1 M) is heated to 60° C. A soln. of 2.11 g (8.1 mmol) of 3-fluoro-4'-propylbiphenyl-4-ylboronic acid in 6 ml of THF is slowly metered in, and the batch is stirred at this temperature for 3 h. After cooling, the mixture is diluted with n-heptane, and the organic phase is separated off. The aqueous phase is extracted with n-heptane, and the combined organic phases are dried using sodium sulfate. The solution is concentrated, and the precipitate forming is filtered off. The residue is purified by column chromatography (SiO$_2$, n-heptane). The further purification is carried out by recrystallisation from n-heptane and from ethanol.

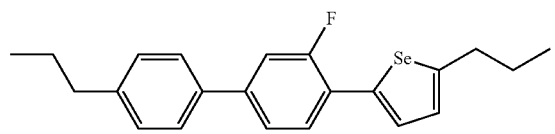

Δε=2.5

Δn=0.291

γ$_1$=127 mPa·s

C 89 SmA 104 N 147 I $^1$H-NMR (300 MHz, CHCl$_3$): δ=7.61-7.56 (m, 1H, H$_{seleno.}$), 7.51 (d, 2H, J=8.3 Hz, H$_{arom.}$), 7.48 (d, 1H, J=3.9 Hz, H$_{seleno.}$), 7.38-7.36 (m, 1H, H$_{arom.}$), 7.33 (dd, 1H, J=5.7 Hz, J=1.4 Hz, H$_{arom.}$), 7.27-7.23 (m, 2H, J=8.4 Hz, H$_{arom.}$), 6.97-6.95 (m, 1H, 3-H), 2.88 (t, 2H, J=7.2 Hz, CH$_2$CH$_2$CH$_3$), 2.63 (t, 2H, J=7.7 Hz, CH$_2$CH$_2$CH$_3$), 1.80-1.61 (m, 4H, 2 CH$_2$CH$_2$CH$_3$), 1.02 (t, 3H, J=7.3 Hz, CH$_2$CH$_2$CH$_3$), 0.97 (t, 3H, J=7.4 Hz, CH$_2$CH$_2$CH$_3$).

$^{19}$F-NMR (282 MHz, CHCl$_3$): δ=-114.6 (dd, 1F, J=13.3 Hz, J=8.3 Hz).

MS (EI): m/e (%)=385 (69, M$^+$), 356 (100, [M+1−Et]$^+$).

Example 17

2-Methyl-5-(4'-propylbicyclohexyl-3-en-4-yl)selenophene

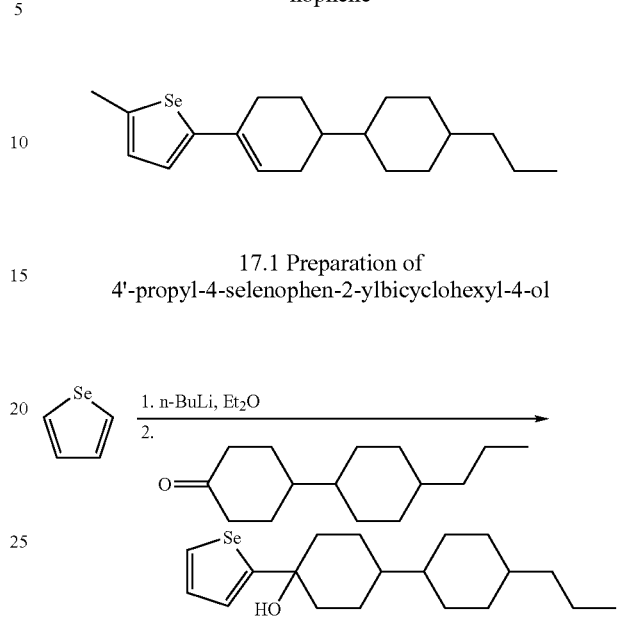

17.1 Preparation of 4'-propyl-4-selenophen-2-ylbicyclohexyl-4-ol 25.0 g (0.19 mol) of selenophene are initially introduced in 250 ml of diethyl ether, and 130 ml (0.21 mol, 15% soln. in hexane) of n-BuLi are added. The mixture is warmed under reflux for 25 min and subsequently cooled to −50° C. A solution of 46.7 g (0.21 mol) of 4'-propylbicyclohexyl-4-one in 70 ml of diethyl ether is metered in, and the mixture is slowly warmed to RT. After 18 h, sat. ammonium chloride soln. and 2 N hydrochloric acid are added, and the organic phase is separated off. The aqueous phase is extracted with diethyl ether, and the combined organic phase is washed with 1 N hydrochloric acid and sat. sodium chloride soln. The solution is dried using sodium sulfate and concentrated to dryness. The residue is purified by column chromatography (SiO$_2$, n-heptane:EtOAc=3:1→2:1). Further purification is carried out by recrystallisation from n-heptane. 4'-Propyl-4-selenophen-2-ylbicyclohexyl-4-ol is obtained as a yellow-brown solid.

17.2 Preparation of 2-(4'-propylbicyclohexyl-3-en-4-yl)selenophene

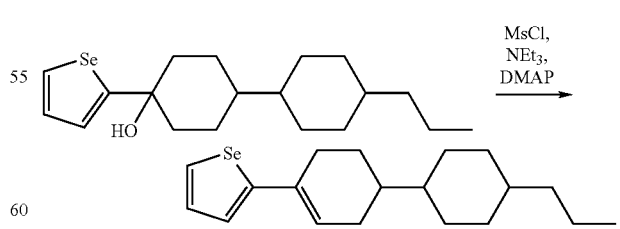

27.1 g (76.7 mmol) of 4'-propyl-4-selenophen-2-ylbicyclohexyl-4-ol are initially introduced together with 300 ml (2.2 mol) of triethylamine and 2.1 g of DMAP (17.2 mmol) in 800 ml of dichloromethane, and 67.0 ml (0.86 mol) of methanesulfonyl chloride are added slowly with ice-cooling.

When the addition is complete, the mixture is stirred firstly for 30 min at 0° C. and subsequently for 3.5 h at RT. The reaction mixture is washed a number of times with water, and the combined aqueous phases are extracted with dichloromethane. The combined organic phases are washed with hydrochloric acid and water. The solution is dried using sodium sulfate and concentrated to dryness. The crude product is purified by column chromatography (SiO₂, n-heptane→n-heptane:EtOAc=20:1). 2-(4'-Propylbicyclohexyl-3-en-4-yl)selenophene is obtained as a yellow solid.

17.3 Preparation of 2-methyl-5-(4'-propylbicyclohexyl-3-en-4-yl)selenophene

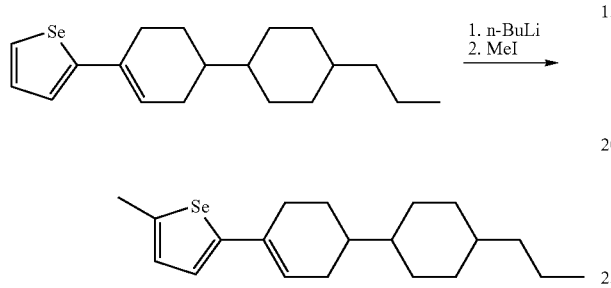

5.0 g (14.9 mmol) of 2-(4'-propylbicyclohexyl-3-en-4-yl)selenophene are initially introduced in 75 ml of diethyl ether/THF (2:1), and 12.0 ml (19.1 mmol, 15% soln. in hexane) of n-BuLi are metered in rapidly. The mixture is heated under reflux for 30 min and subsequently cooled to −70° C. 4.0 ml (64.3 mmol) of methyl iodide are added, and the batch is stirred for 18 h with slow thawing to RT. Sat. ammonium chloride soln. and conc. ammonia soln. are added successively, and the mixture is stirred vigorously for a few minutes. The organic phase is separated off, and the aqueous phase is extracted with diethyl ether. The combined organic phases are washed with water, 2 N hydrochloric acid and sat. sodium chloride soln. The solution is dried using sodium sulfate and concentrated to dryness. The crude product is purified by column chromatography (SiO₂, n-heptane→4 n-heptane:EtOAc=25:1). The further purification is carried out by recrystallisation from n-heptane. 2-Methyl-5-(4'-propylbicyclohexyl-3-en-4-yl)selenophene is obtained as a colourless solid (m.p. 111° C.).

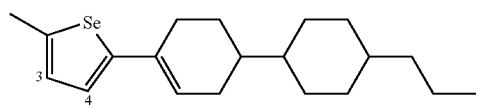

Δ∈=2.9

Δn=0.1413

$\gamma_1$=502 mPa·s

C 111 SmA 137 N 174 I

¹H-NMR (300 MHz, CHCl₃): δ=6.81 (d, 1H, J=3.6 Hz, 4-H), 6.73 (dd, 1H, J=3.6 Hz, J=1.2 Hz, 3-H), 5.97-5.93 (m, 1H, H$_{vinylic.}$), 2.53-2.45 (m, 4H, Me$_{selenophene}$, H$_{aliph.}$), 2.39-2.27 (m, 1H, H$_{aliph.}$), 2.24-2.13 (m, 1H, H$_{aliph.}$), 1.95-1.71 (m, 7H, H$_{aliph.}$), 1.41-1.24 (m, 4H, H$_{aliph.}$), 1.20-1.11 (m, 4H, H$_{aliph.}$), 1.08-0.93 (m, 2H, H$_{aliph.}$), 0.91-0.79 (m, 4H, H$_{aliph.}$).

MS (EI): m/e (%)=350 (100, [M+1]⁺).

Example 18

2-Methyl-5-(4'-propylbicyclohexyl-4-yl)selenophene

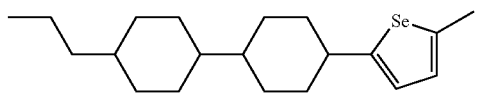

18.1 Preparation of 2-(4'-propylbicyclohexyl-4-yl)selenophene

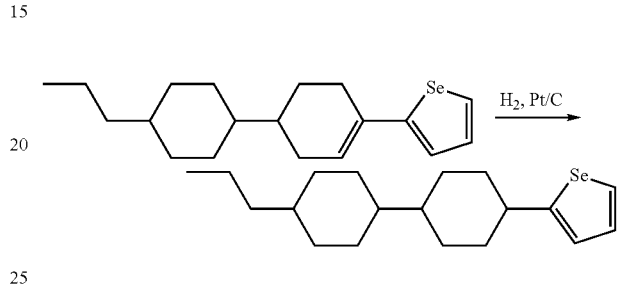

7.18 g (20.6 mmol) of 2-(4'-propylbicyclohexyl-3-en-4-yl)selenophene are hydrogenated in the presence of Pt/C (5% of Pt) at 90° C. and 8 bar of hydrogen. The solution is filtered and concentrated to dryness. The residue is warmed at 80° C. for 18 h in 120 ml of NMP together with 717 mg (6.39 mmol) of potassium tert-butoxide. The mixture is diluted with MTBE and washed successively with water, 2 N hydrochloric acid and sat. sodium chloride soln. The organic phase is dried using sodium sulfate and concentrated to dryness. The crude product is purified by column chromatography (SiO₂, n-heptane:EtOAc=95:5). The further purification is carried out by recrystallisation from IPA/n-heptane (20:1). 2-(4'-Propylbicyclohexyl-4-yl)selenophene is obtained as a colourless solid.

18.2 Preparation of 2-methyl-5-(4'-propylbicyclohexyl-4-yl)selenophene

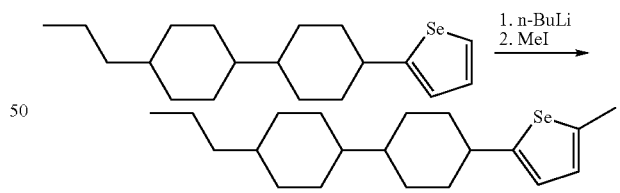

2.0 g (5.9 mmol) of 2-(4'-propylbicyclohexyl-4-yl)selenophene are initially introduced in 20 ml of diethyl ether, and 5.0 ml (8.0 mmol, 15% soln. in hexane) of n-BuLi are metered in rapidly. The mixture is heated under reflux for 25 min and subsequently cooled to −60° C. 1.5 ml (24.1 mmol) of methyl iodide are added, and the batch is stirred for 8.5 h with slow thawing to RT. Sat. ammonium chloride soln. and conc. ammonia soln. are added successively, and the mixture is stirred vigorously for a few minutes. The organic phase is separated off, and the aqueous phase is extracted with MTBE. The combined organic phases are washed with water, 2 N hydrochloric acid and sat. sodium chloride soln. The solution is dried using sodium sulfate and concentrated to dryness.

The crude product is purified by column chromatography (SiO$_2$, n-heptane n-heptane:EtOAc=95:5). The further purification is carried out by recrystallisation from IPA/n-heptane (10:1) and from acetone. 2-Methyl-5-(4'-propylbicyclohexyl-4-yl)selenophene is obtained as a colourless solid (m.p. 26° C.).

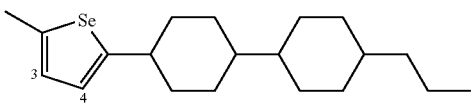

Δε=1.6
Δn=0.1014
γ$_1$=245 mPa·s
C 26 Sm 34 SmB 102 N 171.5 I $^1$H-NMR (400 MHz, CHCl$_3$): δ=6.71-6.69 (m, 2H, 3-H, 4-H), 2.72-2.64 (m, 1H, H$_{aliph.}$), 2.51 (s, 3H, Me$_{selenophene}$), 2.07 (dm, 2H, J=12.0 Hz, H$_{aliph.}$), 1.83-1.70 (m, 6H, H$_{aliph.}$), 1.41-1.26 (m, 4H, H$_{aliph.}$), 1.16-1.08 (m, 6H, H$_{aliph.}$), 1.05-0.93 (m, 2H, H$_{aliph.}$), 0.89-0.80 (m, 6H, H$_{aliph.}$).

MS (EI): m/e (%)=352 (98, [M+1]$^+$).

Example 19

2-Pentyl-5-(4'-propylbicyclohexyl-4-yl)selenophene

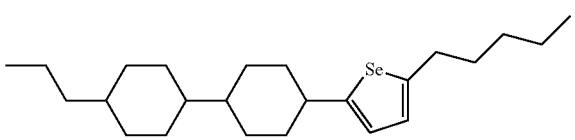

19.1 Preparation of 5-(4'-propylbicyclohexyl-3-en-4-yl)selenophene-2-carbaldehyde

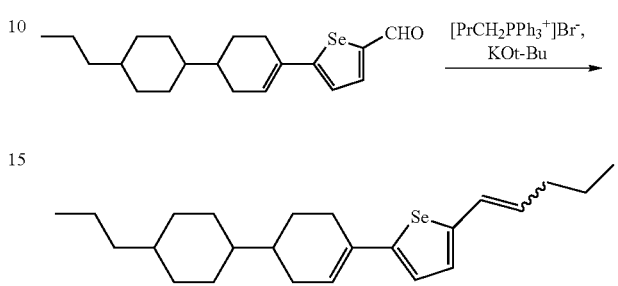

5.0 g (14.9 mmol) of 2-(4'-propylbicyclohexyl-3-en-4-yl) selenophene are initially introduced in 100 ml of diethyl ether/THF (4:1), and 12.5 ml (19.9 mmol, 15% soln. in hexane) of n-BuLi are metered in rapidly. The mixture is heated under reflux for 25 min and subsequently cooled to −78° C. 2.5 ml (25.0 mmol) of N-formylmorpholine are added in one portion, and the mixture is warmed to RT and stirred for 3 h. The batch is diluted with MTBE, and 1 N HCl is added. The organic phase is separated off, and the aqueous phase is extracted with MTBE. The combined organic phases are washed with sat. sodium chloride solution and dried using sodium sulfate. The solution is concentrated to dryness, and the residue is recrystallised from n-heptane. 5-(4'-Propylbicyclohexyl-3-en-4-yl)selenophene-2-carbaldehyde is obtained as a pale-orange solid.

19.2 Preparation of 2-(pent-1-enyl)-5-(4'-propylbicyclohexyl-3-en-4-yl)-selenophene

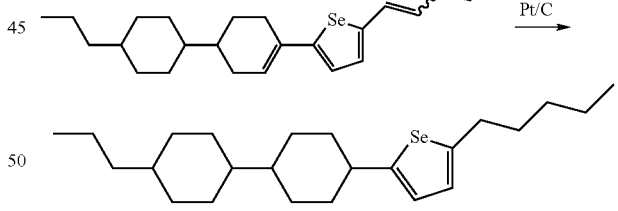

6.76 g (16.9 mmol) of butyltriphenylphosphonium bromide are initially introduced in 80 ml of THF at 0° C., and 1.76 g (12.5 mmol) of potassium tert-butoxide dissolved in 5 ml of THF are added. After 1 h, 4.35 g (12.0 mmol) of 5-(4'-propylbicyclohexyl-3-en-4-yl)selenophene-2-carbaldehyde are added in portions, and the batch is stirred at RT for 20 h. Water and 2 N hydrochloric acid are added to the mixture, and the batch is extracted with MTBE. The combined organic phases are washed with sat. sodium chloride soln. and dried using sodium sulfate. The solution is concentrated to dryness, and the residue is purified by column chromatography (SiO$_2$, n-heptane:EtOAc=25:1). 2-(Pent-1-enyl)-5-(4'-propylbicyclohexyl-3-en-4-yl)selenophene is obtained as a fluorescent-yellow solid.

19.3 Preparation of 2-pentyl-5-(4'-propylbicyclohexyl-4-yl)selenophene 3.1 g (7.6 mmol) of 2-(pent-1-enyl)-5-(4'-propylbicyclohexyl-3-en-4-yl)-selenophene are hydrogenated in 50 ml of ethyl acetate and in the presence of Pt/C (5% of Pt) at 90° C. and 8 bar of hydrogen. The solution is filtered and concentrated to dryness.

The residue is warmed at 80° C. for 6 h in 70 ml of NMP together with 300 mg (2.67 mmol) of potassium tert-butoxide. The mixture is diluted with MTBE and washed successively with water, 2 N hydrochloric acid and sat. sodium chloride soln. The organic phase is dried using sodium sulfate and concentrated to dryness. The crude product is purified by chromatography. 2-Pentyl-5-(4'-propylbicyclohexyl-4-yl)selenophene is obtained as a colourless wax-like solid.

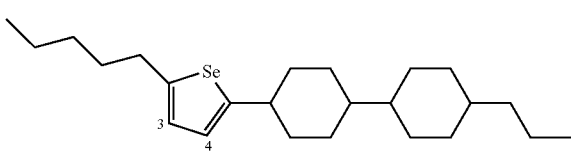

Δε=0.1
Δn=0.0815
γ₁=213 mPa·s
C 15 SmB 148

¹H-NMR (400 MHz, CHCl₃): δ=6.72-6.70 (m, 2H, 3-H, 4-H), 2.80 (t, 2H, J=7.8 Hz, H$_{aliph.}$), 2.72-2.64 (m, 1H, H$_{aliph.}$), 2.08 (dm, 2H, J=12.4 Hz, H$_{aliph.}$), 1.83-1.61 (m, 10H, H$_{aliph.}$), 1.43-1.26 (m, 8H, H$_{aliph.}$), 1.18-1.08 (m, 6H, H$_{aliph.}$), 1.05-0.94 (m, 1H, H$_{aliph.}$), 0.91-0.81 (m, 8H, H$_{aliph.}$).

MS (EI): m/e (%)=408 (97, [M+1]⁺).

Example 20

5-[4-(2-Methylacryloyloxy)phenyl]selenophen-2-ylmethyl 2-methylacrylate

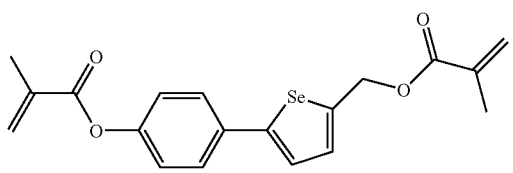

20.1 Preparation of 4-selenophen-2-ylphenol

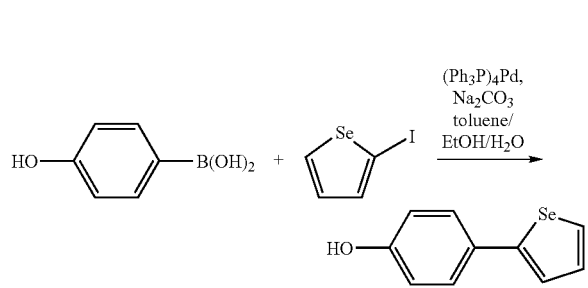

A mixture of 27.9 g (0.11 mol) of 2-iodoselenophene, 15.0 g (0.11 mol) of 2-hydroxyphenylboronic acid, 6.8 g (5.88 mmol) of tetrakis(triphenylphosphine)palladium(0) and 235 ml of 2 N sodium carbonate soln. in 600 ml of toluene/ethanol (1:1) is heated under reflux for 19 h. The mixture is diluted with MTBE and washed with water. The aqueous phase is extracted with MTBE, and the combined organic phases are washed with sat. sodium chloride soln. The solution is dried using sodium sulfate and concentrated to dryness. The residue is purified by column chromatography (SiO₂, n-heptane: MTBE=4:1→1:1). Further purification is carried out by digestion in cold n-heptane; 4-selenophen-2-ylphenol is obtained as a beige solid.

20.2 Preparation of triisopropyl-(4-selenophen-2-ylphenoxy)silane

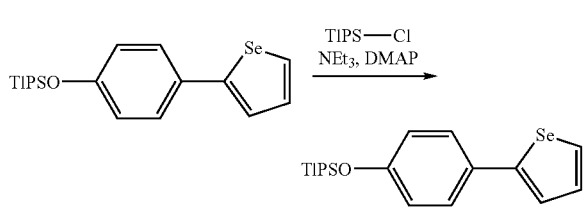

8.0 g (35.9 mmol) of 4-selenophen-2-ylphenol are initially introduced together with 50 ml (0.36 mol) of triethylamine and 0.44 g (3.6 mmol) of DMAP in 100 ml of dichloromethane, and 20 ml (93.5 mmol) of triisopropylchlorosilane are added. When the addition is complete, the mixture is warmed under reflux for 3 h. After cooling, the reaction mixture is added to water, and the organic phase is separated off. The aqueous phase is extracted with dichloromethane, and the combined organic phase is washed with sat. sodium chloride soln. The solution is dried using sodium sulfate and concentrated to dryness. The residue is purified by column chromatography (SiO₂, n-heptane:MTBE=4:1). Further purification is carried out by further column chromatography (SiO₂, n-heptane:toluene=4:1); triisopropyl-(4-selenophen-2-ylphenoxy)silane is obtained as a yellow oil.

20.3 Preparation of 5-(4-triisopropylsilanyloxyphenyl)selenophene-2-carbaldehyde

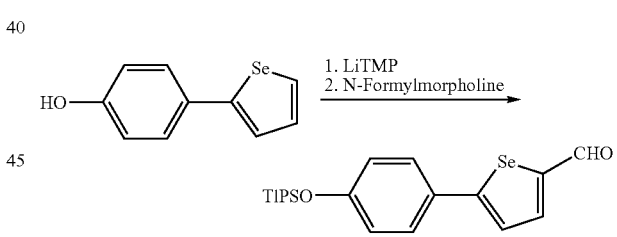

11.0 g (27.9 mmol) of triisopropyl-(4-selenophen-2-ylphenoxy)silane are initially introduced in 200 ml of diethyl ether, and 20 ml (31.8 mmol, 15% soln. in hexane) of n-BuLi are metered in rapidly. The mixture is heated under reflux for 30 min and subsequently cooled to −70° C. 15.0 ml (0.15 mol) of N-formylmorpholine in 50 ml of diethyl ether are added, and the mixture is warmed to RT and stirred for 1 h. The mixture is added to water, and 2 N hydrochloric acid is added. The organic phase is separated off, and the aqueous phase is extracted with MTBE. The combined organic phases are washed with sat. sodium chloride soln. and dried using sodium sulfate. The solution is concentrated to dryness, and the residue is purified by column chromatography (SiO₂, toluene). 5-(4-Triisopropylsilanyloxyphenyl)selenophene-2-carbaldehyde is obtained as a red solid.

20.4 Preparation of [5-(4-triisopropylsilanyloxyphenyl)selenophen-2-yl]-methanol

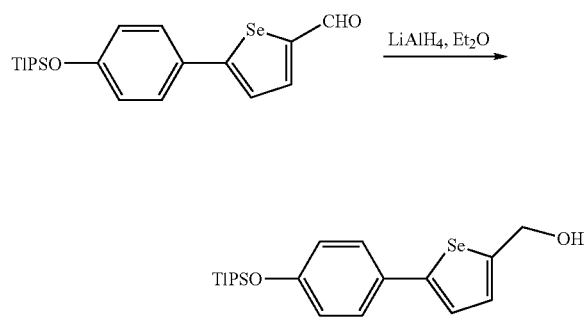

9.50 g (23.3 mmol) of 5-(4-triisopropylsilanyloxyphenyl)selenophene-2-carbaldehyde dissolved in 140 ml of diethyl ether are slowly added to a suspension of 0.88 g (23.3 mmol) of lithium aluminium hydride in 70 ml of diethyl ether with ice-cooling. When the addition is complete, the mixture is stirred for 15 min, and ethanol is added dropwise to the mixture until evolution of hydrogen no longer occurs. A sat. potassium sodium tartrate soln. is added, and the mixture is stirred vigorously. The organic phase is separated off, and the aqueous phase is extracted with diethyl ether. The combined organic phases are washed with sat. sodium chloride soln. and dried using sodium sulfate. The solution is concentrated to dryness, and the residue is purified by column chromatography ($SiO_2$, n-heptane:MTBE=1:1). [5-(4-Triisopropylsilanyloxyphenylselenophen-2-yl]methanol is obtained as a yellow oil.

20.5 Preparation of 4-(5-hydroxymethylselenophen-2-yl)phenol

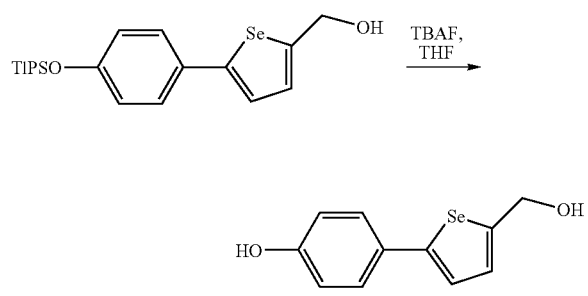

8.7 g (21.4 mmol) of [5-(4-triisopropylsilanyloxyphenyl)selenophen-2-yl]-methanol are initially introduced in 200 ml of THF, and 50 ml of TBAF (50 mmol, 1 M soln. in THF) are added with ice-cooling. After 30 min at this temperature, the mixture is added to water and extracted with MTBE. The organic phase is separated off, and the aqueous phase is extracted with MTBE. The combined organic phases are washed with sat. sodium chloride soln. and dried using sodium sulfate. The solution is concentrated to dryness, and the residue is recrystallised from ethyl acetate. 4-(5-Hydroxymethylselenophen-2-yl)phenol is obtained as a beige solid.

20.6 Preparation of 5-[4-(2-methylacryloyloxy)phenyl]selenophen-2-yl-methyl 2-methylacrylate

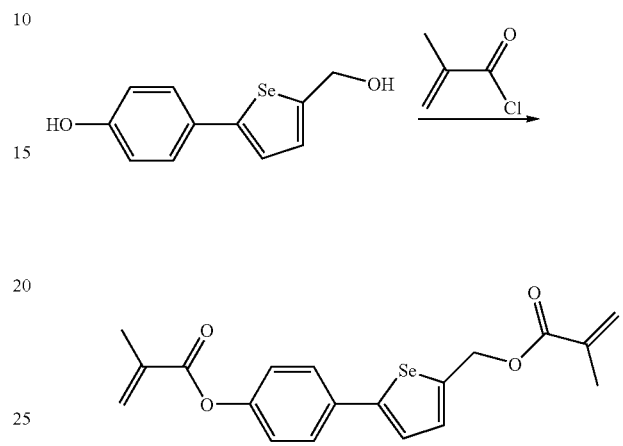

4.70 g (18.4 mmol) of 4-(5-hydroxymethylselenophen-2-yl)phenol are initially introduced together with 8.0 ml (57.7 mmol) of triethylamine and 45.0 mg (0.37 mmol) of DMAP in 35 ml of dichloromethane. At 0° C., a solution of 3.69 ml (38.3 mmol) of methacryloyl chloride in 15 ml of dichloromethane is added, and the mixture is stirred for 30 min. The batch is filtered through Celite. The solution is washed with water, 0.5 N hydrochloric acid and sat. sodium chloride soln. and dried using sodium sulfate. The solution is concentrated with exclusion of light. The crude product is purified by column chromatography ($SiO_2$, toluene:ethyl acetate=4:1). The further purification is carried out by repeated recrystallisation from methanol and from THF/n-hexane; 5-[4-(2-methylacryloyloxy)phenyl]-selenophen-2-ylmethyl 2-methylacrylate is obtained as a colourless solid having an m.p. of 91° C.

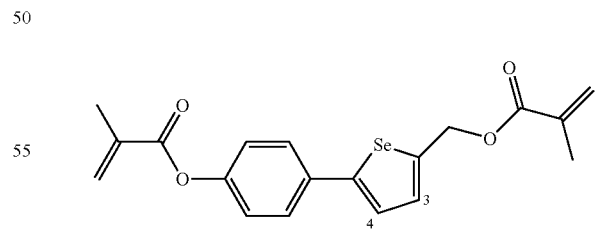

$^1$H-NMR (300 MHz, $CHCl_3$): δ=7.53 (d, 2H, J=8.7 Hz, $H_{arom.}$), 7.27 (d, 1H, J=4.0 Hz, 4-H), 7.22 (dm, 1H, J=4.0 Hz, 3-H), 7.12 (d, 2H, J=8.7 Hz, $H_{arom.}$), 6.35 (s (broad), 1H, $H_{vinyl}$), 6.18 (s (broad), 1H, $H_{vinyl}$), 5.76 (t, 1H, J=1.5 Hz, $H_{vinyl}$), 5.60 (t, 1H, J=1.5 Hz, $H_{vinyl}$), 5.36 (s, 2H, $CH_2O$), 2.07-2.06 (m, 3H, Me), 1.98-1.97 (m, 3H, Me).

MS (EI): m/e (%)=390 (35, [M+1]$^+$), 69 (100).

Example 21

2-{4-[Difluoro-(3,4,5-trifluorophenoxy)methyl]-3,5-difluoro-phenyl}-5-propylselenophene

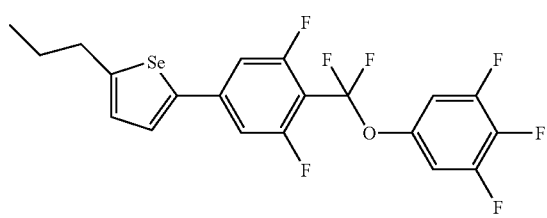

21.1 Preparation of 2-{-4-[difluoro-(3,4,5-trifluorophenoxy)methyl]-3,5-difluorophenyl}-5-propylselenophene

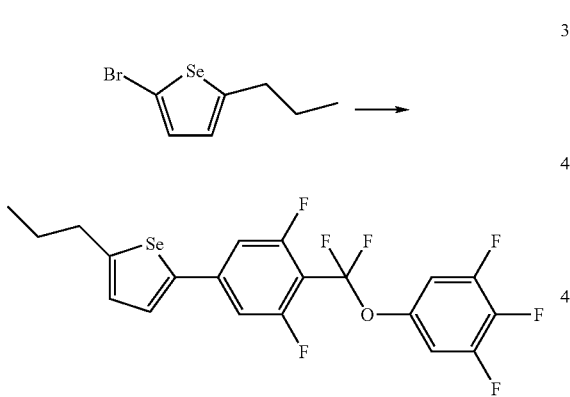

A mixture of 2.8 g (10.3 mmol) of 2-bromo-5-propylselenophene, 216 mg (0.31 mmol) of bis(triphenylphosphine)palladium(II) chloride, 40 µl (0.66 mmol) of hydrazine hydrate (80%) and 7 ml (7.0 mmol) of aqueous sodium metaborate soln. (1 M) is heated to 60° C. A soln. of 5.0 g (11.5 mmol) of 3-fluoro-4'-propylbiphenyl-4-ylboronic acid in 10 ml of THF is metered in slowly, and the batch is stirred at this temperature for 24 h. After cooling, the mixture is diluted with n-heptane, and the organic phase is separated off. The aqueous phase is extracted with n-heptane, and the combined organic phases are dried using sodium sulfate. The solution is concentrated to dryness, and the residue is purified by column chromatography (SiO$_2$, n-heptane:EtOAc=98:2). The further purification is carried out by recrystallisation from ethanol and n-heptane. 2-{4-[Difluoro-(3,4,5-trifluorophenoxy)methyl]-3,5-difluorophenyl}-5-propylselenophene is obtained as a colourless solid having an m.p. of 30° C.

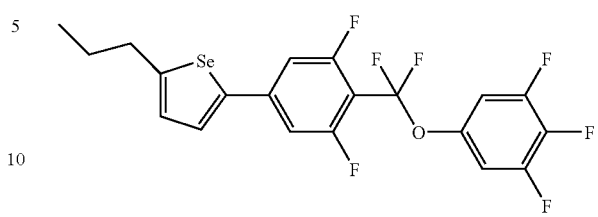

Δε=23.6
Δn=0.1334
γ$_1$=59 mPa·s
C 30 I $^1$H-NMR (400 MHz, CHCl$_3$): δ=7.36 (d, 1H, J=3.8 Hz, H$_{arom.}$), 7.09 (s, 1H, H$_{arom.}$), 7.06 (s, 1H, H$_{arom.}$), 7.02-6.96 (m, 3H, H$_{arom.}$), 2.87 (t, 2H, J=7.6 Hz, H$_{aliph.}$), 1.80-1.73 (m, 2H, H$_{aliph.}$), 1.01 (t, 3H, J=7.6 Hz, H$_{aliph.}$).

$^{19}$F-NMR (376 MHz, CHCl$_3$): δ=−61.5 (t, 2F, J=$_{26.2}$ Hz), −110.7 (dt, 2F, J=26.2 Hz, J=10.2 Hz), −132.5--132.6 (m, 2F), −163.2--163.4 (m, 1F).

MS (EI): m/e (%)=482 (7, [M+1]$^+$), 335 (100).

Example 22

2-(4'-Ethyl-3-fluorobiphenyl-4-yl)-5-methylselenophene

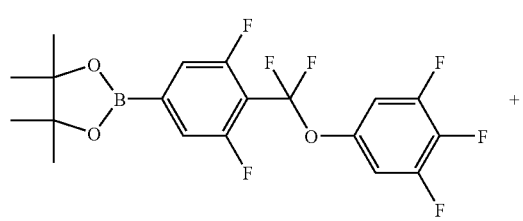

22.1 Preparation of 2-(4'-ethyl-3-fluorobiphenyl-4-yl)selenophene

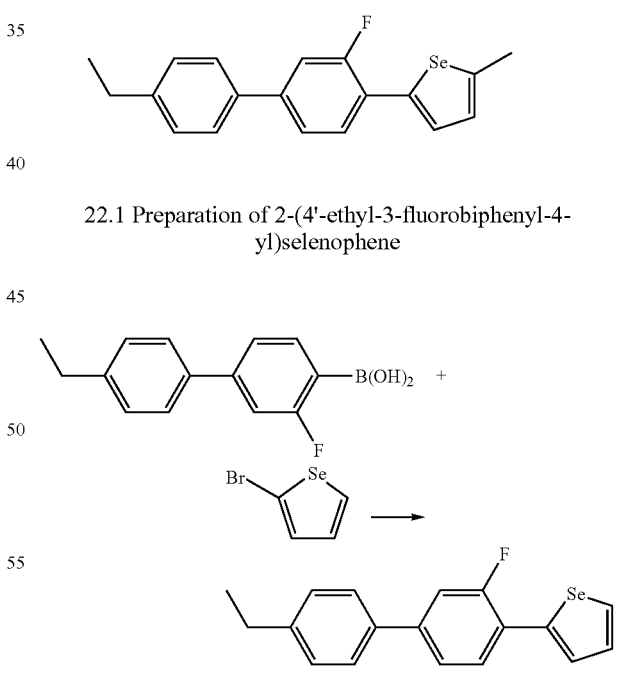

A mixture of 34.2 g (0.16 mol) of 2-bromoselenophene, 40.0 g (0.16 mol) of 3-fluoro-4'-ethylbiphenyl-4-ylboronic acid, 10.0 g (8.65 mmol) of tetrakis-(triphenylphosphine)palladium(0) and 200 ml of 2 N sodium carbonate soln. in 500 ml of toluene/ethanol (2:3) is heated at 90° C. for 2 h. After cooling, the organic phase is separated off, and the aqueous phase is extracted with toluene. The combined organic phases are washed with water, and the solution is dried using sodium sulfate. The solution is concentrated to dryness, and the residue is purified by column chromatography (SiO$_2$, n-heptane:toluene=9:1). 2-(4'-Ethyl-3-fluorobiphenyl-4-yl)-selenophene is obtained as a yellow solid.

22.2 Preparation of 2-(4'-ethyl-3-fluorobiphenyl-4-yl)-5-methylselenophene

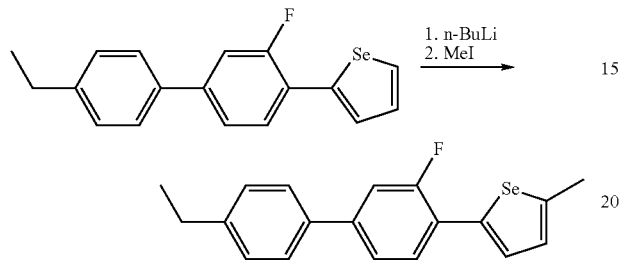

5.5 ml (32.3 mmol) of TMP are initially introduced at −15° C. in 20 ml of diethyl ether, and 20.0 ml (31.8 mmol, 15% soln. in hexane) of n-BuLi are metered in. After 30 min, a solution of 10.0 g (30.4 mmol) of 2-(4'-ethyl-3-fluorobiphenyl-4-yl)selenophene in 80 ml of diethyl ether is added. When the addition is complete, the batch is warmed to RT and stirred for 90 min. The solution is cooled to −70° C., and 10.0 ml (0.16 mol) of methyl iodide are added. The reaction mixture is warmed to RT and stirred for 20 h. Sat. ammonium chloride soln. and conc. ammonia soln. are added successively, and the mixture is stirred vigorously for a few minutes. The organic phase is separated off, and the aqueous phase is extracted with MTBE. The combined organic phases are washed successively with water, 2 N hydrochloric acid and sat. sodium chloride soln. The solution is dried using sodium sulfate and concentrated to dryness. The crude product is purified by column chromatography (SiO$_2$, n-heptane:toluene=95:5). The further purification is carried out by recrystallisation from n-heptane. 2-(4'-Ethyl-3-fluorobiphenyl-4-yl)-5-methylselenophene is obtained as a solid having an m.p. of 121° C.

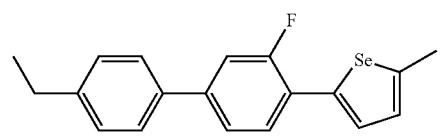

Δ∈=5.3

Δn=0.3063

γ$_1$=154 mPa·s

C 121 N 143 I $^1$H-NMR (400 MHz, CHCl$_3$): δ=7.61-7.56 (m, 1H, H$_{seleno.}$), 7.52 (d, 2H, J=8.0 Hz, H$_{arom.}$), 7.46 (d, 1H, J=3.6 Hz, H$_{seleno.}$), 7.37 (dd, 1H, J=3.6 Hz, J=2.0 Hz, H$_{seleno.}$), 7.34 (dd, 1H, J=8.4 Hz, J=1.6 Hz, H$_{arom.}$), 7.25 (d, 2H, J=8.4 Hz, H$_{arom.}$), 6.97-6.95 (m, 1H, H$_{arom.}$), 2.70 (q, 2H, J=7.6 Hz, CH$_2$CH$_3$), 2.61 (s, 3H, CH$_3$), 1.28 (t, 3H, J=7.6 Hz, CH$_2$CH$_3$).

$^{19}$F-NMR (376 MHz, CHCl$_3$): δ=−114.6 (dd, 1F, J=12.4 Hz, J=8.6 Hz).

MS (EI): m/e (%)=344 (100, [M+1]$^+$), 329 (34, [M−Me]$^+$).

Example 23

2-Ethyl-5-(4'-ethyl-3-fluorobiphenyl-4-yl)selenophene

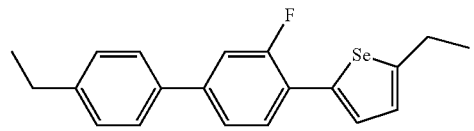

23.1 Preparation of 5-(4'-ethyl-3-fluorobiphenyl-4-yl)selenophene-2-carbaldehyde

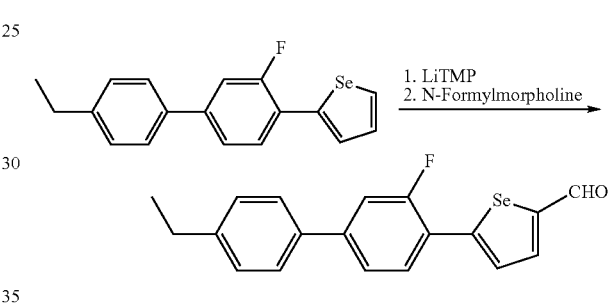

27.5 ml (0.16 mol) of TMP are initially introduced at −20° C. in 100 ml of THF, and 100 ml (0.16 mol, 15% soln. in hexane) of n-BuLi are metered in. After 30 min at this temperature, a solution of 50.2 g (0.15 mol) of 2-(4'-ethyl-3-fluorobiphenyl-4-yl)selenophene in 400 ml of THF is added. When the addition is complete, the batch is warmed to RT and left at this temperature for 30 min. The solution is cooled to −70° C., and 17.0 ml (0.17 mol) of N-formylmorpholine are added. The reaction mixture is warmed to RT and stirred for 1 h. the solution is diluted with a lot of dichloromethane, and 2 N hydrochloric acid is added. The mixture is washed with water, and the organic phase is separated off. The aqueous phase is extracted with dichloromethane, and the combined organic phases are washed with sat. sodium chloride soln. The solution is dried using sodium sulfate and concentrated to dryness. The residue is taken up in dichloromethane and purified by column chromatography (SiO$_2$, toluene). The further purification is carried out by recrystallisation from toluene. 5-(4'-Ethyl-3-fluorobiphenyl-4-yl)selenophene-2-carbaldehyde is obtained as a brown solid.

23.2 Preparation of 2-(4'-ethyl-3-fluorobiphenyl-4-yl)-5-vinylselenophene

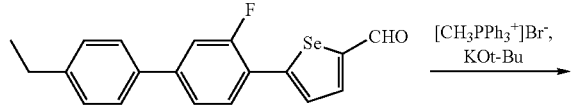

-continued

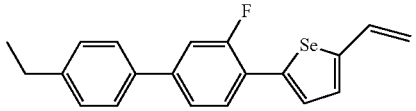

5.0 g (13.9 mmol) of methyltriphenylphosphonium bromide are initially introduced together with 4.20 g (11.8 mmol) of 5-(4'-ethyl-3-fluorobiphenyl-4-yl)selenophene-2-carbaldehyde in 180 ml of THF, and a solution of 1.50 g (13.4 mmol) of potassium tert-butoxide in 20 ml of THF is added with ice-cooling. The mixture is stirred at RT for 3 h. Water and 2 N hydrochloric acid are added, and the batch is extracted with MTBE. The organic phase is washed with sat. sodium chloride soln. and dried using sodium sulfate. The solution is concentrated to dryness, and the residue is purified by column chromatography ($SiO_2$, toluene). 2-(4'-Ethyl-3-fluorobiphenyl-4-yl)-5-vinylselenophene is obtained as a beige solid.

23.3 Preparation of 2-ethyl-5-(4'-ethyl-3-fluorobiphenyl-4-yl)selenophene

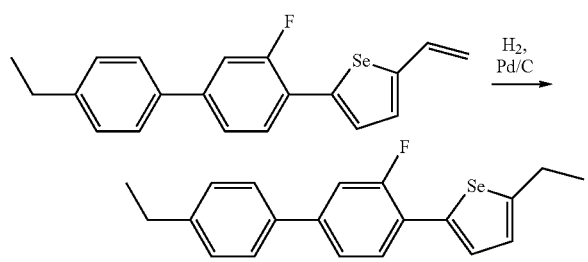

3.10 g (8.73 mmol) of 2-(4'-ethyl-3-fluorobiphenyl-4-yl)-5-vinylselenophene are hydrogenated in 30 ml of ethyl acetate, in the presence of Pd/C (5% of Pd) at atmospheric pressure and RT. The reaction soln. is filtered and concentrated to dryness, and the crude product is purified by column chromatography ($SiO_2$, n-heptane:toluene=9:1). The further purification is carried out by recrystallisation from ethanol and n-heptane. 2-Ethyl-5-(4'-ethyl-3-fluorobiphenyl-4-yl)selenophene is obtained as a colourless solid (m.p. 110° C.).

Δ∈=5.2
Δn=0.2880
$γ_1$=124 mPa·s
C 110 N 130 I $^1$H-NMR (300 MHz, $CHCl_3$): δ=7.61-7.55 (m, 1H, $H_{seleno.}$), 7.51 (d, 2H, J=8.1 Hz, $H_{arom.}$), 7.47 (d, 1H, J=3.6 Hz, $H_{seleno.}$), 7.36 (s, 1H, $H_{arom.}$), 7.32 (dd, 1H, J=5.3 Hz, J=1.6 Hz, $H_{arom.}$), 7.27 (d, 2H, J=8.1 Hz, $H_{arom.}$), 6.98-6.95 (m, 1H, $H_{arom.}$), 2.94 (q, 2H, J=7.3 Hz, $CH_2CH_3$), 2.69 (q, 2H, J=7.6 Hz, $CH_2CH_3$), 1.35 (t, 3H, J=7.3 Hz, $CH_2CH_3$), 1.27 (t, 3H, J=7.6 Hz, $CH_2CH_3$).

$^{19}$F-NMR (282 MHz, $CHCl_3$): δ=−114.6 (dd, 1F, J=12.9 Hz, J=8.2 Hz).

MS (EI): m/e (%)=358 (58, [M+1]$^+$), 343 (100, [M+1−Me]$^+$).

Example 24

2-(4'-Ethyl-3-fluorobiphenyl-4-yl)-5-propylselenophene

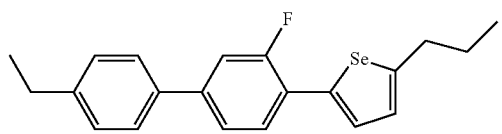

2-(4'-Ethyl-3-fluorobiphenyl-4-yl)-5-propylselenophene is prepared analogously to Example 23 by Wittig reaction and subsequent hydrogenation from 5-(4'-ethyl-3-fluorobiphenyl-4-yl)selenophene-2-carbaldehyde. 2-(4'-Ethyl-3-fluorobiphenyl-4-yl)-5-propylselenophene is obtained as a colourless solid having an m.p. of 88° C.

Δ∈=4.4
Δn=0.2845
$γ_1$=106 mPa·s
C 88 N 130 I $^1$H-NMR (300 MHz, $CHCl_3$): δ=7.62-7.56 (m, 1H, $H_{seleno.}$), 7.51 (d, 2H, J=8.3 Hz, $H_{arom.}$), 7.48 (d, 1H, J=3.6 Hz, $H_{seleno.}$), 7.36 (s, 1H, $H_{arom.}$), 7.32 (dd, 1H, J=5.3 Hz, J=1.6 Hz, $H_{arom.}$), 7.27 (d, 2H, J=8.3 Hz, $H_{arom.}$), 6.98-6.95 (m, 1H, $H_{arom.}$), 2.88 (t, 2H, J=7.3 Hz, $CH_2CH_2CH_3$), 2.69 (q, 2H, J=7.6 Hz, $CH_2CH_3$), 1.81-1.68 (m, 2H, $CH_2CH_2CH_3$), 1.27 (t, 3H, J=7.6 Hz, $CH_2CH_3$), 1.02 (t, 3H, J=7.3 Hz, $CH_2CH_2CH_3$).

$^{19}$F-NMR (282 MHz, $CHCl_3$): δ=−114.5 (dd, 1F, J=12.8 Hz, J=8.1 Hz).

MS (EI): m/e (%)=372 (51, [M+1]$^+$), 343 (100, [M+1−Et]$^+$).

Example 25

2-Butyl-5-(4'-ethyl-3-fluorobiphenyl-4-yl)selenophene

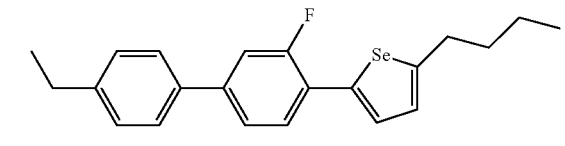

2-Butyl-5-(4'-ethyl-3-fluorobiphenyl-4-yl)selenophene is prepared analogously to Example 23 by Wittig reaction and subsequent hydrogenation from 5-(4'-ethyl-3-fluorobiphenyl-4-yl)selenophene-2-carbaldehyde. 2-Butyl-5-(4'-ethyl-3-fluorobiphenyl-4-yl)selenophene is obtained as a colourless solid having an m.p. of 47° C.

Δ∈=4.4
Δn=0.2738
$γ_1$=97 mPa·s
C 47 Sm (74) SmA 77 N 120 I $^1$H-NMR (300 MHz, $CHCl_3$): δ=7.63-7.57 (m, 1H, $H_{seleno.}$), 7.51 (d, 2H, J=8.2 Hz, $H_{arom.}$), 7.49 (d, 1H, J=3.6 Hz, $H_{seleno.}$), 7.36 (s, 1H, $H_{arom.}$), 7.32 (dd, 1H, J=5.3 Hz, J=1.6 Hz, $H_{arom.}$), 7.27 (d, 2H, J=8.2 Hz, $H_{arom.}$), 6.98-6.95

(m, 1H, H$_{arom.}$), 2.91 (t, 2H, J=7.3 Hz, CH$_2$(CH$_2$)$_2$CH$_3$), 2.69 (q, 2H, J=7.6 Hz, CH$_2$CH$_3$), 1.76-1.65 (m, 2H, CH$_2$(CH$_2$)$_2$CH$_3$), 1.50-1.38 (m, 2H, CH$_2$(CH$_2$)$_2$CH$_3$), 1.27 (t, 3H, J=7.6 Hz, CH$_2$CH$_3$), 0.96 (t, 3H, J=7.3 Hz, 1.76-1.65 (m, 2H, CH$_2$(CH$_2$)$_2$CH$_3$).

$^{19}$F-NMR (282 MHz, CHCl$_3$): δ=-114.6 (dd, 1F, J=12.9 Hz, J=82 Hz).

MS (EI): m/e (%)=386 (82, [M+1]$^+$), 343 (100, [M+1-Pr]$^+$).

Example 26

2-(4'-Ethyl-3-fluorobiphenyl-4-yl)-5-pentylselenophene

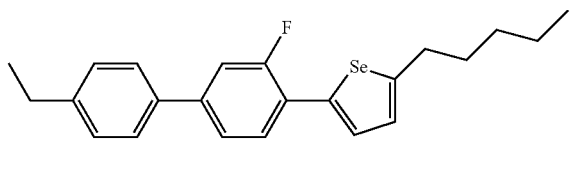

26.1 Preparation of 2-(4'-ethyl-3-fluorobiphenyl-4-yl)-5-(pent-1-enyl)-selenophene

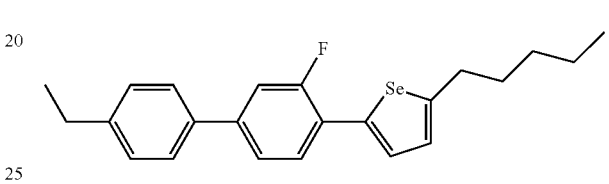

22.0 g (54.5 mmol) of butyltriphenylphosphonium bromide are initially introduced together with 17.3 g (48.4 mmol) of 5-(4'-ethyl-3-fluorobiphenyl-4-yl)selenophene-2-carbaldehyde in 700 ml of THF, and a solution of 6.0 g (53.5 mmol) of potassium tert-butoxide in 100 ml of THF is added with ice-cooling. The mixture is stirred at RT for 3 h. Water and 2 N hydrochloric acid are added, and the batch is extracted with MTBE. The organic phase is washed with sat. sodium chloride soln. and dried using sodium sulfate. The solution is concentrated to dryness, and the residue is purified by column chromatography (SiO$_2$, toluene). 2-(4'-Ethyl-3-fluorobiphenyl-4-yl)-5-(pent-1-enyl)selenophene is obtained as an orange solid.

26.2 Preparation of 2-(4'-ethyl-3-fluorobiphenyl-4-yl)-5-pentylselenophene

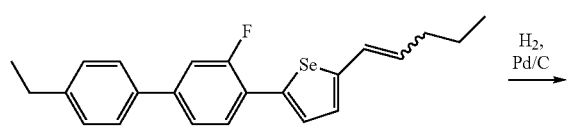

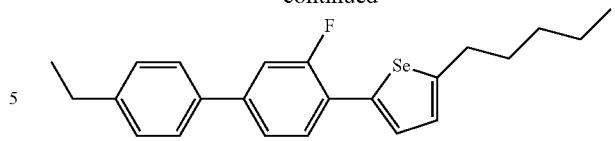

17.1 g (43.0 mmol) of 2-(4'-ethyl-3-fluorobiphenyl-4-yl)-5-(pent-1-enyl)-selenophene are hydrogenated in 170 ml of ethyl acetate, in the presence of Pd/C (5% of Pd) at atmospheric pressure and RT. The reaction soln. is filtered and concentrated to dryness, and the crude product is purified by column chromatography (SiO$_2$, n-heptane:toluene=98:2→95:5). The further purification is carried out by recrystallisation from ethanol and n-heptane. 2-(4'-Ethyl-3-fluorobiphenyl-4-yl)-5-pentylselenophene is obtained as a colourless solid (m.p. 52° C.).

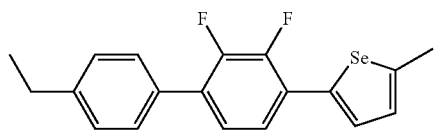

Δ∈=4.8
Δn=0.2709
γ$_1$=113 mPa·s
C 52 SmB 63 SmC 67 N 125 I $^1$H-NMR (300 MHz, CHCl$_3$): δ=7.62-7.56 (m, 1H, H$_{seleno.}$), 7.51 (d, 2H, J=8.1 Hz, H$_{arom.}$), 7.47 (d, 1H, J=3.9 Hz, H$_{seleno.}$), 7.36 (s, 1H, H$_{arom.}$), 7.33 (dd, 1H, J=5.7 Hz, J=1.8 Hz, H$_{arom.}$), 7.27 (d, 2H, J=8.1 Hz, H$_{arom.}$), 6.97-6.94 (m, 1H, H$_{arom.}$), 2.90 (t, 2H, J=7.4 Hz, CH$_2$(CH$_2$)$_3$CH$_3$), 2.69 (q, 2H, J=7.6 Hz, CH$_2$CH$_3$), 1.77-1.67 (m, 2H, CH$_2$(CH$_2$)$_3$CH$_3$), 1.44-1.32 (m, 4H, CH$_2$(CH$_2$)$_3$CH$_3$), 1.27 (t, 3H, J=7.6 Hz, CH$_2$CH$_3$), 0.92 (t, 3H, J=7.1 Hz, CH$_2$CH$_3$).

$^{19}$F-NMR (282 MHz, CHCl$_3$): δ=-114.5 (dd, 1F, J=12.3 Hz, J=8.3 Hz).

MS (EI): m/e (%)=400 (72, [M+1]$^+$), 343 (100, [M+1-Bu]$^+$).

Example 27

2-(4'-Ethyl-2,3-difluorobiphenyl-4-yl)-5-methylselenophene

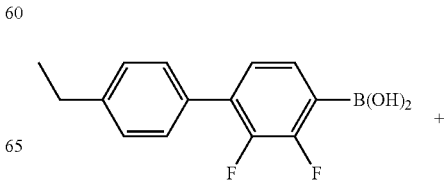

27.1 Preparation of 2-(4'-ethyl-2,3-difluorobiphenyl-4-yl)selenophene

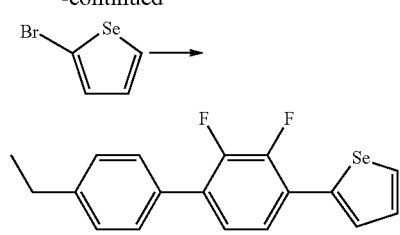

A mixture of 56.0 g (0.27 mol) of 2-bromoselenophene, 70.0 g (0.27 mol) of 2,3-difluoro-4'-ethylbiphenyl-4-ylboronic acid, 22.0 g (19.0 mmol) of tetrakis(triphenylphosphine)palladium(0) and 800 ml of 2 N sodium carbonate soln. in 2.5 l of toluene/ethanol (1:1) is heated at 90° C. for 17 h. After cooling, the organic phase is separated off, and the aqueous phase is extracted with toluene. The combined organic phases are washed with water, and the solution is dried using sodium sulfate. The solution is concentrated to dryness, and the residue is purified by column chromatography (SiO$_2$, toluene). The further purification is carried out by recrystallisation from ethanol and n-heptane. 2-(4'-Ethyl-2,3-difluorobiphenyl-4-yl)-selenophene is obtained as a yellowish solid.

27.2 Preparation of 2-(4'-ethyl-2,3-difluorobiphenyl-4-yl)-5-methylselenophene

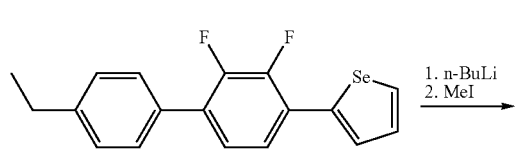

3.7 ml (21.7 mmol) of TMP are initially introduced at −15° C. in 10 ml of diethyl ether, and 13.0 ml (20.7 mmol, 15% soln. in hexane) of n-BuLi are metered in. After 30 min, a solution of 6.8 g (19.6 mmol) of 2-(4'-ethyl-2,3-difluorobiphenyl-4-yl)selenophene in 50 ml of diethyl ether is added. When the addition is complete, the batch is warmed to RT and stirred for 90 min. The solution is cooled to −70° C., and 6.0 ml (96.4 mmol) of methyl iodide are added. The reaction mixture is warmed to RT and stirred for 20 h. Sat. ammonium chloride soln. and conc. ammonia soln. are added successively, and the mixture is stirred vigorously for a few minutes. The organic phase is separated off, and the aqueous phase is extracted with MTBE. The combined organic phases are washed successively with water, 2 N hydrochloric acid and sat. sodium chloride soln. The solution is dried using sodium sulfate and concentrated to dryness. The crude product is purified by column chromatography (SiO$_2$, n-heptane:toluene=9:1). The further purification is carried out by recrystallisation from ethanol and n-heptane. 2-(4'-Ethyl-2,3-difluorobiphenyl-4-yl)-5-methylselenophene is obtained as a solid having an m.p. of 92° C.

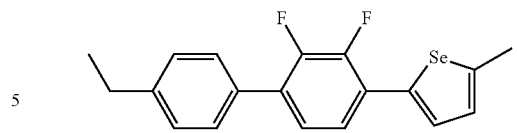

$\Delta\varepsilon = -2.6$
$\Delta n = 0.2808$
$\gamma_1 = 148$ mPa·s
C 92 N 109 I $^1$H-NMR (300 MHz, CHCl$_3$): δ=7.51-7.46 (m, 3H, H$_{arom.}$), 7.35-7.27 (m, 3H, H$_{arom.}$), 7.20-7.14 (m, 1H, H$_{arom.}$), 6.97-6.94 (m, 1H, H$_{arom.}$), 2.71 (q, 2H, J=7.6 Hz, CH$_2$CH$_3$), 2.61 (d, 3H, J=1.0 Hz, CH$_3$), 1.28 (t, 3H, J=7.6 Hz, CH$_2$CH$_3$).

$^{19}$F-NMR (282 MHz, CHCl$_3$): δ=−140.1 (dd, 1F, J=19.2 Hz, J=7.3 Hz), −143.2 (ddd, 1F, J=19.2 Hz, J=7.3 Hz, J=1.7 Hz).

MS (EI): m/e (%)=362 (100, [M+1]$^+$), 347 (40, [M−Me]$^+$).

Example 28

2-(4'-Ethyl-2,3-difluorobiphenyl-4-yl)-5-propylselenophene

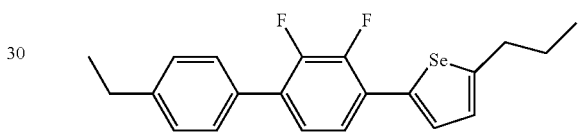

28.1 Preparation of 5-(4'-ethyl-2,3-difluorobiphenyl-4-yl)selenophene-2-carbaldehyde

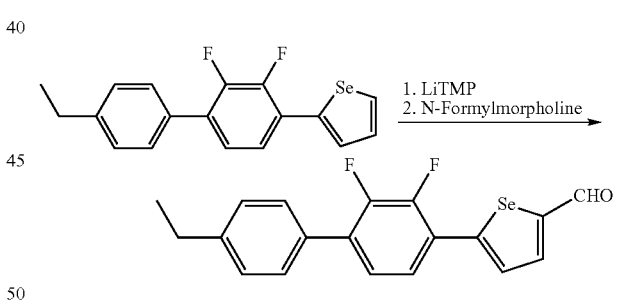

6.0 ml (35.3 mmol) of TMP are initially introduced at −20° C. in 30 ml of THF, and 21.5 ml (34.2 mmol, 15% soln. in hexane) of n-BuLi are metered in. After 30 min at this temperature, a solution of 11.8 g (34.0 mmol) of 2-(4'-ethyl-2,3-difluorobiphenyl-4-yl)selenophene in 70 ml of THF is added. When the addition is complete, the batch is warmed to RT and left at this temperature for 90 min. The solution is cooled to −60° C., and 3.6 ml (36.0 mmol) of N-formylmorpholine are added. The reaction mixture is warmed to RT and stirred for 2 h. The solution is diluted with a lot of dichloromethane, and 2 N hydrochloric acid is added. The mixture is washed with water, and the organic phase is separated off. The aqueous phase is extracted with dichloromethane, and the combined organic phases are washed with sat. sodium chloride soln. The solution is dried using sodium sulfate and concentrated to dryness. The residue is recrystallised from toluene. 5-(4'-

Ethyl-2,3-difluorobiphenyl-4-yl)selenophene-2-carbaldehyde is obtained as a brown solid.

28.2 Preparation of 2-(4'-ethyl-3-fluorobiphenyl-4-yl)-5-propenylselenophene

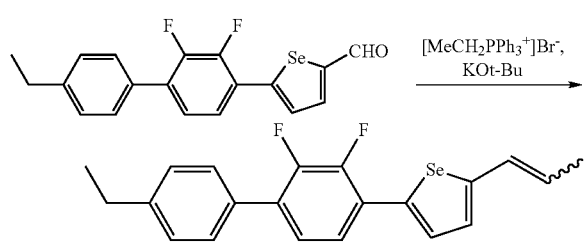

4.70 g (12.7 mmol) of ethyltriphenylphosphonium bromide are initially introduced together with 3.70 g (9.86 mmol) of 5-(4'-ethyl-2,3-difluorobiphenyl-4-yl)selenophene-2-carbaldehyde in 180 ml of THF, and a solution of 1.40 g (12.5 mmol) of potassium tert-butoxide in 20 ml of THF is added with ice-cooling. The mixture is stirred at RT for 1 h. Water and 2 N hydrochloric acid are added, and the batch is extracted with MTBE. The organic phase is washed with sat. sodium chloride soln. and dried using sodium sulfate. The solution is concentrated to dryness, and the residue is purified by column chromatography (SiO$_2$, n-heptane:toluene=95:5). 2-(4'-Ethyl-3-fluorobiphenyl-4-yl)-5-propenylselenophene is obtained as a yellow solid.

28.3 Preparation of 2-(4'-ethyl-2,3-difluorobiphenyl-4-yl)-5-propylselenophene

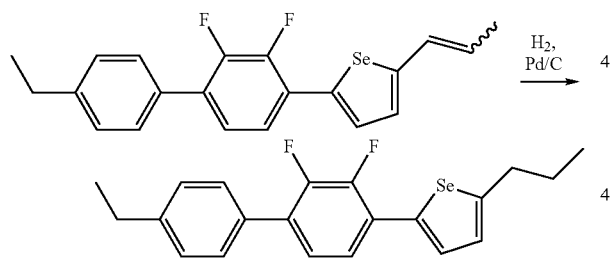

2.0 g (4.79 mmol) of 2-(4'-ethyl-3-fluorobiphenyl-4-yl)-5-propenylselenophene are hydrogenated in 20 ml of ethyl acetate, in the presence of Pd/C (5% of Pd) at atmospheric pressure and RT. The reaction soln. is filtered and concentrated to dryness, and the crude product is purified by column chromatography (SiO$_2$, n-heptane:toluene=9:1). The further purification is carried out by recrystallisation from ethanol and n-heptane. 2-(4'-Ethyl-2,3-difluorobiphenyl-4-yl)-5-propylselenophene is obtained as a colourless solid (m.p. 74° C.).

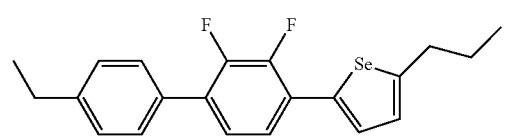

$\Delta\epsilon = -2.3$ $\Delta n = 0.2459$ $\gamma_1 = 78$ mPa·s

C 74 N 102 I $^1$H-NMR (300 MHz, CHCl$_3$): δ=7.51-7.48 (m, 3H, H$_{arom.}$), 7.36-7.28 (m, 3H, H$_{arom.}$), 7.20-7.14 (m, 1H, H$_{arom.}$), 6.99-6.97 (m, 1H, H$_{arom.}$), 2.89 (t, 2H, J=7.4 Hz, CH$_2$CH$_2$CH$_3$), 2.70 (q, 2H, J=7.6 Hz, CH$_2$CH$_3$), 1.79-1.70 (m, 2H, CH$_2$CH$_2$CH$_3$), 1.28 (t, 3H, J=7.6 Hz, CH$_2$CH$_3$), 1.02 (t, 3H, J=7.4 Hz, CH$_2$CH$_2$CH$_3$).

$^{19}$F-NMR (376 MHz, CHCl$_3$): δ=−140.2 (dd, 1F, J=19.2 Hz, J=7.2 Hz), −143.3 (ddd, 1F, J=19.2 Hz, J=7.2 Hz, J=1.5 Hz).

MS (EI): m/e (%)=390 (69, [M+1]$^+$), 361 (100, [M−Et]$^+$).

Example 29

2-Butyl-5-(4'-ethyl-2,3-difluorobiphenyl-4-yl)selenophene

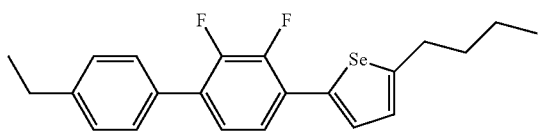

29.1 Preparation of 2-but-1-enyl-5-(4'-ethyl-2,3-difluorobiphenyl-4-yl)-selenophene

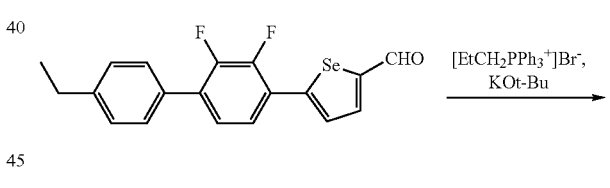

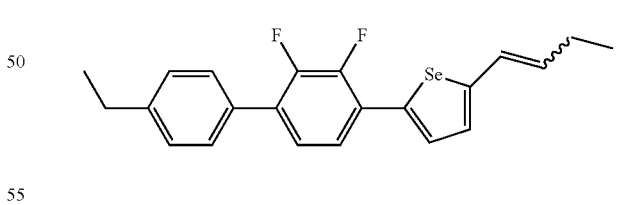

4.8 g (12.0 mmol) of propyltriphenylphosphonium bromide are initially introduced together with 3.60 g (9.56 mmol) of 5-(4'-ethyl-2,3-difluoro-biphenyl-4-yl)selenophene-2-carbaldehyde in 180 ml of THF, and a solution of 1.30 g (11.6 mmol) of potassium tert-butoxide in 20 ml of THF is added with ice-cooling. The mixture is stirred at RT for 1 h. Water and 2 N hydrochloric acid are added, and the batch is extracted with MTBE. The organic phase is washed with sat. sodium chloride soln. and dried using sodium sulfate. The solution is concentrated to dryness, and the residue is purified by column chromatography (SiO$_2$, n-heptane:toluene=95:5). 2-But-1-enyl-5-(4'-ethyl-2,3-difluorobiphenyl-4-yl)selenophene is obtained as a yellow solid.

29.2 Preparation of 2-butyl-5-(4'-ethyl-2,3-difluoro-biphenyl-4-yl)selenophene

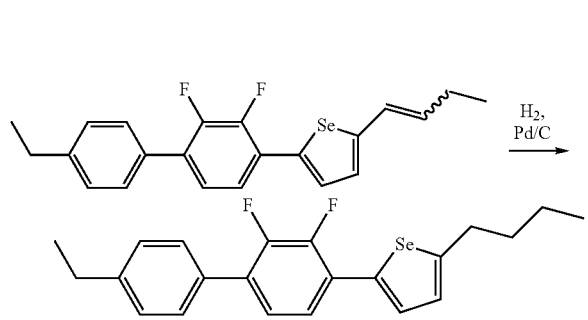

2.40 g (5.72 mmol) of 2-but-1-enyl-5-(4'-ethyl-2,3-difluorobiphenyl-4-yl)-selenophene are hydrogenated in 25 ml of ethyl acetate, in the presence of Pd/C (5% of Pd) at atmospheric pressure and RT. The reaction soln. is filtered and concentrated to dryness, and the crude product is purified by column chromatography (SiO$_2$, n-heptane:toluene=9:1). The further purification is carried out by recrystallisation from ethanol and n-heptane. 2-Butyl-5-(4'-ethyl-2,3-difluorobiphenyl-4-yl)selenophene is obtained as a colourless solid (m.p. 73° C.).

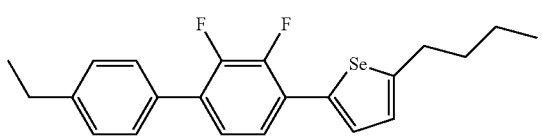

Δ∈=−2.1
Δn=0.2326
γ$_1$=98 mPa·s
C 73 N 88 I $^1$H-NMR (300 MHz, CHCl$_3$): δ=7.51-7.47 (m, 3H, H$_{arom.}$), 7.35-7.27 (m, 3H, H$_{arom.}$), 7.19-7.14 (m, 1H, H$_{arom.}$), 6.98-6.95 (m, 1H, H$_{arom.}$), 2.91 (t, 2H, J=7.6 Hz, CH$_2$(CH$_2$)$_2$CH$_3$), 2.70 (q, 2H, J=7.6 Hz, CH$_2$CH$_3$), 1.74-1.67 (m, 2H, CH$_2$(CH$_2$)$_2$CH$_3$), 1.49-1.39 (m, 2H, CH$_2$(CH$_2$)$_2$CH$_3$), 1.28 (t, 3H, J=7.6 Hz, CH$_2$CH$_3$), 0.96 (t, 3H, J=7.4 Hz, CH$_2$(CH$_2$)$_2$CH$_3$).
$^{19}$F-NMR (376 MHz, CHCl$_3$): δ=−140.2 (dd, 1F, J=19.2 Hz, J=7.3 Hz), −143.3 (ddd, 1F, J=19.2 Hz, J=7.3 Hz, J=1.5 Hz).
MS (EI): m/e (%)=404 (73, [M+1]$^+$), 361 (100, [M−Pr]$^+$).

Example 30

2-(4-Ethoxy-2,3-difluorophenyl)-5-propyltellurophene

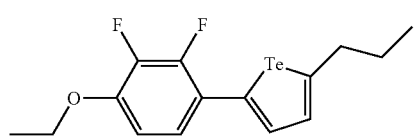

30.1 Preparation of 2-(4-ethoxy-2,3-difluorophenyl)tellurophene

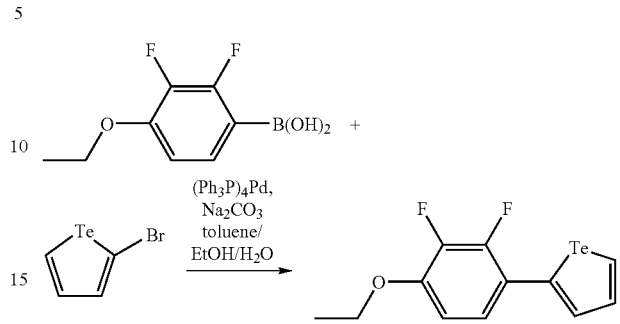

A mixture of 10.0 g (38.7 mmol) of 2-bromotellurophene, 8.0 g (39.6 mmol) of 4-ethoxy-2,3-difluorophenylboronic acid, 3.5 g (3.0 mmol) of tetrakis-(triphenylphosphine)palladium(0) and 100 ml of 2 N sodium carbonate soln. in 200 ml of toluene/ethanol (1:1) is heated under reflux for 1.5 h. After cooling, the organic phase is separated off, and the aqueous phase is extracted with toluene. The combined organic phases are washed with sat. sodium hydrogencarbonate soln., 1 N hydrochloric acid and sat. sodium chloride soln. The solution is dried using sodium sulfate and concentrated to dryness. The residue is purified by column chromatography (SiO$_2$, n-heptane:toluene=3:2). Further purification is carried out by recrystallisation from ethanol; 2-(4-ethoxy-2,3-difluorophenyl)tellurophene is obtained as a yellow solid.

30.2 Preparation of 5-(4-ethoxy-2,3-difluorophenyl)tellurophene-2-carbaldehyde

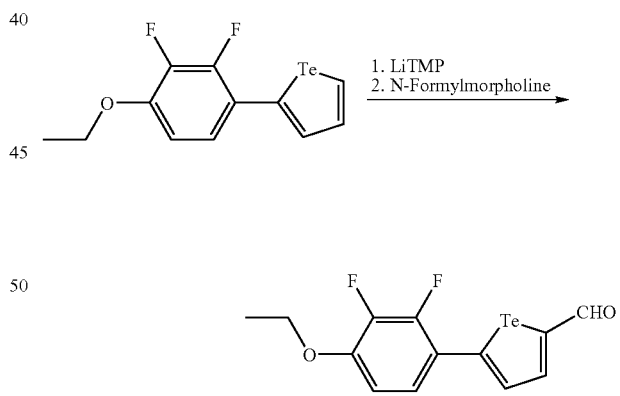

A solution of LiTMP (comprising 3.9 ml (22.9 mmol) of TMP and 14.0 ml (22.3 mmol, 15% soln. in hexane) of n-BuLi) is added to 6.8 g (20.3 mmol) of 2-(4-ethoxy-2,3-difluorophenyl)tellurophene in 70 ml of THF at 0° C. The mixture is stirred at this temperature for 1 h. The solution is cooled to −60° C., and N-formylmorpholine is added. The reaction mixture is warmed to 0° C. and stirred for 1 h. Water and 2 N hydrochloric acid are added, and the mixture is extracted with MTBE. The organic phase is washed with sodium chloride and dried using sodium sulfate. The solution is concentrated to dryness, and the residue is recrystallised from toluene. Drying in vacuo gives 5-(4-ethoxy-2,3-difluorophenyl)tellurophene-2-carbaldehyde as a brown solid.

30.3 Preparation of 2-(4-ethoxy-2,3-difluorophenyl)-5-propenyltellurophene

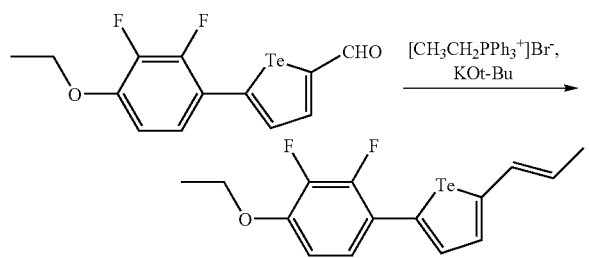

6.0 g (16.0 mmol) of ethyltriphenylphosphonium bromide are initially introduced together with 5.2 g (14.3 mmol) of 5-(4-ethoxy-2,3-difluorophenyl)-tellurophene-2-carbaldehyde in 150 ml of THF at 0° C., and 0.89 g (7.9 mmol) of potassium tert-butoxide dissolved in 7 ml of THF is added. After 2 h at room temperature, the mixture is diluted with MTBE, and water and 2 N hydrochloric acid are added. The organic phase is separated off, and the aqueous phase is extracted with MTBE. The combined organic phases are washed with sat. sodium chloride soln. and dried using sodium sulfate. The solution is concentrated to dryness, and the residue is purified by column chromatography (SiO$_2$, n-heptane:toluene=3:2). Further purification is carried out by recrystallisation from ethanol; 2-(4-ethoxy-2,3-difluorophenyl)-5-propenyltellurophene is obtained as a yellowish solid.

30.4 Preparation of 2-(4-ethoxy-2,3-difluorophenyl)-5-propyltellurophene

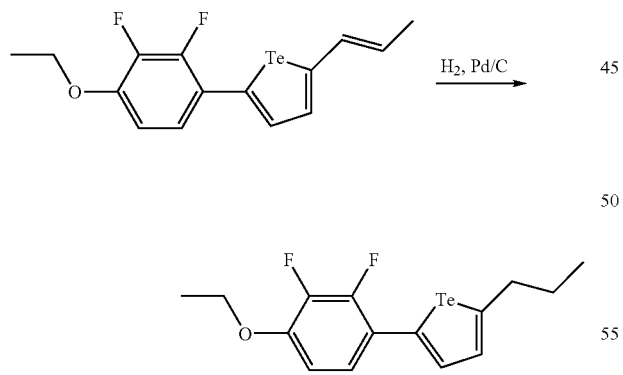

1.50 g (4.77 mmol) of 2-(4-ethoxy-2,3-difluorophenyl)-5-propenyltellurophene are hydrogenated in 15 ml of THF, in the presence of Pd/C (5% of Pd) at atmospheric pressure and RT. The reaction soln. is filtered and concentrated to dryness, and the crude product is purified by column chromatography (SiO$_2$, n-heptane:toluene=3:1). The further purification is carried out by recrystallisation from n-heptane. 2-(4-Ethoxy-2,3-difluorophenyl)-5-propyltellurophene is obtained as a colourless solid (m.p. 76° C.).

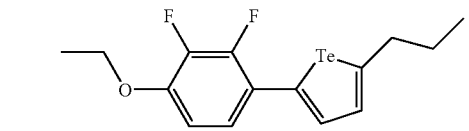

$\Delta \varepsilon = -3.2$
$\Delta n = 0.1573$
$\gamma_1 = 66$ mPa·s
C 76 I $^1$H-NMR (300 MHz, CHCl$_3$): δ=7.68 (d, 1H, J=3.9 Hz, 4-H), 7.36-7.32 (m, 1H, 3-H), 7.17 (ddd, 1H, J=8.0 Hz, J=7.4 Hz, J=2.4 Hz, H.), 6.71 (ddd, 1H, J=8.0 Hz, J=7.4 Hz, J=2.0 Hz, H.), 4.13 (q, 2H, J=7.0 Hz, H$_3$CCH$_2$O—), 2.92 (t, 2H, J=7.6 Hz, CH$_2$CH$_2$CH$_3$), 1.76-1.64 (m, 2H, CH$_2$CH$_2$CH$_3$), 1.46 (t, 3H, J=7.0 Hz, H$_3$CCH$_2$O—), 1.02 (t, 3H, J=7.6 Hz, CH$_2$CH$_2$CH$_3$).

$^{19}$F-NMR (282 MHz, CHCl$_3$): δ=−139.4 (dd, 2F, J=19.4 Hz, J=8.3 Hz), −158.7 (ddd, 2F, J=19.4 Hz, J=7.4 Hz, J=2.0 Hz).

MS (EI): m/e (%)=380 (83, [M+2]), 351 (100, [M+2−Et]$^+$), 323 (61), 193 (80).

The invention claimed is:
1. A compound of formula I

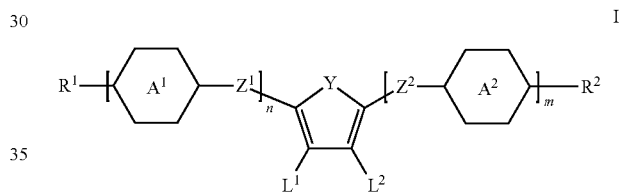

in which
Y denotes Se or Te,
L$^1$ and L$^2$ each, independently of one another, denotes H, halogen, CN, CF$_3$ or an alkyl group having 1 to 5 C atoms,
R$^1$ and R$^2$ each, independently of one another, denotes F, Cl, —CN, —NCS, —SF$_5$, —CF$_3$, —CHF$_2$, —CH$_2$F, —OCF$_3$, —OCHF$_2$, —OCH$_2$F or an alkyl group having 1 to 15 C atoms, which may optionally be monosubstituted by CN or at least monosubstituted by halogen, in which one or more CH$_2$ groups may each be replaced, independently of one another, by —O—, —S—, —CH═CH—, —CF═CF—, —CF═CH— or —CH═CF— in such a way that neither O nor S atoms are linked directly to one another,
or a polymerizable group,

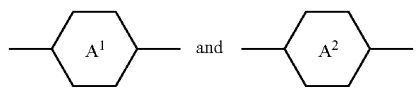

each, independently of one another, denotes
(a) a trans-1,4-cyclohexylene radical, in which one or two non-adjacent CH$_2$ groups may be replaced by —O— and/or —S—,
(b) a 1,4-cyclohexenylene radical,
(c) a 1,4-phenylene radical, in which one or two non-adjacent CH groups may be replaced by N, (d) a radical selected from the group consisting of naphthalene-2,6-diyl, decahydronaphthalene-2,6-diyl, 1,2,3,4-tetrahydronaphthalene-2,6-diyl and indane-2,5-diyl, (e) a radical selected from the group consisting of 1,3-cyclobutylene, 1,4-bicyclo[2.2.2]octylene, 1,3-bicyclo[1.1.1]-pentylene and spiro-[3.3]-heptane-2,6-diyl, or (f) a radical selected from the group consisting of the following formulae and their minor images

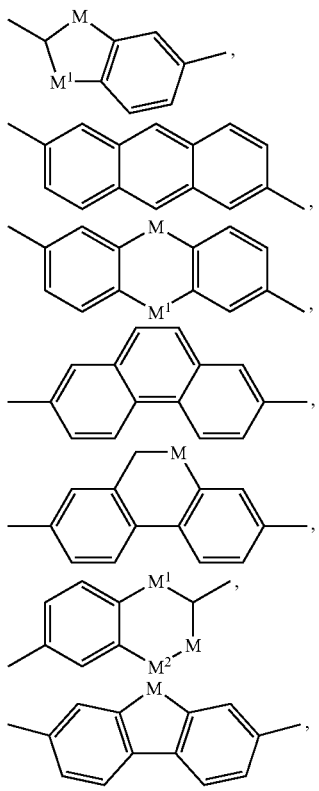

in which hydrogen atoms may be mono- or polysubstituted by F, Cl, CN, NCS, SF$_5$, CH$_2$F, CHF$_2$, CF$_3$, OCH$_2$F, OCHF$_2$ or OCF$_3$, and one or more double bonds may be replaced by single bonds, M, M$^1$ and M$^2$ each, independently of one another, denotes —O—, —S—, —CH$_2$—, —CHY— or —CY'Y$^2$— in such a way that adjacent groups do not simultaneously denote —O— or —S—, Y$^1$ and Y$^2$ each, independently of one another, denotes Cl, F, CN, OCF$_3$ or CF$_3$, wherein in (a) and (b), one or more H atoms may be replaced, independently of one another, by F, and in (b), (c) and (d), one, two or three —CH= groups may each be replaced, independently of one another, by a group selected from the group consisting of —CF=, —CCl=, —CBr=, —C(CN)=, —C(CH$_3$)=, —C(CH$_2$F)=, —C(CHF$_2$)=, —C(OCH$_3$)=, —C(OCHF$_2$)= and —C(OCF$_3$)=, and one or more —CH$_2$— groups may be replaced by —CF$_2$—, Z$^1$ and Z$^2$ each, independently of one another, denotes a single bond, —CH$_2$—CH$_2$—, —CF$_2$—CH$_2$—, —CH$_2$—CF$_2$—, —CF$_2$—CF$_2$—, —CHF—CHF—, —CH$_2$—CHF—, —CHF—CH$_2$—, —CH=CH—, —CF=CF—, —CF=CH—, —CH=CF—, —C≡C—, —(CO)O—, —O(CO)—, —CH$_2$O—, —OCH$_2$—, —CF$_2$O—, —OCF$_2$— or a combination of two of these groups, where no two O atoms are connected to one another, n denotes 0, and m denotes 0, 1, 2, 3 or 4, with the proviso that compounds wherein n=0, m=1, Z$^2$=a single bond, A$^2$=1,4-phenylene and R$^2$=CN, or OH are excluded, and with the proviso that compounds having the following formula are excluded

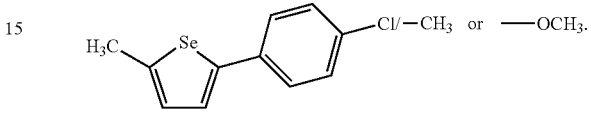

2. A compound according to claim 1, which is of formula IA or IB

IA
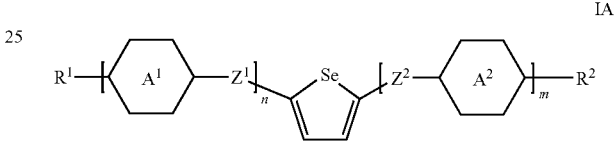

IB
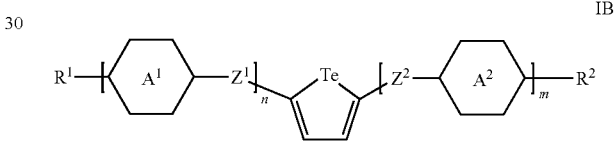

in which R$^1$, R$^2$, Z$^1$, Z$^2$, n, m,

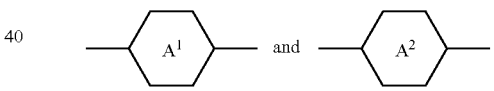

have the meanings given for the compound of formula I.

3. A compound according to claim 1, wherein Z$^1$ and Z$^2$ each denote a single bond.

4. A compound according to claim 1, wherein (m+n) denotes 1 or 2.

5. A compound according to claim 1, wherein R$^1$ and R$^2$ each, independently of one another, denotes an alkyl, alkoxy, alkenyl or alkenyloxy group having up to 8 C atoms, and one of the groups from R$^1$ and R$^2$ also additionally denotes halogen, —CN, —NCS, —SF$_5$, —CF$_3$, —CHF$_2$, —CH$_2$F, —OCF$_3$, —OCH$_2$F or —OCHF$_2$.

6. A liquid-crystal medium, comprising a compound of formula I and a further liquid-crystalline compound I
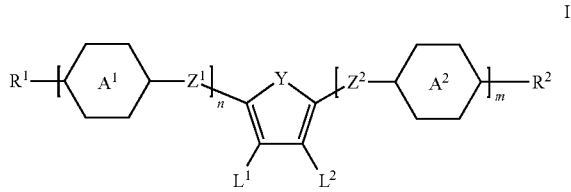

in which

Y denotes Se or Te, $L^1$ and $L^2$ each, independently of one another, denotes H, halogen, CN, $CF_3$ or an alkyl group having 1 to 5 C atoms, $R^1$ and $R^2$ each, independently of one another, denotes H, F, Cl, —CN, —NCS, —$SF_5$, —$CF_3$, —$CHF_2$, —$CH_2F$, —$OCF_3$, —$OCHF_2$, —$OCH_2F$ or an alkyl group having 1 to 15 C atoms, which may optionally be monosubstituted by CN or at least monosubstituted by halogen, in which one or more $CH_2$ groups may each be replaced, independently of one another, by —O—, —S—, —CH=CH—, —CF=CF—, —CF=CH— or —CH=CF— in such a way that neither O nor S atoms are linked directly to one another, or a polymerizable group,

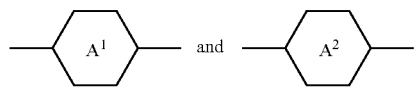

each, independently of one another, denotes (a) a trans-1,4-cyclohexylene radical, in which one or two non-adjacent $CH_2$ groups may be replaced by —O— and/or —S—, (b) a 1,4-cyclohexenylene radical, (c) a 1,4-phenylene radical, in which one or two non-adjacent CH groups may be replaced by N, (d) a radical selected from the group consisting of naphthalene-2,6-diyl, decahydronaphthalene-2,6-diyl, 1,2,3,4-tetrahydronaphthalene-2,6-diyl and indane-2,5-diyl, (e) a radical selected from the group consisting of 1,3-cyclobutylene, 1,4-bicyclo[2.2.2]octylene, 1,3-bicyclo[1.1.1]-pentylene and spiro-[3.3]heptane-2,6-diyl, or (f) a radical selected from the group consisting of the following formulae and their mirror images

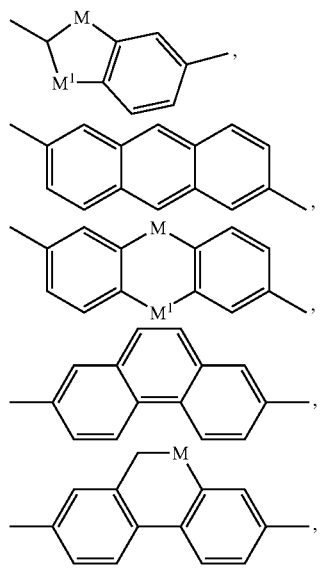

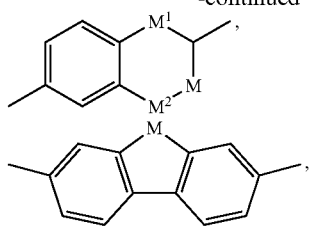

in which hydrogen atoms may be mono- or polysubstituted by F, Cl, CN, NCS, $SF_5$, $CH_2F$, $CHF_2$, $CF_3$, $OCH_2F$, $OCHF_2$ or $OCF_3$, one or more double bonds may be replaced by single bonds, M, $M^1$ and $M^2$ each, independently of one another, denotes —O—, —S—, —$CH_2$—, —CHY— or —$CY^1Y^2$— in such a way that adjacent groups do not simultaneously denote —O— or —S—, $Y^1$ and $Y^2$ each, independently of one another, denote Cl, F, CN, $OCF_3$ or $CF_3$, wherein in (a) and (b), one or more H atoms may be replaced, independently of one another, by F, and in (b), (c) and (d), one, two or three —CH= groups may each be replaced, independently of one another, by a group selected from the group consisting of —CF=, —CCl=, —CBr=, —C(CN)=, —C($CH_3$)=, —C($CH_2F$)=, —C($CHF_2$)=, —C($OCH_3$)=, —C($OCHF_2$)= and —C($OCF_3$)=, and one or more —$CH_2$— groups may be replaced by —$CF_2$—, $Z^1$ and $Z^2$ each, independently of one another, denotes a single bond, —$CH_2$—$CH_2$—, —$CF_2$—$CH_2$—, —$CH_2$—$CF_2$—, —$CF_2$—$CF_2$—, —CHF—CHF—, —$CH_2$—CHF—, —CHF—$CH_2$—, —CH=CH—, —CF=CF—, —CF=CH—, —CH=CF—, —C≡C—, —(CO)O—, —O(CO)—, —$CH_2$O—, —$OCH_2$—, —$CF_2$O—, —$OCF_2$— or a combination of two of these groups, where no two O atoms are connected to one another, and n and m each, independently of one another, denotes 0, 1, 2, 3 or 4, wherein (n+m) denotes 1, 2, 3 or 4, with the proviso that compounds wherein $R^1$ or $R^2$ denotes hydrogen and $A^1$ or $A^2$ connected thereto denotes a 1,4-cyclohexenylene radical or 1,3-cyclobutylene radical are excluded, and with the proviso that compounds wherein $R^1$ and $R^2$ both denote H, both denote F or both denote Cl are excluded, and with the proviso that compounds wherein n=0, m=1, $Z^2$=a single bond, $A^2$=1,4-phenylene and $R^2$=CN, OH or H are excluded, and with the proviso that compounds wherein n=1, m=1, $Z^2$=a single bond, $A^1$=$A^2$=1,4-phenylene and $R^2$=CN, OH or H are excluded, and with the proviso that compounds wherein n=0, m=1, $Z^2$=a single bond, $A^2$=1,4-phenylene and $R^1$=H are excluded, and with the proviso that compounds having the following formula are excluded

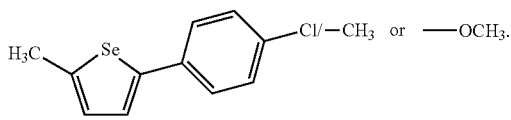

and with the proviso that the compound having the following formula is excluded

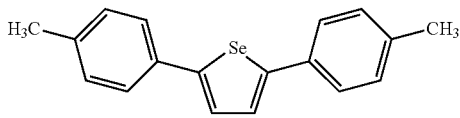

and with the proviso that the compound having the following formula is excluded

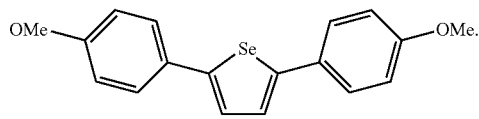

7. An electro-optical display containing a liquid-crystal medium according to claim 6.

8. A process for preparing a compound according to claim 1, comprising reacting a 2-bromo- or 2-iodoselenophene compound or a 2-iodo- or 2-bromotellurophene compound with an aryl- or alkenylboronic acid, an aryl- or alkenylboronic acid ester, a terminal alkyne, a terminal alkene or an organomagnesium or organozinc compound.

9. A compound of formula II

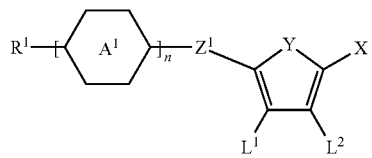

II in which
Y denotes Se or Te,
$L^1$ and $L^2$ each, independently of one another, denotes H, halogen, CN, $CF_3$ or an alkyl group having 1 to 5 C atoms,
$R^1$ denotes F, Cl, —CN, —NCS, —$SF_5$, —$CF_3$, —$CHF_2$, —$CH_2F$, —$OCF_3$, —$OCHF_2$, —$OCH_2F$ or an alkyl group having 1 to 15 C atoms, which may optionally be monosubstituted by CN or at least monosubstituted by halogen, in which one or more $CH_2$ groups may each be replaced, independently of one another, by —O—, —S—, —CH=CH—, —CF=CF—, —CF=CH— or —CH=CF— in such a way that neither O nor S atoms are linked directly to one another,
or a polymerizable group,

denotes
(a) a trans-1,4-cyclohexylene radical, in which one or two non-adjacent $CH_2$ groups may be replaced by —O— and/or —S—,
(b) a 1,4-cyclohexenylene radical,
(c) a 1,4-phenylene radical, in which one or two non-adjacent CH groups may be replaced by N,
(d) a radical selected from the group consisting of naphthalene-2,6-diyl, decahydronaphthalene-2,6-diyl, 1,2,3,4-tetrahydronaphthalene-2,6-diyl and indane-2,5-diyl,
(e) a radical selected from the group consisting of 1,3-cyclobutylene, 1,4-bicyclo[2.2.2]octylene, 1,3-bicyclo[1.1.1]-pentylene and spiro-[3.3]heptane-2,6-diyl, or
(f) a radical selected from the group consisting of the following formulae and their mirror images

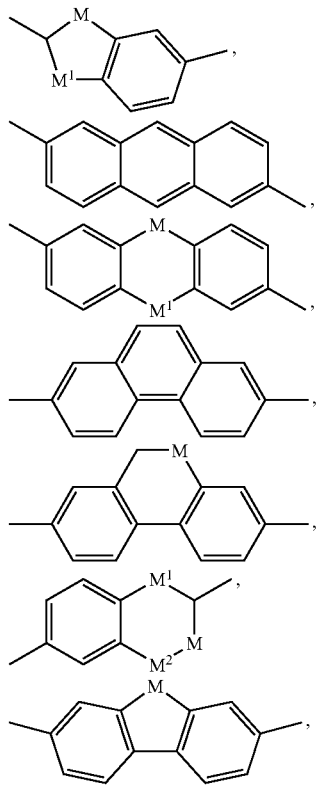

in which hydrogen atoms may be mono- or polysubstituted by F, Cl, CN, NCS, $SF_5$, $CH_2F$, $CHF_2$, $CF_3$, $OCH_2F$, $OCHF_2$ or $OCF_3$, one or more double bonds may be replaced by single bonds,
M, $M^1$ and $M^2$ each, independently of one another, denotes —O—, —S—, —$CH_2$—, —CHY— or —$CY^1Y^2$— in such a way that adjacent groups do not simultaneously denote —O— or —S—,
$Y^1$ and $Y^2$ each, independently of one another, denote Cl, F, CN, $OCF_3$ or $CF_3$,
wherein
in (a) and (b), one or more H atoms may be replaced, independently of one another, by F, and in (b), (c) and (d), one, two or three —CH= groups may each be replaced, independently of one another, by a group selected from the group consisting of —CF=, —CCl=, —CBr=, —C(CN)=, —C($CH_3$)=, —C($CH_2F$)=, —C($CHF_2$)=, —C($OCH_3$)=, —C($OCHF_2$)= and —C($OCF_3$)=, and one or more —$CH_2$— groups may be replaced by —$CF_2$—,
$Z^1$ denotes a single bond, —$CH_2$—$CH_2$—, —$CF_2$—$CH_2$—, —$CH_2$—$CF_2$—, —$CF_2$—$CF_2$—, —CHF—CHF—, —$CH_2$—CHF—, —CHF—$CH_2$—, —CH=CH—, —CF=CF—, —CF=CH—, —CH=CF—, —C≡C—, —(CO)O—, —O(CO)—, —CH₂O—, —OCH₂—, —CF₂O—, —OCF₂— or a combination of two of these groups, where no two O atoms are connected to one another, n denotes 1, 2, 3 or 4, X denotes —Cl, —Br, —I, —O(SO₂)R³, —B(OH)₂, —B(OR⁴)₂, —CH₂OH, —CF₂Br or —CHO, R³ denotes 1-5 C alkyl, 1-5 C perfluoroalkyl or p-tolyl, and R⁴ denotes 1-12 C alkyl or R⁴+R⁴ together denote a 1,2- or 1,3-alkylene or a 1,2-phenylene group, which may optionally be substituted by one or more 1-4 C alkyl groups, where compounds for which n=1, A¹ denotes an unsubstituted 1,4-phenylene or pyridine-2,5-diyl and R¹ denotes Cl, —OCH₃ or CN are excluded.

10. A liquid-crystal medium according to claim 6, wherein the compound of formula I is a compound of formulae IA and IB $$R^1-\!\!\left\{\!\!\bigcirc\!\!A^1\!\!\bigcirc\!\!\right\}\!\!-\!Z^1\!\!-\!\!\left[\!\!\bigcirc\!\!Se\!\!\bigcirc\!\!\right]_n\!\!-\!Z^2\!\!-\!\!\left\{\!\!\bigcirc\!\!A^2\!\!\bigcirc\!\!\right\}_m\!\!-\!R^2 \quad \text{IA}$$

$$R^1-\!\!\left\{\!\!\bigcirc\!\!A^1\!\!\bigcirc\!\!\right\}\!\!-\!Z^1\!\!-\!\!\left[\!\!\bigcirc\!\!Te\!\!\bigcirc\!\!\right]_n\!\!-\!Z^2\!\!-\!\!\left\{\!\!\bigcirc\!\!A^2\!\!\bigcirc\!\!\right\}_m\!\!-\!R^2 \quad \text{IB}$$

in which R¹, R², Z¹, Z², n, m, $$-\!\!\bigcirc\!\!A^1\!\!\bigcirc\!\!-\quad\text{and}\quad-\!\!\bigcirc\!\!A^2\!\!\bigcirc\!\!-$$

have the meanings given for the compound of formula I.

11. A liquid-crystal medium according to claim 6, wherein, in the compound of formula I, one of the variables n or m denotes 0.

12. A liquid-crystal medium according to claim 6, wherein, in the compound of formula I, Z¹ and Z² each denote a single bond.

13. A liquid-crystal medium according to claim 6, wherein, in the compound of formula I, (m+n) denotes 1 or 2.

14. A liquid-crystal medium according to claim 6, wherein, in the compound of formula I, R¹ and R² each, independently of each other, denotes an alkyl, alkoxy, alkenyl or alkenyloxy group having up to 8 C atoms, and one of the groups from R¹ and R² also additionally denotes halogen, —CN, —NCS, —SF₅, —CF₃, —CHF₂, —CH₂F, —OCF₃, —OCH₂F or —OCHF₂.

15. A liquid-crystal medium according to claim 6, wherein, in the compound of formula I, n denotes 0.

16. A liquid-crystal medium according to claim 15, wherein, in the compound of formula I, R¹ and R² each, independently of one another, denotes F, Cl, —CN, —NCS, —SF₅, —CF₃, —CHF₂, —CH₂F, —OCF₃, —OCHF₂, —OCH₂F or an alkyl group having 1 to 15 C atoms, which may optionally be monosubstituted by CN or at least monosubstituted by halogen, in which one or more CH₂ groups may each be replaced, independently of one another, by —O—, —S—, —CH=CH—, —CF=CF—, —CF=CH— or —CH=CF— in such a way that neither O nor S atoms are linked directly to one another, or a polymerizable group.

17. A liquid-crystal medium according to claim 15, wherein, in the compound of formula I, R¹ and R² each, independently of each other, denotes an alkyl, alkoxy, alkenyl or alkenyloxy group having up to 8 C atoms, and one of the groups from R¹ and R² also additionally denotes halogen, —CN, —NCS, —SF₅, —CF₃, —CHF₂, —CH₂F, —OCF₃, —OCH₂F or —OCHF₂.

18. A liquid-crystal medium according to claim 1, wherein, in the compound of formula I, R¹ and R² each, independently of one another, denotes F, Cl, —CN, —NCS, —SF₅, —CF₃, —CHF₂, —CH₂F, —OCF₃, —OCHF₂, —OCH₂F or an alkyl group having 3 to 15 C atoms, which may optionally be monosubstituted by CN or at least monosubstituted by halogen, in which one or more CH₂ groups may each be replaced, independently of one another, by —O—, —S—, —CH=CH—, —CF=CF—, —CF=CH— or —CH=CF— in such a way that neither O nor S atoms are linked directly to one another, or a polymerizable group.

19. A liquid-crystal medium according to claim 7, wherein, in the compound of formula I, R¹ and R² each, independently of one another, denotes F, Cl, —CN, —NCS, —SF₅, —CF₃, —CHF₂, —CH₂F, —OCF₃, —OCHF₂, —OCH₂F or an alkyl group having 3 to 15 C atoms, which may optionally be monosubstituted by CN or at least monosubstituted by halogen, in which one or more CH₂ groups may each be replaced, independently of one another, by —O—, —S—, —CH=CH—, —CF=CF—, —CF=CH— or —CH=CF— in such a way that neither O nor S atoms are linked directly to one another, or a polymerizable group.

20. An electro-optical display containing a compound of formula I $$R^1-\!\!\left\{\!\!\bigcirc\!\!A^1\!\!\bigcirc\!\!\right\}\!\!-\!Z^1\!\!-\!\!\left[\!\!\bigcirc\!\!\overset{Y}{\underset{L^1\ L^2}{\bigcirc}}\!\!\bigcirc\!\!\right]_n\!\!-\!Z^2\!\!-\!\!\left\{\!\!\bigcirc\!\!A^2\!\!\bigcirc\!\!\right\}_m\!\!-\!R^2 \quad \text{I}$$

in which

Y denotes Se or Te,

L¹ and L² each, independently of one another, denotes H, halogen, CN, CF₃ or an alkyl group having 1 to 5 C atoms, R¹ and R² each, independently of one another, denotes H, F, Cl, —CN, —NCS, —SF₅, —CF₃, —CHF₂, —CH₂F, —OCF₃, —OCHF₂, —OCH₂F or an alkyl group having 1 to 15 C atoms, which may optionally be monosubstituted by CN or at least monosubstituted by halogen, in which one or more CH₂ groups may each be replaced, independently of one another, by —O—, —S—, —CH=CH—, —CF=CF—, —CF=CH— or —CH=CF— in such a way that neither O nor S atoms are linked directly to one another,
or a polymerizable group,

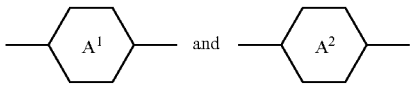

each, independently of one another, denotes
(a) a trans-1,4-cyclohexylene radical, in which one or two non-adjacent $CH_2$ groups may be replaced by —O— and/or —S—,
(b) a 1,4-cyclohexenylene radical,
(c) a 1,4-phenylene radical, in which one or two non-adjacent CH groups may be replaced by N,
(d) a radical selected from the group consisting of naphthalene-2,6-diyl, decahydronaphthalene-2,6-diyl, 1,2,3,4-tetrahydronaphthalene-2,6-diyl and indane-2,5-diyl,
(e) a radical selected from the group consisting of 1,3-cyclobutylene, 1,4-bicyclo[2.2.2]octylene, 1,3-bicyclo[1.1.1]pentylene and spiro-[3.3]heptane-2,6-diyl, or
(f) a radical selected from the group consisting of the following formulae and their mirror images

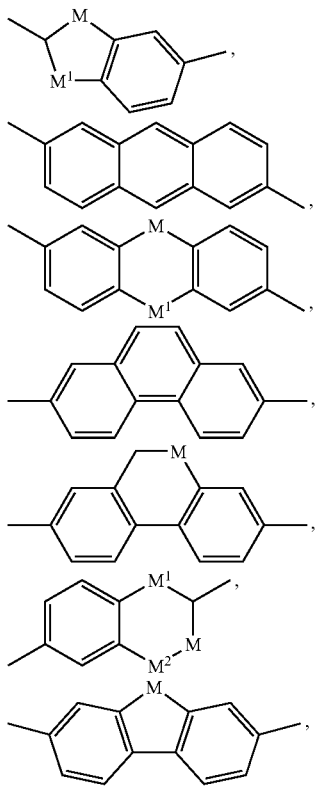

in which hydrogen atoms may be mono- or polysubstituted by F, Cl, CN, NCS, $SF_5$, $CH_2F$, $CHF_2$, $CF_3$, $OCH_2F$, $OCHF_2$ or $OCF_3$, one or more double bonds may be replaced by single bonds,
M, $M^1$ and $M^2$ each, independently of one another, denotes —O—, —S—, —$CH_2$—, —CHY— or —$CY^1Y^2$— in such a way that adjacent groups do not simultaneously denote —O— or —S—, $Y^1$ and $Y^2$ each, independently of one another, denote Cl, F, CN, $OCF_3$ or $CF_3$,
wherein
in (a) and (b), one or more H atoms may be replaced, independently of one another, by F, and in (b), (c) and (d), one, two or three —CH= groups may each be replaced, independently of one another, by a group selected from the group consisting of —CF=, —CCl=, —CBr=, —C(CN)=, —C($CH_3$)=, —C($CH_2F$)=, —C($CHF_2$)=, —C($OCH_3$)=, —C($OCHF_2$)= and —C($OCF_3$)=, and one or more —$CH_2$— groups may be replaced by —$CF_2$—,
$Z^1$ and $Z^2$ each, independently of one another, denotes a single bond, —$CH_2$—$CH_2$—, —$CF_2$—$CH_2$—, —$CH_2$—$CF_2$—, —$CF_2$—$CF_2$—, —CHF—CHF—, —$CH_2$—CHF—, —CHF—$CH_2$—, —CH=CH—, —CF=CF—, —CF=CH—, —CH=CF—, —C≡C—, —(CO)O—, —O(CO)—, —$CH_2$O—, —$OCH_2$—, —$CF_2$O—, —$OCF_2$— or a combination of two of these groups, where no two O atoms are connected to one another, and
n and m each, independently of one another, denotes 0, 1, 2, 3 or 4, wherein (n+m) denotes 1, 2, 3 or 4,
with the proviso that compounds wherein $R^1$ or $R^2$ denotes hydrogen and $A^1$ or $A^2$ connected thereto denotes a 1,4-cyclohexenylene radical or 1,3-cyclobutylene radical are excluded,
and with the proviso that compounds wherein $R^1$ and $R^2$ both denote H, both denote F or both denote Cl are excluded,
and with the proviso that compounds wherein n=0, m=1, $Z^2$=a single bond, $A^2$=1,4-phenylene and $R^2$=CN, OH or H are excluded,
and with the proviso that compounds wherein n=1, m=1, $Z^2$=a single bond, $A^1$=$A^2$=1,4-phenylene and $R^2$=CN, OH or H are excluded,
and with the proviso that compounds wherein n=0, m=1, $Z^2$=a single bond, $A^2$=1,4-phenylene and $R^1$=H are excluded,
and with the proviso that compounds having the following formula are excluded

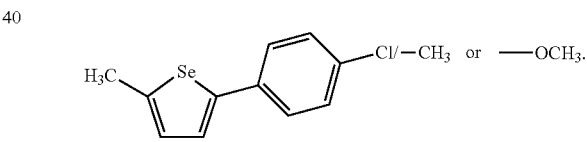

and with the proviso that the compound having the following formula is excluded

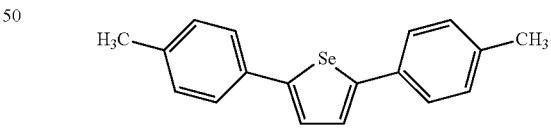

and with the proviso that the compound having the following formula is excluded

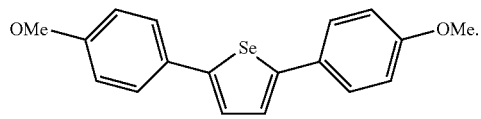

* * * * *